US006908926B1

(12) United States Patent
Dörwald et al.

(10) Patent No.: US 6,908,926 B1
(45) Date of Patent: Jun. 21, 2005

(54) SUBSTITUTED IMIDAZOLES, THEIR PREPARATION AND USE

(75) Inventors: Florencio Zaragoza Dörwald, Ballerup (DK); Knud Erik Andersen, Brøndby (DK); Tine Krogh Jørgensen, Ølstykke (DK); Bernd Peschke, Måløv (DK); Birgitte Schjellerup Wulff, Virum (DK); Ingrid Pettersson, Frederiksberg (DK); Klaus Rudolf, Warthausen (DE); Dirk Stenkamp, Biberach (DE); Rudolf Hurnaus, Biberach (DE); Stephan Georg Müller, Warthausen (DE); Bernd Krist, Ulm (DE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/548,081

(22) Filed: Apr. 12, 2000

Related U.S. Application Data
(60) Provisional application No. 60/176,709, filed on Jan. 18, 2000, provisional application No. 60/156,496, filed on Sep. 28, 1999, and provisional application No. 60/130,192, filed on Apr. 20, 1999.

(30) Foreign Application Priority Data

| Apr. 16, 1999 | (DK) | 1999 00508 |
| Sep. 22, 1999 | (DK) | 1999 01345 |
| Jan. 12, 2000 | (DK) | 2000 00042 |

(51) Int. Cl.$^7$ .............. A61K 31/437; C07D 471/04
(52) U.S. Cl. .............. 514/278; 514/211.11; 514/303; 514/409; 514/412; 540/543; 540/578; 546/18; 546/118; 548/411; 548/453
(58) Field of Search .............. 546/18, 118; 514/278, 514/303, 211.11; 540/588

(56) References Cited

U.S. PATENT DOCUMENTS

| 4,767,778 | A | 8/1988 | Arrang et al. ........... 514/397 |
| 5,091,390 | A | 2/1992 | Ardecky et al. ........ 514/303 |
| 5,262,537 | A | 11/1993 | Huang et al. ........... 546/118 |
| 5,578,616 | A | 11/1996 | Aslanian et al. ........ 514/341 |

FOREIGN PATENT DOCUMENTS

| DE | 27 00 012 | 7/1977 |
| DE | 33 02 125 | 7/1984 |
| DE | 33 02 126 | 7/1984 |
| EP | 0 197 840 | 10/1986 |
| EP | 0 214 058 | 3/1987 |
| EP | 0 338 939 | 10/1989 |
| EP | 0 458 661 A1 | 11/1991 |
| EP | 0 494 010 | 7/1992 |
| EP | 0 499 521 | 8/1992 |
| EP | 0 531 219 | 3/1993 |
| EP | 0 531 874 | 3/1993 |
| EP | 0 589 665 | 3/1994 |
| FR | 2 337 726 | 3/1980 |
| GB | 1 524 481 | 9/1978 |
| GB | 2 158 440 | 11/1985 |
| JP | 6-312926 | 8/1994 |
| WO | WO 91/17146 | 11/1991 |
| WO | WO 92/15567 | 9/1992 |
| WO | WO 92/18115 | 10/1992 |
| WO | WO 93/12093 | 6/1993 |
| WO | WO 93/12107 | 6/1993 |
| WO | WO 93/12108 | 6/1993 |
| WO | WO 93/14070 | 7/1993 |
| WO | WO 93/20061 | 10/1993 |
| WO | WO 94/17058 | 8/1994 |
| WO | WO 95/06037 | 3/1995 |
| WO | WO 95/11894 | 5/1995 |
| WO | WO 95/14007 | 5/1995 |
| WO | WO 96/38141 | 12/1996 |
| WO | WO 96/38142 | 12/1996 |
| WO | WO 96/40126 | 12/1996 |
| WO | WO 98/29119 | 7/1998 |

OTHER PUBLICATIONS

CAS printout for Stocker et al. Chem. Abs. 112:216653, 1990.*
CAS printout for Arcari et al. Chem 80:45756.*
CAS printout for Enari et al.*
CAS printout for Klutchko et al.*
CAS printout for Vincent et al.*
CAS printout for Suzukiet et al.*
CAS printout for Thorwart et al.*
CAS printout for Remelli et al.*
CAS printout for Hauck et al.*
CAS printout for Yutilov et al.*
CAS printout for Stocker et al.*

(Continued)

Primary Examiner—Richard L. Raymond
(74) Attorney, Agent, or Firm—Rosemarie R. Wilk-Orescar; Reza Green; Richard W. Bork

(57) ABSTRACT

Disclosed is a novel class of substituted imidazole compounds, pharmaceutical compositions containing them and uses of these compounds in the treatment and/or prevention of diseases and disorders related to the histamine H3 receptor. More particularly, these compounds are useful for the treatment and/or prevention of diseases and disorders in which an interaction with the histamine H3 receptor is beneficial. These imidazoles compounds have the formula I

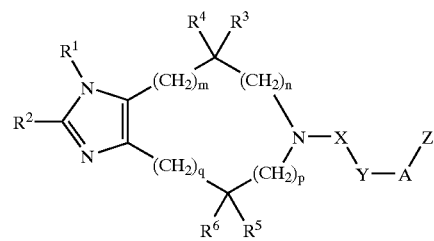

wherein $R^1$, $R^2$, $R^3$, $R^4$, $R^5$, $R^6$, A, X, Y and Z are as defined in the specification.

22 Claims, No Drawings

OTHER PUBLICATIONS

Williams et al., Journal of Pharmaceutical Sci., vol. 71, No. 1, pp. 119–120 (Jan. 1982).
Piper et al., Can. J. Chem., vol. 61, pp. 2721–2728 (1983).
Casella et al., J. Am. Chem. Soc., vol. 103, pp. 6338–6347 (1981).
Nagarajan et al., Indian Journal of Chem., vol. 15B, pp. 629–634 (Jul. 1977).
Emmett et al, J. Med. Chem., vol. 25, pp. 1168–1174 (1982).
Vitali et al., Chim. Ital., vol. 94, pp. 296–305 (1964).
Arcari et al., Arzneim. Forschung, vol. 34, pp. 1467–1471 (1984).
Habermehl et al., Heterocycles, vol. 5, pp. 127–134 (1976).
Hepp et al., Arch. Pharm. (Weinheim), vol. 313, pp. 756–762 (1980).
Arcari, et al., Chemical Abstract, 87:201535, pp. 730–731 (1977).
Klutchko et al., J. Heterocyclic Chem., vol. 28, pp. 97–108 (1991).
Lovenberg et al., Molecular Pharm., vol. 55, pp. 1101–1107 (1999).
Leurs et al., Progress in Drug Research, vol. 45, pp. 107–165 (1995).
Stark et al, Drugs of The Future, vol. 21, No. 5, pp. 507–520 (1996).
Vitali et al., Farmaco Ed. Sci., vol. 22, pp. 821–845 (1967).
Krause et al., J. Med. Chem., vol. 38, pp. 4070–4079 (1995).

* cited by examiner

SUBSTITUTED IMIDAZOLES, THEIR PREPARATION AND USE

CROSS-REFERENCES TO RELATED APPLICATIONS

The present application claims priority under 35 U.S.C. 119 of U.S. provisional application Nos. 60/130,192, 60/156,496 and 60/176,706 filed Apr. 20, 1999, Sep. 28, 1999 and Jan. 18, 2000, respectively, and Danish application Nos. PA 1999 00508, PA 1999 01345 and PA 2000 00042 filed Apr. 16, 1999, Sep. 22, 1999 and Jan. 12, 2000, respectively, the contents of which are fully incorporated herein by reference.

BACKGROUND OF THE INVENTION

1. Field of the Invention

The present invention relates to novel substituted imidazoles, to the use of these compounds as medicaments, to pharmaceutical compositions comprising the compounds, and to a method of treatment employing these compounds and compositions. The present compounds show a high and selective binding affinity to the histamine H3 receptor indicating histamine H3 receptor antagonistic or agonistic activity. As a result, the compounds are useful for the treatment and/or prevention of diseases and disorders related to the histamine H3 receptor.

2. Description of the Related Art

The existence of the histamine H3 receptor has been known for several years and of current interest for the development of new medicaments (see e.g. Stark, H.; Schlicker, E.; Schunack, W., *Drugs Fut.* 1996, 21, 507–520; Leurs, R.; Timmerman, H.; Vollinga, R. C., *Progress in Drug Research* 1995, 45, 107–165). Recently, the histamine H3 receptor has been cloned, cf. Lovenberg, T. W. et al, *Molecular Pharmacology*, June 1999, 55, 1101–1107. The histamine H3 receptor is a presynaptic autoreceptor located in both the central and the peripheral nervous systems, the skin, and in organs such as the lung, the intestine, probably the spleen and the gastrointestinal tract. The histamine H3 receptor has been demonstrated to regulate the release of histamine and also of other neurotransmitters such as serotonin and acetylcholine. A histamine H3 receptor antagonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists and antagonists could be important mediators of neuronal activity. Accordingly, the histamine H3 receptor is an important target for new therapeutics.

Imidazoles similar to the compounds of the present invention have previously been prepared, and their biological properties have been investigated. Thus, WO 98/29119 relates to tetrahydroimidazopyridine farnesyl-protein inhibitors. JP 06312927 discloses tetrahydroimidazopyridine intermediates for preparing angiosin II inhibitors. WO 93/17701 discloses tetrahydroimidazopyridine intermediates for preparing endothelin receptor-binding peptides. Klutchko, S., et al., *J. Heterocycl. Chem.*, 28(1), 1991, 97–108 relates to synthesis methods for the preparation of imidazole derivatives. GB 2158440 relates to antiviral compounds. Arcari, G.; Bernardi, L.; Cimaschi, R.; Falconi, G.; Luini, F.; Scarponi, U., *Arzneim. Forsch.*, 34, 11, 1984, 1467–1471, relates to tetrahydroimidazopyridine intermediates for the preparation of imidazopiperidines with anti-ulcer and antisecretory activity, and GB 2028798 relates to tetrahydroimidazopyridine intermediates for the preparation of antiulcer and anticholinergic compounds. However, these references neither disclose nor suggest that the imidazoles may have a histamine H3 receptor antagonistic or agonistic activity.

Furthermore, *Chem. Abstr.*, 87, 201535; Hepp, M.; Schunack, W., *Arch. Pharm. (Weinheim Ger.)*, 313, 9, 1980, 756–762; Vitali et al., *Farmaco Ed. Sci.*, 22, 1967, 821; Habermehl; Ecsy, *Heterocycles*, 5, 1976, 127; Vitali; Bertaccini, *Gazz. Chim. Ital.*, 94, 1964, 296; Emmett, J. C.; Durant, G. J.; Ganellin, C. R.; Roe, A. M.; Turner, J. L., *J. Med. Chem.*, 25, 10, 1982, 1168–1174; Nagarajan, K. et al., *Indian J. Chem. Sect. B*, 15, 1977, 629–634; Casella, L.; Gullotti, M., *J. Am. Chem. Soc.*, 103, 21, 1981, 6338–6347; Piper, I. M.; MacLean, D. B.; Kvarnstroem, I.; Szarek, W. A., *Can. J. Chem.*, 61, 1983, 2721–2728; Williams, R. L.; Neergaard, S., *J. Pharm. Sci.*, 71, 1, 1982, 119–120), DE 2700012, EP 589 665, EP 531 874, WO 92/18115, EP 449 521, U.S. Pat. No. 5,091,390, DE 33 02 125 and DE 33 02 126 disclose imidazopyridine derivatives which are stated to be useful either as intermediates or as therapeutically active substances such as angiotensin II antagonists effective to treat hypertension, peripheral kappa opioid receptor activating substances effective to treat inflammatory pain and N-myristoyl transferase inhibitors effective as anti-cancer agents. However, these references neither disclose nor suggest that the imidazoles may have a histamine H3 receptor antagonistic or agonistic activity.

Several publications disclose the preparation and use of histamine H3 agonists and antagonists. Thus, U.S. Pat. No. 4,767,778 (corresponding to EP 214 058), EP 338 939, WO 93/14070, EP 531 219, EP 458 661, EP 197 840, EP 494 010, WO 91/17146, WO 93/12108, WO 93/12107, WO 93/12093, U.S. Pat. No. 5,578,616 (corresponding to WO 95/14007), WO 96/38142, WO 96/38141, WO 95/11894, WO 93/20061, WO 96/40126, WO 95/06037, WO 92/15567 and WO 94/17058 disclose imidazole derivatives having histamine H3 receptor agonistic or antagonistic activity. However, the structures of these imidazole derivatives are quite different from that of the present compounds. Thus, none of the imidazole derivatives disclosed in these publications have a ring structure fused to the imidazole group such as is the case in the present compounds.

In view of the art's interest in histamine H3 receptor agonists and antagonists, novel compounds which interact with the histamine H3 receptor would be a highly desirable contribution to the art. The present invention provides such a contribution to the art being based on the finding that a specific class of substituted imidazole compounds has a high and specific affinity to the histamine H3 receptor. Some of these substituted imidazole derivatives are novel per se, thereby constituting a further aspect of the invention.

Due to their interaction with the histamine H3 receptor, the present compounds are useful in the treatment and/or prevention of a wide range of conditions and disorders in which an interaction with the histamine H3 receptor is beneficial. Thus, the compounds may find use, e.g., in the treatment of diseases of the central nervous system, the peripheral nervous system, the cardiovascular system, the pulmonary system, the gastrointestinal system and the endocrinologic system.

Definitions

In the structural formulas given herein and throughout the present specification, the following terms have the indicated meaning:

The term "$C_{1-6}$-alkyl" as used herein represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl, and the like.

The term "$C_{2-8}$-alkenyl" as used herein represents a branched or straight hydrocarbon group having from 2 to 8 carbon atoms and at least one double bond. Examples of such groups include, but are not limited to, vinyl, 1-propenyl, 2-propenyl, allyl, iso-propenyl, 1,3-butadienyl, 1-butenyl, 2-butenyl, 1-pentenyl, 2-pentenyl, 1-hexenyl, 2-hexenyl, 1-heptenyl, 2-heptenyl, 1-octenyl, 2-octenyl, and the like. In a similar way the term "$C_{2-6}$-alkenyl" represents a branched or straight hydrocarbon group having from 2 to 6 carbon atoms and at least one double bond.

The term "$C_{2-8}$-alkynyl" as used herein represents a branched or straight hydrocarbon group having from 2 to 8 carbon atoms and at least one triple bond. Examples of such groups include, but are not limited to, 1-propynyl, 2-propynyl, 1-butynyl, 2-butynyl, 1-pentynyl, 2-pentynyl, 1-hexynyl, 2-hexynyl, 1-heptynyl, 2-heptynyl, 1-octynyl, 2-octynyl, and the like. In a similar way the term "$C_{2-6}$-alkynyl" represents a branched or straight hydrocarbon group having from 2 to 6 carbon atoms and at least one triple bond.

The term "$C_{1-6}$-alkoxy" as used herein, alone or in combination, refers to the radical —O—$C_{1-6}$-alkyl where $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy, and the like.

The term "$C_{1-6}$-alkylthio" as used herein, alone or in combination, refers to the radical —S—$C_{1-6}$-alkyl where $C_{1-6}$-alkyl is as defined above. Representative examples are methylthio, ethylthio, isopropylthio, propylthio, butylthio, pentylthio, and the like.

The term "$C_{3-15}$-cycloalkyl" as used herein represents a carbocyclic group having from 3 to 15 carbon atoms such as from 3 to 8 carbon atoms. Representative examples are cyclopropyl, cyclobutyl, cyclopentyl, cyclohexyl, cycloheptyl, cyclooctyl, cyclononyl, cyclodecy, and the like. In the same way the term "$C_{3-8}$-cycloalkyl" represents a carbocyclic group having from 3 to 8 carbon atoms.

The term "$C_{3-15}$-cycloalkenyl" as used herein represents a carbocyclic group having from 3 to 15 carbon atoms, such as from 3 to 8 carbon atoms, and at least one double bond. Representative examples are cyclopropenyl, cyclobutenyl, cyclopentenyl, cyclohexenyl, cycloheptenyl, cyclooctenyl, cyclononenyl, cyclodecenyl, and the like.

The term "$C_{3-15}$-cycloalkynyl" as used herein represents a carbocyclic group having from 3 to 15 carbon atoms, such as from 3 to 8 carbon atoms, and at least one triple bond. Representative examples are cyclopropynyl, cyclobutynyl, cyclopentynyl, cyclohexynyl, cycloheptynyl, cyclooctynyl, cyclononynyl, cyclodecynyl, and the like.

The term "aryl" as used herein is intended to include carbocyclic aromatic ring systems such as phenyl, naphthyl (1-naphthyl or 2-naphthyl), anthracenyl(1-anthracenyl, 2-anthracenyl, 3-anthracenyl), phenanthrenyl, fluorenyl, indenyl, and the like. Aryl is also intended to include the partially hydrogenated derivatives of the carbocyclic systems enumerated above. Non-limiting examples of such partially hydrogenated derivatives are 1-(1,2,3,4-tetrahydronaphthyl) and 2-(1,2,3,4-tetrahydronaphthyl).

The term "aroyl" as used herein refers to the radical —CO-aryl where aryl is as defined above. Non-limiting examples are benzoyl, naphthoyl, anthracenoyl, phenanthrenoyl, fluorenoyl, indenoyl, and the like.

The term "aryloxy" as used herein refers to the radical —O-aryl where aryl is as defined above. Non-limiting examples are phenoxy, naphthoxy, anthracenyloxy, phenantrenyloxy, fluorenyloxy, indenyloxy, and the like.

The term "arylthio" as used herein refers to the radical —S-aryl where aryl is as defined above. Non-limiting examples are phenylthio, naphthylthio, phenanthrenylthio, fluorenylthio, indenylthio, and the like.

The term "arylamino" as used herein refers to the radical —NH-aryl where aryl is as defined above. Non-limiting examples are phenylamino, naphthylamino, phenanthrenylamino, fluorenylamino, indenylamino, and the like.

The term "arylsulfonyl" as used herein refers to the radical —S(=O)$_2$-aryl where aryl is as defined above. Non-limiting examples are phenylsulfonyl, naphthylsulfonyl, phenanthrenylsulfonyl, fluorenylsulfonyl, indenylsulfonyl, and the like.

The term "heteroaryl" as used herein is intended to include heterocyclic aromatic ring systems containing one or more heteroatoms selected from nitrogen, oxygen and sulfur, such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, benzothiophenyl(thianaphthenyl), indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl, and the like. Heteroaryl is also intended to include the partially or fully hydrogenated derivatives of the heterocyclic systems enumerated above. Non-limiting examples of such partially or fully hydrogenated derivatives are pyrrolinyl, pyrazolinyl, indolinyl, pyrrolidinyl, piperidinyl, piperazinyl, azepinyl, diazepinyl, morpholinyl, thiomorpholinyl, oxazolidinyl, oxazolinyl, oxazepinyl, aziridinyl and tetrahydofuranyl.

The term "heteroaroyl" as used herein refers to the radical —CO-heteroaryl where heteroaryl is as defined above. Non-limiting examples are furoyl, thienylcarbonyl, pyridoyl, oxazolylcarbonyl, benzofurylcarbonyl, benzimidazolylcarbonyl, pyrrolinylcarbonyl, azepinylcarbonyl, and the like.

The term "heteroaryloxy" as used herein refers to the radical —O-heteroaryl where heteroaryl is as defined above. Non-limiting examples are furyloxy, thienyloxy, pyridyloxy, oxazolyloxy, benzofuryloxy, benzimidazolyloxy, pyrrolinyloxy, azepinyloxy, and the like.

The term "heteroarylamino" as used herein refers to the radical —NH-heteroaryl where heteroaryl is as defined above. Non-limiting examples are furylamino, thienylamino, pyridylamino, oxazolylamino, benzofurylamino, benzimidazolylamino, pyrrolinylamino, azepinylamino, and the like.

The term "heteroarylthio" as used herein refers to the radical —S-heteroaryl where heteroaryl is as defined above.

Non-limiting examples are furylthio, thienylthio, pyridylthio, oxazolylthio, benzofurylthio, benzimidazolylthio, pyrrolinylthio, azepinylthio, and the like.

The term "heteroarylsulfonyl" as used herein refers to the radical —S(=O)$_2$-heteroaryl where heteroaryl is as defined above. Non-limiting examples are furylsulfonyl, thienylsulfonyl, pyridylsulfonyl, oxazolylsulfonyl, benzofurylsulfonyl, benzimidazolylsulfonyl, pyrrolinylsulfonyl, azepinylsulfony, and the like.

The term "acylamino" as used herein represents a radical of the form —N(L)—C(=O)—G where G and L independently represent hydrogen, $C_{1-6}$-alkyl, aryl or heteroaryl as defined above. Non-limiting examples are acetylamino, propanoylamino, butyrylamino, pentanoylamino, benzoylamino, furoylamino, pyridoylamino, and the like.

The term "sulfonylamino" as used herein represents a radical of the form —N(L)—S(=O)$_2$—G where G and L independently represent hydrogen, $C_{1-6}$-alkyl, aryl or heteroaryl as defined above. Non-limiting examples are methanesulfonylamino, propanesulfonylamino, benzenesulfonylamino, N-methyl-N-(benzenesulfonyl) amino, 4-methylbenzenesulfonylamino N-butyl-N-(4-methylbenzenesulfonyl)amino, 2-thienylsulfonylamino, and the like.

The term "halogen" means fluorine, chlorine, bromine or iodine.

As used herein, the phrase "3 to 8-membered, saturated or unsaturated, carbocyclic or heterocyclic ring" is intended to include carbocyclic rings which are saturated or contain one or more double bonds as well as heterocyclic rings containing one or more heteroatoms selected from nitrogen, oxygen or sulfur which are saturated or contain one or more double bonds.

Certain of the above defined terms may occur more than once in the structural formulas, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

As used herein, the phrase "a functional group which can be converted to hydrogen in vivo" is intended to include any group which upon administering the present compounds to the subjects in need thereof can be converted to hydrogen, e.g., enzymatically or by the acidic environment in the stomach. Non-limiting examples of such groups are acyl, carbamoyl, monoalkylated carbamoyl, dialkylated carbamoyl, alkoxycarbonyl, alkoxyalkyl groups, and the like, such as $C_{1-6}$-alkanoyl, aroyl, $C_{1-6}$-alkylcarbamoyl, di-$C_{1-6}$-alkylcarbamoyl, $C_{1-6}$-alkoxycarbonyl and $C_{1-6}$-alkoxy-$C_{1-6}$-alkyl.

As used herein, the phrase "diseases and disorders related to the histamine H3 receptor" is intended to include any disease or disorder in which an effect, either antagonistic or agonistic, on the histamine H3 receptor is beneficial.

DESCRIPTION OF THE INVENTION

The present invention relates to novel, substituted imidazoles of formula I

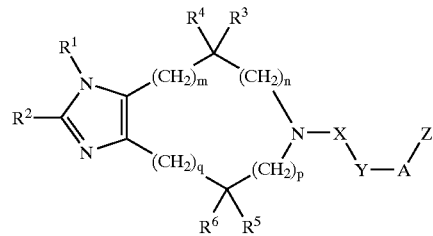

wherein
$R^1$ is hydrogen or a functional group, which can be converted to hydrogen in vivo;
$R^2$ is hydrogen, $C_{1-6}$-alkyl, halogen, cyano, trifluoromethyl, trifluoromethoxy, hydroxy or —$NR^7R^8$,
wherein $R^7$ and $R^8$ independently are
hydrogen,
$C_{1-6}$-alkyl optionally substituted with
aryl, heteroaryl, aroyl, heteroaroyl, arylsulfonyl, arylamino, heteroarylamino or $C_{3-8}$-cycloalkyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
aryl, heteroaryl, aroyl, heteroaroyl, arylsulfonyl or heteroarylsulfonyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
$C_{1-6}$-alkylsulfonyl optionally substituted with
$C_{3-8}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, or
$R^7$ and $R^8$, together with the nitrogen atom to which they are connected, form a 3 to 8-membered, saturated or unsaturated, heterocyclic ring optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;
$R^3$, $R^4$, $R^5$ and $R^6$ independently are
hydrogen, carboxy, $C_{1-6}$-alkoxycarbonyl, cyano, trifluoromethyl, halogen,
$C_{3-8}$-cycloalkyl optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
$C_{1-6}$-alkyl, $C_{2-6}$-alkenyl or $C_{2-6}$-alkynyl, which are optionally substituted with $C_{1-6}$-alkoxy, $C_{1-6}$-alkylthio, hydroxy, cyano, halogen, trifluoromethyl, trifluoromethoxy, carboxy, $C_{1-6}$-alkoxycarbonyl,
$C_{3-8}$-cycloalkyl, aryl, heteroaryl, aroyl, heteroaroyl, arylsulfonyl, arylamino or heteroarylamino, which are optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino, heteroarylamino or —CO—$NR^9R^{10}$, aryl optionally substituted with
  halogen, cyano, nitro, $C_{1-6}$-alkyl, $C_{1-6}$-alkoxy, hydroxy, trifluoromethyl, trifluoromethoxy, aryl, heteroaryl, aryloxy, aroyl, heteroaroyl, arylsulfonyl, arylamino, heteroarylamino or —CO—$NR^9R^{10}$,

—CO—$NR^9R^{10}$, wherein $R^9$ and $R^{10}$ independently are
  hydrogen,
  $C_{1-6}$-alkyl optionally substituted with
    aryl, heteroaryl, aroyl, heteroaroyl, arylsulfonyl, arylamino, heteroarylamino or $C_{3-8}$-cycloalkyl, which are optionally substituted with
      $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
    aryl, heteroaryl, aroyl, heteroaroyl, arylsulfonyl or heteroarylsulfonyl, which are optionally substituted with
      $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
  $C_{1-6}$-alkylsulfonyl optionally substituted with
    $C_{3-8}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, or
  $R^9$ and $R^{10}$, together with the nitrogen atom to which they are connected, form a 3 to 8-membered, saturated or unsaturated, heterocyclic ring optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, or $R^3$ and $R^4$, together with the carbon atom to which they are connected, and/or $R^5$ and $R^6$ together with the carbon atom to which they are connected, form a 3 to 8-membered, saturated or unsaturated, carbocyclic or heterocyclic ring optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;

m, n, p and q independently are 0, 1 or 2;

X is a valence bond, —$CH_2$—, —C(=O)—, —C(=S)—, —S(=O)—, —S(=O)$_2$—, —C(=N—CN)—, —C(=CH—$NO_2$)—, —C[=C(CN)$_2$]—, —C(=CH—CN)—, —C(=$NR^{11}$)— or —C(=N—S(=O)$_2R^{11a}$)—, wherein $R^{11}$ is
  hydrogen,
  $C_{1-6}$-alkyl optionally substituted with
    aryl, heteroaryl, aroyl, heteroaroyl, arylsulfonyl, arylamino, heteroarylamino or $C_{3-8}$-cycloalkyl, which are optionally substituted with
      $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
    aryl, heteroaryl, aroyl, heteroaroyl, arylsulfonyl or heteroarylsulfonyl, which are optionally substituted with
      $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
  $C_{1-6}$-alkylsulfonyl optionally substituted with
    $C_{1-6}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;

$R^{11a}$ is
  $C_{1-6}$-alkyl optionally substituted with
    aryl, heteroaryl, aroyl, heteroaroyl, arylsulfonyl, arylamino, heteroarylamino or $C_{3-8}$-cycloalkyl, which are optionally substituted with
      $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
    aryl, heteroaryl, aroyl, heteroaroyl, arylsulfonyl or heteroarylsulfonyl, which are optionally substituted with
      $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, Y is a valence bond, —O— or —$N(R^{12})$—, wherein $R^{12}$ is
  hydrogen,
  $C_{1-6}$-alkyl optionally substituted with
    aryl, heteroaryl, aroyl, heteroaroyl, arylsulfonyl, arylamino, heteroarylamino or $C_{3-8}$-cycloalkyl, which are optionally substituted with
      $C_{1-6}$-alkyl, $C_{1-6}$-alkoxy, $C_{1-6}$-alkylthio, hydroxy, amino, $C_{1-6}$-alkylamino, di($C_{1-6}$alkyl)amino, halogen, cyano, trifluoromethyl, trifluoromethoxy, aryl, heteroaryl, aroyl, heteroaroyl, arylsulfonyl, arylamino or heteroarylamino,
    aryl, heteroaryl, aroyl, heteroaroyl, arylsulfonyl or heteroarylsulfonyl, which are optionally substituted with
      $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
  $C_{1-6}$-alkylsulfonyl optionally substituted with
    $C_{3-8}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;

A is a valence bond, $C_{1-6}$-alkylene, $C_{2-8}$-alkenylene, $C_{2-8}$-alkynylene, $C_{3-8}$-cycloalkylene or phenylene, or when Y is —$N(R^{12})$—, A, together with $R^{12}$ and the nitrogen atom to which they are connected, may form a 3 to 8-membered, saturated or unsaturated, heterocyclic ring system optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aryl-$C_{1-6}$-alkyl, heteroaryl-$C_{1-6}$-alkyl, aroyl, heteroaroyl, arylsulfonyl, arylamino or heteroarylamino; and Z is —$R^{13}$, —$OR^{13}$, —$SR^{13}$, —$NR^{13}R^{14}$, —$CHR^{13}R^{14}$, —$CR^{13}R^{14}R^{15}$ or =$CR^{13}R^{14}$, wherein $R^{13}$, $R^{14}$ and $R^{15}$ independently are hydrogen, $C_{1-6}$-alkyl, $C_{2-6}$-alkenyl or $C_{2-6}$-alkynyl, which are optionally substituted with aryl, arylamino, heteroarylamino, aroyl, heteroaroyl, arylsulfonyl, $C_{1-6}$-alkylsulfonyl, sulfonylamino, arylthio, heteroarylthio, aryloxy, acylamino, heteroaryl or $C_{3-8}$-cycloalkyl, which are optionally substituted with $C_{1-6}$-alkyl, $C_{1-6}$-alkoxy, $C_{1-6}$-alkylthio, aryl-$C_{1-6}$-alkyl, heteroaryl-$C_{1-6}$-alkyl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, hydroxy, amino, $C_{1-6}$-alkylamino, di($C_{1-6}$-alkyl)amino, halogen, cyano, trifluoromethoxy or trifluoromethyl, aryl, $C_{3-15}$-cycloalkyl, $C_{3-15}$-cycloalkenyl, $C_{3-15}$-cycloalkynyl, aroyl or heteroaryl, which are optionally substituted with aryl-$C_{1-6}$-alkyl, heteroaryl-$C_{1-6}$-alkyl, aryl, heteroaryl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, $C_{1-6}$-alkyl, $C_{1-6}$-alkoxy, $C_{1-6}$-alkylthio, $C_{3-8}$-cycloalkanecarbonyl, hydroxy, amino, $C_{1-6}$-alkylamino, di($C_{1-6}$-alkyl)amino, halogen, cyano, trifluoromethoxy or trifluoromethyl, where $R^{13}$ and $R^{14}$ or $R^{13}$, $R^{14}$ and $R^{15}$, when they do not represent hydrogen, may be joined by one or more bridging linkers such as a valence bond, $C_{1-4}$-alkylene, $C_{2-4}$-alkenylene, —O—, —S—, —N($R^{16}$)—, —C(=O)—, —S(=O)—, —S(=O)$_2$—, —C($R^{16}R^{17}$)—, phenylene, biphenylene, —O—$C_{1-4}$-alkylene, —S—$C_{1-4}$-alkylene, —N($R^{16}$)—$C_{1-4}$-alkylene, —N=$C_{1-4}$-alkylene, —O—$C_{2-4}$-alkenylene, —S—$C_{2-4}$-alkenylene or —N($R^{16}$)—$C_{2-4}$-alkenylene, to form a mono-, bi- or polycyclic ring system, wherein $R^{16}$ and $R^{17}$ independently are hydrogen, $C_{1-6}$-alkyl optionally substituted with aryl, heteroaryl, aroyl, heteroaroyl, arylsulfonyl, arylamino, heteroarylamino or $C_{3-8}$-cycloalkyl, which are optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, $C_{1-6}$-alkylsulfonyl optionally substituted with $C_{3-8}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, or $R^{16}$ and $R^{17}$, together with the nitrogen atom to which they are connected, form a 3 to 8-membered, saturated or unsaturated, heterocyclic ring optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;

provided that when X is —CS—, $R^1=R^2=R^5=R^6$=hydrogen, m=n=p=0 and q=1, the group —Y—A—Z must not start with the radical —NH—;

when the group —X—Y—A—Z starts with the radical —$CH_2$—, $R^1=R^2=R^6$=hydrogen, m=n=p=0 and q=1, $R^5$ must not be carboxy or aminocarbonyl;

when X is —CO—, the group —Y—A—Z starts with the radical —NH—, $R^1=R^2=R^6$=hydrogen, m=n=p=0 and q=1, the remainder of the group —Y—A—Z must not be hydrogen, unsubstituted or $C_{1-6}$-alkoxy substituted phenyl, unsubstituted $C_{3-8}$-cycloalkyl or unsubstituted $C_{1-6}$-alkyl;

when X is —CO—, Y is —O—, A is —$CH_2$—, Z is phenyl, $R^1=R^2=R^3=R^4=R^6$=hydrogen, m=n=p=0 and q=1, $R^5$ must not be carboxy, aminocarbonyl or 4-phenylpiperazin-1-ylcarbonyl;

when X is —CO—, Y is —O—, A is —$CH_2$—, Z is phenyl, $R^1=R^3=R^4=R^6$=hydrogen, $R^2$=butyl, m=n=p=0 and q=1, $R^5$ must not be methoxycarbonyl;

when X is —CO—, Y is —O—, A is —$CH_2$—, Z is phenyl, $R^1=R^2=R^4=R^5=R^6$=hydrogen, m=n=p=0 and q=1, $R^3$ must not be hydrogen, ethyl, isopropyl or phenyl;

when X is —CO—, Y is —O—, A is a valence bond, Z is tert-butyl, $R^1=R^2=R^3=R^4=R^6$=hydrogen, m=n=p=0 and q=1, $R^5$ must not be carboxy;

when X is —CO—, Y is —O—, A is a valence bond, Z is tert-butyl, $R^1=R^2=R^4=R^5=R^6$=hydrogen, m=n=p=0 and q=1, $R^3$ must not be 4-cyanophenyl;

when X is —CO—, the group —Y—A—Z starts with the radical —O—, $R^1=R^2=R^6$=hydrogen, m=n=p=0 and q=1, $R^5$ must not be carboxy, aminocarbonyl or hydrogen;

when —X is —CO—, the group —Y—A—Z starts with the radical —CH<, $R^1=R^2=R^3=R^4=R^6$=hydrogen, m=n=p=0 and q=1, $R^5$ must not be hydroxymethyl, $C_{1-6}$-alkoxycarbonyl or carboxy; and when X is —CO—, the group —Y—A—Z is 4-methoxyphenyl, $R^1=R^2=R^3=R^4=R^6$=hydrogen, m=n=p=0 and q=1, $R^5$ must not be carboxy;

as well as any optical or geometric isomer or tautomeric form thereof, including mixtures of these, or a pharmaceutically acceptable salt thereof.

Preferably, $R^1=R^2$=hydrogen.

In a preferred embodiment m=n=p=0, and q=1.

In another preferred embodiment n=p=0, and m=q=1.

Preferably, X is a valence bond, —C(=O)—, —S(=O)$_2$—, —C(=N—CN)—, —C(=CH—NO$_2$)— or —C(=N—S(=O)$_2$R$^{11a}$)—, wherein R$^{11a}$ is as defined for formula I above.

More preferably, X is preferably —C(=O)—.

Preferably, A is a valence bond, C$_{1-8}$-alkylene, C$_{2-8}$-alkenylene or C$_{2-8}$-alkynylene.

More preferably, A is a valence bond or C$_{1-8}$-alkylene, such as methylene, ethylene or propylene.

Preferably, Z is —R$^{13}$, —NR$^{13}$R$^{14}$, —CHR$^{13}$R$^{14}$ or —CR$^{13}$R$^{14}$R$^{15}$, wherein R$^{13}$, R$^{14}$ and R$^{15}$ are as defined for formula I above.

In a preferred embodiment Z is —R$^{13}$, wherein R$^{13}$ is as defined for formula I above.

Of these Z is preferably C$_{1-6}$-alkyl, aryl, C$_{3-15}$-cycloalkyl, C$_{3-15}$-cycloalkenyl, aroyl or heteroaryl, which are optionally substituted as defined for formula I above.

More preferably, Z is C$_{1-6}$-alkyl, phenyl, naphthyl, thienyl, cyclopentyl, cyclohexyl, cyclohexenyl, oxazolyl, indanyl, isoquinolyl, benzoyl or tetrahydronaphthyl, which are optionally substituted for formula I above.

Even more preferably, Z is phenyl or cyclohexyl, which are optionally substituted as defined for formula I above.

Z may be unsubstituted or substituted with one to three substituents selected from C$_{1-6}$-alkyl, C$_{1-6}$-alkoxy, halogen, phenyl, di(C$_{1-6}$-alkyl)amino, C$_{3-8}$-cyclopropanecarbonyl, trifluoromethoxy and trifluoromethyl.

In another preferred embodiment Z is —NR$^{13}$R$^{14}$, in which R$^{13}$ and R$^{14}$ are both phenyl, which phenyl groups are joined with a C$_{1-4}$-alkylene group to form a tricyclic ring system, such as 10,11-dihydro-5H-dibenzo[b,f]azepin-5-yl.

In yet another preferred embodiment Z is —CHR$^{13}$R$^{14}$, in which R$^{13}$ is C$_{1-6}$-alkyl or phenyl and R$^{14}$ is phenyl, or R$^{13}$ and R$^{14}$ are both C$_{1-6}$-alkyl, which are joined with C$_{1-4}$-alkylene linkers to form a polycarbocyclic ring system, such as bicyclo[2.2.1]hept-2-yl.

In a further preferred embodiment Z is —CR$^{13}$R$^{14}$R$^{15}$, in which R$^{13}$, R$^{14}$ and R$^{15}$ are C$_{1-6}$-alkyl, which are joined with C$_{1-4}$-alkylene linkers to form a polycarbocyclic ring system, such as adamantyl.

Preferably, R$^3$ and R$^4$ are independently
hydrogen;
C$_{3-8}$-cycloalkyl optionally substituted with C$_{1-6}$-alkyl, C$_{1-6}$-alkoxy, C$_{1-6}$-alkylthio, hydroxy, amino, C$_{1-6}$-alkylamino, di(C$_{1-6}$-alkylamino), halogen, cyano, trifluoromethyl, trifluoromethoxy, aryl, heteroaryl, aroyl, heteroaroyl, arylsulfonyl, arylamino or heteroarylamino,
C$_{1-6}$-alkyl optionally substituted with
C$_{3-8}$-cycloalkyl, aryl, heteroaryl, aroyl, heteroaroyl, arylsulfonyl, arylamino or heteroarylamino which are optionally substituted with
C$_{1-6}$-alkyl, C$_{1-6}$-alkoxy, C$_{1-6}$-alkylthio, hydroxy, amino, C$_{1-6}$-alkylamino, di(C$_{1-6}$-alkylamino), halogen, cyano, trifluoromethyl, trifluoromethoxy, aryl, heteroaryl, aroyl, heteroaroyl, arylsulfonyl, arylamino or heteroarylamino,
aryl optionally substituted with
halogen, cyano, nitro, C$_{1-6}$-alkyl, C$_{1-6}$-alkoxy, hydroxy, trifluoromethyl, trifluoromethoxy, aryl, heteroaryl, aryloxy, aroyl, heteroaroyl, arylsulfonyl, arylamino, heteroarylamino or —CO—NR$^9$R$^{10}$, wherein R$^9$ and R$^{10}$ are as defined in claim 1, or
R$^3$ and R$^4$, together with the carbon atom to which they are connected, form a C$_{3-8}$-cycloalkyl ring optionally substituted with C$_{1-6}$-alkyl, C$_{1-6}$-alkoxy, C$_{1-6}$-alkylthio, hydroxy, amino, C$_{1-6}$-alkylamino, di(C$_{1-6}$-alkylamino), halogen, cyano, trifluoromethyl, trifluoromethoxy, aryl, heteroaryl, aroyl, heteroaroyl, arylsulfonyl, arylamino or heteroarylamino.

More preferably, R$^3$ and R$^4$ are both hydrogen or are both C$_{1-6}$-alkyl, or R$^3$ and R$^4$, together with the carbon atom to which they are connected, form a C$_{3-8}$-cycloalkyl ring, or one of R$^3$ and R$^4$ is hydrogen while the other is C$_{3-8}$-cycloalkyl substituted C$_{1-6}$-alkyl.

Preferably, R$^5$ and R$^6$ are both hydrogen.

In a preferred embodiment R$^3$, R$^4$, R$^5$ and R$^6$ are hydrogen.

In a preferred embodiment m=n=p=0, and q=1, or n=p=0, and m=q=1; R$^1$=R$^2$=hydrogen; R$^3$, R$^4$, R$^5$ and R$^6$ are hydrogen; X is —C(=O)—; Y is —N(R$^{12}$)—, wherein R$^{12}$ and A, together with the nitrogen atom to which they are connected, form a 3 to 8 membered, saturated or unsaturated, heterocyclic ring system optionally containing one or more further heteroatoms selected from nitrogen, oxygen and sulfur, and optionally substituted with C$_{1-6}$-alkyl, C$_{1-6}$-alkoxy, C$_{1-6}$-alkylthio, hydroxy, amino, C$_{1-6}$-alkylamino, di(C$_{1-6}$-alkylamino), halogen, cyano, trifluoromethyl, trifluoromethoxy, aryl, heteroaryl, aryl-C$_{1-6}$-alkyl, heteroaryl-C$_{1-6}$-alkyl, aroyl, heteroaroyl, arylsulfonyl, arylamino or heteroarylamino; and Z is —R$^{13}$, wherein R$^{13}$ is hydrogen.

In another preferred embodiment m=n=p=0, and q=1, or n=p=0, and m=q=1; R$^1$=R$^2$=hydrogen; R$^3$, R$^4$, R$^5$ and R$^6$ are hydrogen; X is —C(=N—CN)—, —C(=CH—NO$_2$)— or —C(=N—S(=O)$_2$R$^{11a}$)—, wherein R$^{11a}$ is C$_{1-6}$-alkyl or phenyl substituted with C$_{1-6}$-alkyl; Y is —NH—; A is C$_{1-8}$-alkylene; and Z is —R$^{13}$, wherein R$^{13}$ is C$_{1-6}$-alkyl, aryl, C$_{3-15}$-cycloalkyl, C$_{3-15}$-cycloalkenyl, aroyl or heteroaryl, which are optionally substituted as defined for formula I above.

In yet another preferred embodiment m=n=p=0, and q=1, or n=p=0, and m=q=1; R$^1$=R$^2$=hydrogen; R$^3$, R$^4$, R$^5$ and R$^6$ are hydrogen; X is —S(=O)$_2$—; Y is a valence bond; A is a valence bond or C$_{1-8}$-alkylene; and Z is —R$^{13}$, wherein R$^{13}$ is C$_{1-6}$-alkyl, aryl, C$_{3-15}$-cycloalkyl, C$_{3-15}$-cycloalkenyl, aroyl or heteroaryl, which are optionally substituted as defined for formula I above.

In still another preferred embodiment m=n=p=0, and q=1, or n=p=0, and m=q=1; R$^1$=R$^2$=hydrogen; R$^3$, R$^4$, R$^5$ and R$^6$ are hydrogen; X is —C(=O)—; Y is —N(R$^{12}$)—, wherein R$^{12}$ is hydrogen or C$_{1-6}$-alkyl; A is a valence bond or C$_{1-8}$-alkylene; and Z is —R$^{13}$, wherein R$^{13}$ is C$_{1-6}$alkyl, aryl, C$_{3-15}$-cycloalkyl, C$_{3-15}$-cycloalkenyl, aroyl or heteroaryl, which are optionally substituted as defined for formula I above.

In a further preferred embodiment m=n=p=0, and q=1, or n=p=0, and m=q=1; R$^1$=R$^2$=hydrogen; R$^3$, R$^4$, R$^5$ and R$^6$ are hydrogen; X is —C(=O)—; Y is —O—; A is a valence bond or C$_{1-8}$-alkylene; and Z is —R$^{13}$, wherein R$^{13}$ is C$_{1-6}$-alkyl, aryl, C$_{3-15}$-cycloalkyl, C$_{3-15}$-cycloalkenyl, aroyl or heteroaryl, which are optionally substituted as defined for formula I above.

In yet a further preferred embodiment m=n=p=0, and q=1, or n=p=0, and m=q=1; R$^1$=R$^2$=hydrogen; R$^3$, R$^4$, R$^5$ and R$^6$ are hydrogen; X is —C(=O)—; Y is a valence bond; A is a valence bond or C$_{1-8}$-alkylene; and Z is —R$^{13}$, wherein R$^{13}$ is C$_{1-6}$-alkyl, aryl, C$_{3-15}$-cycloalkyl, C$_{3-15}$-cycloalkenyl, aroyl or heteroaryl, which are optionally substituted as defined for formula I above.

More preferably, Z is C$_{1-6}$-alkyl, phenyl, naphthyl, thienyl, cyclopentyl, cyclohexyl, cyclohexenyl, oxazolyl, indanyl, isoquinolyl, benzoyl or tetrahydronaphthyl, which are optionally substituted as defined for formula I above.

Even more preferably, Z is phenyl or cyclohexyl which are optionally substituted as defined for formula I above.

Z may be unsubstituted or substituted with one to three substituents selected from $C_{1-6}$-alkyl, $C_{1-6}$-alkoxy, halogen, phenyl, di($C_{1-6}$-alkyl)amino, $C_{3-8}$-cyclopropanecarbonyl, trifluoromethoxy and trifluoromethyl.

Specific examples of the above-preferred embodiments of the present invention are the following compounds:

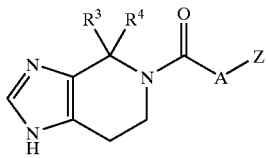

wherein

| $R^3$ | $R^4$ | A | Z |
|---|---|---|---|
| H | H | methylene | cyclohexyl |
| H | H | ethylene | 4-fluorobenzoyl |
| H | H | bond | cyclohexyl |
| H | H | pentylene | benzoyl |
| H | H | ethylene | cyclohexyl |
| H | H | pentylene | phenyl |
| H | H | butylene | cyclohexyl |
| H | H | bond | methyl |
| H | H | methylene | diphenylmethyl |
| H | H | ethylene | 10,11-dihydro-5H-dibenzo[b,f]azepin-5-yl |
| $CH_3$ | $CH_3$ | ethylene | cyclohexyl |
| H | 4-isopropylphenyl | ethylene | 4-fluorophenyl |
| $CH_3$ | $CH_2CH_3$ | ethylene | cyclohexyl |
| spiro- | —$(CH_2)_3$— | ethylene | cyclohexyl |
| H | H | bond | 3,4-dihydro-1H-isoquinolin-2-yl |
| H | H | methylene | tert-butyl |
| H | H | ethynylene | phenyl |
| H | H | ethenylene | 4-tert-butylphenyl |
| H | H | methylene | bicyclo[2.2.1]hept-2-yl |
| H | H | bond | 4-pentylphenyl |
| H | H | bond | 4-trifluoromethoxyphenyl |
| H | H | bond | 4-trifluoromethylphenyl |
| H | H | bond | 4-isobutylphenyl |
| H | H | bond | 4-chlorophenyl | as well as any optical or geometric isomer or tautomeric form thereof, including mixtures of these, or a pharmaceutically acceptable salt thereof.

Specific examples of the above-preferred embodiments of the present invention are the following compounds:

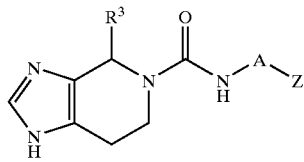

wherein

| $R^3$ | A | Z |
|---|---|---|
| H | —$(CH_2)_2$— | 2-thienyl |
| H | bond | 3,5-dimethyl-1,2-oxazol-4-yl |
| H | —$CH(CH_3)$— | 1-naphthyl |
| H | bond | 2-phenylcyclopropyl |
| H | bond | 1-(4-bromophenyl)ethyl |
| H | bond | 2-(trifluorometnyl)phenyl |
| H | ethylene | phenyl |

| $R^3$ | A | Z |
|---|---|---|
| H | bond | 4-(trifluoromethyl)phenyl |
| H | bond | 3-cyanophenyl |
| H | bond | 4-cyanophenyl |
| H | bond | n-octyl |
| H | methylene | 2,4-dichlorophenyl |
| 2-cyclohexylethyl | bond | ethyl |
| 2-cyclohexylethyl | methylene | 2,4-dichlorophenyl | as well as any optical or geometric isomer or tautomeric form thereof, including mixtures of these, or a pharmaceutically acceptable salt thereof.

Specific examples of the above-preferred embodiments of the present invention are the following compounds:

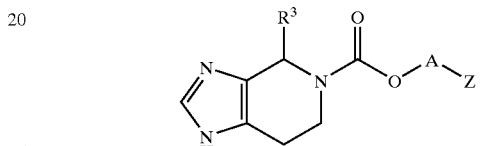

wherein

| $R^3$ | A | Z |
|---|---|---|
| H | —$CH_2$— | ![4-tert-butylphenyl structure] |
| H | —$CH_2$— | ![phenyl structure] |
| H | —$CH_2$— | ![2,6-dimethylphenyl structure] |
| H | —$CH_2$— | ![1-phenylpropyl structure] |
| H | —$CH_2$— | ![3-methoxyphenyl structure] |
| H | —$CH_2$— | ![cyclopentyl structure] |

| R³ | A | Z |
|---|---|---|
| H | —CH₂— | 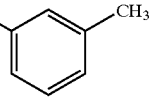 |
| H | —CH₂— | 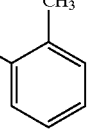 |
| H | —(CH₂)₂— | 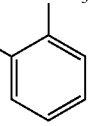 |
| H | —(CH₂)₂— | 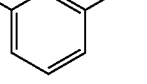 |
| H | —CH₂— |  |
| H | —CH₂— | 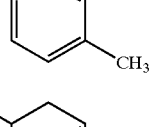 |
| H | —CH₂— |  |
| H | —CH₂— | 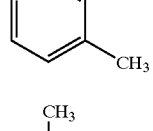 |
| H | —(CH₂)₂— |  |
| H | —CH₂— | 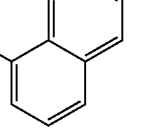 |
| H | —CH₂— | 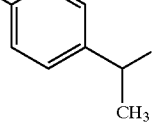 |
| R³ | A | Z |
|---|---|---|
| H | —CH₂— |  |
| H | —CH₂— | 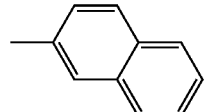 |
| H | —CH₂— | 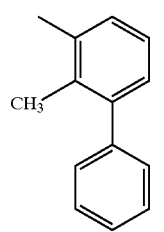 |
| H | —CH₂— | 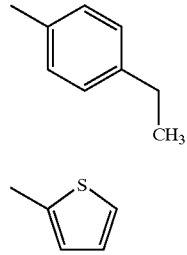 |
| H | —(CH₂)₂— | 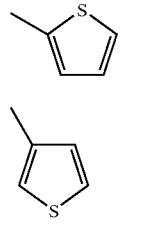 |
| H | —(CH₂)₂— | 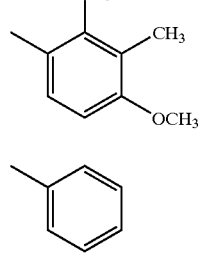 |
| H | —CH₂— | 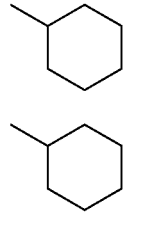 |
| —CF₃ | —CH₂— | 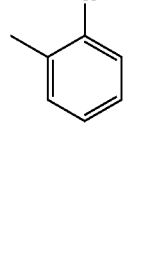 |
| H | —(CH₂)₂— |  |
| H | —CH₂— |  |
| H | —CH₂— |  |

-continued

| R³ | A | Z |
|---|---|---|
| H | —CH₂— | 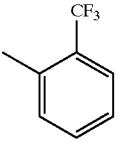 |
| H | bond | 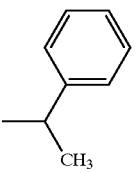 | as well as any optical or geometric isomer or tautomeric form thereof, including mixtures of these, or a pharmaceutically acceptable salt thereof.

In a further aspect the invention relates to novel, substituted imidazoles of formula I''

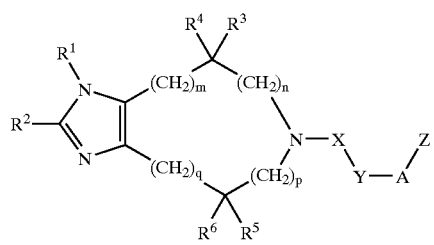

wherein $R^1$ is hydrogen or a functional group which can be converted to hydrogen in vivo;

$R^2$ is hydrogen, $C_{1-6}$-alkyl, halogen, cyano, trifluoromethyl, hydroxy or —NR⁷R⁸, wherein $R^7$ and $R^8$ independently are hydrogen, $C_{1-6}$-alkyl optionally substituted with
aryl, heteroaryl, aroyl, heteroaroyl, arylsulfonyl, arylamino, heteroarylamino or $C_{3-8}$-cycloalkyl, which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with
$C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, $C_{1-6}$-alkylsulfonyl optionally substituted with
$C_{3-8}$-cycloalkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, or $R^7$ and $R^8$, together with the nitrogen atom to which they are connected, form a 3 to 8-membered, saturated or unsaturated, heterocyclic ring optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

$R^3$, $R^4$, $R^5$ and $R^6$ independently are hydrogen, carboxy, $C_{1-6}$-alkoxycarbonyl, cyano, trifluoromethyl, halogen, $C_{3-8}$-cycloalkyl optionally substituted with
$C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, $C_{1-6}$-alkyl, $C_{2-6}$-alkenyl or $C_{2-6}$-alkynyl, which are optionally substituted with
$C_{1-6}$-alkoxy, $C_{1-6}$-alkylthio, hydroxy, cyano, halogen, trifluoromethyl, carboxy, $C_{1-6}$-alkoxycarbonyl,
$C_{3-8}$-cycloalkyl, aryl, heteroaryl, aroyl, heteroaroyl, arylsulfonyl, arylamino or heteroarylamino, which are optionally substituted with
$C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino, heteroarylamino or —CO—NR⁹R¹⁰, aryl optionally substituted with
halogen, cyano, nitro, $C_{1-6}$-alkyl, $C_{1-6}$-alkoxy, hydroxy, trifluoromethyl, aryl, heteroaryl, aryloxy, aroyl, heteroaroyl, arylsulfonyl, arylamino, heteroarylamino or —CO—NR⁹R¹⁰,

—CO—NR⁹R¹⁰, wherein $R^9$ and $R^{10}$ independently are hydrogen, $C_{1-6}$-alkyl optionally substituted with
aryl, heteroaryl, aroyl, heteroaroyl, arylsulfonyl, arylamino, heteroarylamino or $C_{3-8}$-cycloalkyl, which are optionally substituted with
$C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with
$C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, $C_{1-6}$-alkylsulfonyl optionally substituted with
$C_{3-8}$-cycloalkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, or $R^9$ and $R^{10}$, together with the nitrogen atom to which they are connected, form a 3 to 8 membered, saturated or unsaturated, heterocyclic ring optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, or $R^3$ and $R^4$, together with the carbon atom to which they are connected, and/or $R^5$ and $R^6$ together with the carbon atom to which they are connected, form a 3 to 8 membered, saturated or unsaturated, carbocyclic or heterocyclic ring optionally substituted with $C_{1-6}$-alkyl, $C_{1-6}$- alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

m, n, p and q independently are 0, 1 or 2;

X is a valence bond, —$CH_2$—, —$C(=O)$—, —$C(=S)$—, —$S(=O)$—, —$S(=O)_2$—, —$C(=N—CN)$—, —$C(=CH—NO_2)$—, —$C[=C(CN_2)]$—, —$C(=CH—CN)$— or —$C(=NR^{11})$—, wherein $R^{11}$ is hydrogen, $C_{1-6}$-alkyl optionally substituted with aryl, heteroaryl, aroyl, heteroaroyl, arylsulfonyl, arylamino, heteroarylamino or $C_{3-8}$-cycloalkyl, which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, $C_{1-6}$-alkylsulfonyl optionally substituted with $C_{3-8}$-cycloalkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

Y is a valence bond, —O— or —$N(R^{12})$—, wherein $R^{12}$ is hydrogen, $C_{1-6}$-alkyl optionally substituted with aryl, heteroaryl, aroyl, heteroaroyl, arylsulfonyl, arylamino, heteroarylamino or $C_{3-8}$-cycloalkyl, which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, $C_{1-6}$-alkylsulfonyl optionally substituted with $C_{3-8}$-cycloalkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

A is a valence bond, $C_{1-8}$-alkylene, $C_{2-8}$-alkenylene, $C_{2-8}$-alkynylene, $C_{3-8}$-cycloalkylene or phenylene, or when Y is —$N(R^{12})$—, A, together with $R^{12}$ and the nitrogen atom to which they are connected, may form a 3 to 8 membered, saturated or unsaturated, heterocyclic ring system optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aryl-$C_{1-6}$-alkyl, heteroaryl-$C_{1-6}$-alkyl, aroyl, heteroaroyl, arylsulfonyl, arylamino or heteroarylamino; and Z is —$R^{13}$, —$OR^{13}$, —$SR^{13}$, —$NR^{13}R^{14}$, —$CHR^{13}R^{14}$, —$CR^{13}R^{14}R^{15}$ or =$CR^{13}R^{14}$, wherein $R^{13}$, $R^{14}$ and $R^{15}$ independently are hydrogen, $C_{1-6}$-alkyl, $C_{2-6}$-alkenyl or $C_{2-6}$-alkynyl, which are optionally substituted with aryl, arylamino, heteroarylamino, aroyl, heteroaroyl, arylsulfonyl, $C_{1-6}$-alkylsulfonyl, sulfonylamino, arylthio, heteroarylthio, aryloxy, acylamino, heteroaryl or $C_{3-8}$-cycloalkyl, which are optionally substituted with $C_{1-6}$-alkyl, $C_{1-6}$-alkoxy, $C_{1-6}$-alkylthio, aryl-$C_{1-6}$-alkyl, heteroaryl-$C_{1-6}$-alkyl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, hydroxy, amino, halogen, cyano or trifluoromethyl, aryl, $C_{3-15}$-cycloalkyl, aroyl or heteroaryl, which are optionally substituted with aryl-$C_{1-6}$-alkyl, heteroaryl-$C_{1-6}$-alkyl, aryl, heteroaryl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, $C_{1-6}$-alkyl, $C_{1-6}$-alkoxy, $C_{1-6}$-alkylthio, hydroxy, amino, halogen, cyano or trifluoromethyl, where $R^{13}$ and $R^{14}$ or $R^{13}$, $R^{14}$ and $R^{15}$, when they do not represent hydrogen, may be joined by one or more bridging linkers such as a valence bond, $C_{1-4}$-alkylene, $C_{2-4}$-alkenylene, —O—, —S—, —$N(R^{16})$—, —$C(=O)$—, —$S(=O)$—, —$S(=O)_2$—, —$C(R^{16}R^{17})$—, phenylene, biphenylene, —O—$C_{1-4}$-alkylene, —S—$C_{1-4}$-alkylene, —$N(R^{16})$—$C_{1-4}$-alkylene, —N=$C_{1-4}$-alkylene, —O—$C_{2-4}$-alkenylene, —S—$C_{2-4}$-alkenylene or —$N(R^{16})$—$C_{2-4}$-alkenylene, to form a mono-, bi- or polycyclic ring system, wherein $R^{16}$ and $R^{17}$ independently are hydrogen, $C_{1-6}$-alkyl optionally substituted with aryl, heteroaryl, aroyl, heteroaroyl, arylsulfonyl, arylamino, heteroarylamino or $C_{3-8}$-cycloalkyl, which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, $C_{1-6}$-alkylsulfonyl optionally substituted with $C_{3-8}$-cycloalkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino, or $R^{16}$ and $R^{17}$, together with the nitrogen atom to which they are connected, form a 3 to 8 membered, saturated or unsaturated, heterocyclic ring optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

provided that when X is —CS—, $R^1=R^2=R^5=R^6$=hydrogen, m=n=p=0 and q=1, the group —Y—A—Z must not start with the radical —NH—;

when the group —X—Y—A—Z starts with the radical —CH$_2$—, $R^1=R^2=R^6$=hydrogen, m=n=p=0 and q=1, $R^5$ must not be carboxy or aminocarbonyl;

when X is —CO—, the group —Y—A—Z starts with the radical —NH—, $R^1=R^2=R^6$=hydrogen, m=n=p=0 and q=1, the remainder of the group —Y—A—Z must not be hydrogen, unsubstituted or $C_{1-6}$-alkoxy substituted phenyl, unsubstituted $C_{3-8}$-cycloalkyl or unsubstituted $C_{1-6}$-alkyl;

when is —CO—, Y is —O—, A is —CH$_2$—, Z is phenyl, $R^1=R^2=R^3=R^4=R^6$=hydrogen, m=n=p=0 and q=1, $R^5$ must not be carboxy, aminocarbonyl or 4-phenylpiperazin-1-ylcarbonyl;

when X is —CO—, Y is —O—, A is —CH$_2$—, Z is phenyl, $R^1=R^3=R^4=R^6$=hydrogen, $R^2$=butyl, m=n=p=0 and q=1, $R^5$ must not be methoxycarbonyl;

when X is —CO—, Y is —O—, A is —CH$_2$—, Z is phenyl, $R^1=R^2=R^4=R^5=R^6$=hydrogen, m=n=p=0 and q=1, $R^3$ must not be hydrogen, ethyl, isopropyl or phenyl;

when X is —CO—, Y is —O—, A is a valence bond, Z is tert-butyl, $R^1=R^2=R^3=R^4=R^6$=hydrogen, m=n=p=0 and q=1, $R^5$ must not be carboxy;

when X is —CO—, Y is —O—, A is a valence bond, Z is tert-butyl, $R^1=R^2=R^4=R^5=R^6$=hydrogen, m=n=p=0 and q=1, $R^3$ must not be 4-cyanophenyl;

when X is —CO—, the group —Y—A—Z starts with the radical —O—, $R^1=R^2=R^6$=hydrogen, m=n=p=0 and q=1, $R^5$ must not be carboxy, aminocarbonyl or hydrogen;

when —X is —CO—, the group —Y—A—Z starts with the radical —CH<, $R^1=R^2=R^3=R^4=R^6$=hydrogen, m=n=p=0 and q=1, $R^5$ must not be hydroxymethyl, $C_{1-6}$-alkoxycarbonyl or carboxy; and when X is —CO—, the group —Y—A—Z is 4-methoxyphenyl, $R^1=R^2=R^3=R^4=R^6$=hydrogen, m=n=p=0 and q=1, $R^5$ must not be carboxy;

as well as any optical or geometric isomer or tautomeric form thereof, including mixtures of these, or a pharmaceutically acceptable salt thereof.

In a further aspect the invention relates to novel, substituted imidazoles of formula I'''

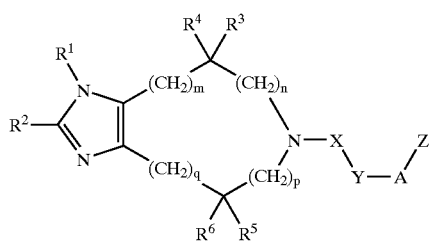

wherein $R^1$ is hydrogen or a functional group which can be converted to hydrogen in vivo;

$R^2$ is hydrogen, $C_{1-6}$-alkyl, halogen, cyano, trifluoromethyl, hydroxy or —NR$^7$R$^8$ wherein $R^7$ and $R^8$ independently are hydrogen;

$C_{1-6}$-alkyl optionally substituted with aryl, heteroaryl, aroyl, heteroaroyl, arylsulfonyl, arylamino, heteroarylamino or $C_{3-8}$-cycloalkyl which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

aryl optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

heteroaryl optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

aroyl optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

heteroaroyl optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

arylsulfonyl optionally substituted with $C_{1-6}$-alkyl, $C_{1-6}$—$C_{1-6}$alkoxy, $C_{1-6}$alkylthio, hydroxy, amino, halogen, cyano, trifluoromethyl, aryl, heteroaryl, aroyl, heteroaroyl, arylsulfonyl, arylamino or heteroarylamino;

heteroarylsulfonyl optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino; or $C_{1-6}$-alkylsulfonyl optionally substituted with $C_{3-8}$-cycloalkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino; or $R^7$ and $R^8$, together with the nitrogen atom to which they are connected, form a 3 to 8 membered, saturated or unsaturated, carbocyclic or heterocyclic ring optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

$R^3$, $R^4$, $R^5$ and $R^6$ independently are hydrogen; carboxy; $C_{1-6}$-alkoxycarbonyl; —CO—NR$^7$R$^8$ wherein $R^7$ and $R^8$ are as defined above; cyano; or halogen;

$C_{3-8}$-cycloalkyl optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

$C_{1-6}$-alkyl optionally substituted with $C_{1-6}$alkoxy; $C_{1-6}$-alkylthio; hydroxy; cyano; halogen; trifluoromethyl; carboxy; $C_{1-6}$-alkoxycarbonyl; or —CO—NR$^7$R$^8$ wherein $R^7$ and $R^8$ are as defined above; or $C_{3-8}$-cycloalkyl, aryl, heteroaryl, aroyl, heteroaroyl, arylsulfonyl, arylamino or heteroarylamino which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

$C_{2-6}$-alkenyl optionally substituted with $C_{1-6}$-alkoxy; $C_{1-6}$-alkylthio; hydroxy; cyano; halogen; trifluoromethyl; carboxy; $C_{1-6}$-alkoxycarbonyl; or —CO—NR$^7$R$^8$ wherein $R^7$ and $R^8$ are as defined above; or $C_{3-8}$-cycloalkyl, aryl, heteroaryl, aroyl, heteroaroyl, arylsulfonyl, arylamino or heteroarylamino which are optionally substituted with $C_{1-6}$- alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino;

$C_{2-6}$-alkynyl optionally substituted with
  $C_{1-6}$-alkoxy; $C_{1-6}$-alkylthio; hydroxy; cyano; halogen; trifluoromethyl; carboxy; $C_{1-6}$-alkoxycarbonyl; or —CO—NR$^7$R$^8$ wherein R$^7$ and R$^8$ are as defined above; or $C_{3-8}$-cycloalkyl, aryl, heteroaryl, aroyl, heteroaroyl, arylsulfonyl, arylamino or heteroarylamino which are optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino; or aryl optionally substituted with halogen, cyano, nitro, $C_{1-6}$-alkyl, $C_{1-6}$-alkoxy, hydroxy, trifluoromethyl, aryl, heteroaryl, aryloxy, aroyl, heteroaroyl, arylsulfonyl, arylamino, heteroarylamino or —CO—NR$^7$R$^8$ wherein R$^7$ and R$^8$ are as defined above; or R$^3$ and R$^4$, together with the carbon atom to which they are connected, and/or R$^5$ and R$^6$ together with the carbon atom to which they are connected, form a 3 to 8 membered, saturated or unsaturated, carbocyclic or heterocyclic ring optionally substituted with $C_{1-6}$-alkyl, $C_{1-6}$-alkoxy, $C_{1-6}$—alkylthio, hydroxy, amino, halogen, cyano, trifluoromethyl, aryl, heteroaryl, aroyl, heteroaroyl, arylsulfonyl, arylamino or heteroarylamino;

m, n, p and q independently are 0, 1 or 2;

X is a valence bond, —CH$_2$—, —C(=O)—, —C(=S)—, —S(=O)—, —S(=O)$_2$—, —C(=N—CN)—, —C(=CH—NO$_2$)—, —C[=C(CN)$_2$]—, —C(=CH—CN)—, or —C(=NR$^7$)— wherein R$^7$ is as defined above;

Y is a valence bond, —O— or —N(R$^7$)— wherein R$^7$ is as defined above;

A is a valence bond, $C_{1-8}$-alkylene, $C_{2-8}$-alkenylene, $C_{2-8}$-alkynylene, $C_{3-8}$-cycloalkylene or phenylene; or when Y is —N(R$^7$)—, A may together with R$^7$ form a 3 to 8 membered, saturated or unsaturated, carbocyclic or heterocyclic ring optionally substituted with $C_{1-6}$-alkyl, $C_{1-6}$-alkoxy, $C_{1-6}$-alkylthio, hydroxy, amino, halogen, cyano, trifluoromethyl, aryl, heteroaryl, aroyl, heteroaroyl, arylsulfonyl, arylamino or heteroarylamino; and Z is —R$^9$, —OR$^9$, —SR$^9$, —NR$^9$R$^{10}$, —CHR$^9$R$^{10}$ or =CR$^9$R$^{10}$ wherein R$^9$ and R$^{10}$ independently are hydrogen;

$C_{1-6}$-alkyl optionally substituted with aryl, arylamino, heteroarylamino, aroyl, heteroaroyl, arylsulfonyl, $C_{1-6}$-alkylsulfonyl, sulfonylamino, arylthio, heteroarylthio, aryloxy, acylamino, heteroaryl or $C_{3-8}$-cycloalkyl which are optionally substituted with $C_{1-6}$-alkyl, $C_{1-6}$-alkoxy, $C_{1-6}$-alkylthio, aryl-$C_{1-6}$-alkyl, heteroaryl-$C_{1-6}$-alkyl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, hydroxy, amino, halogen, cyano or trifluoromethyl;

$C_{2-6}$-alkenyl optionally substituted with aryl, arylamino, heteroarylamino, aroyl, heteroaroyl, arylsulfonyl, $C_{1-6}$-alkylsulfonyl, sulfonylamino, arylthio, heteroarylthio, aryloxy, acylamino, heteroaryl or $C_{3-8}$-cycloalkyl which are optionally substituted with $C_{1-6}$-alkyl, $C_{1-6}$-alkoxy, $C_{1-6}$-alkylthio, aryl-$C_{1-6}$-alkyl, heteroaryl-$C_{1-6}$-alkyl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, hydroxy, amino, halogen, cyano or trifluoromethyl;

$C_{2-6}$-alkynyl optionally substituted with aryl, arylamino, heteroarylamino, aroyl, heteroaroyl, arylsulfonyl, $C_{1-6}$-alkylsulfonyl, sulfonylamino, arylthio, heteroarylthio, aryloxy, acylamino, heteroaryl or $C_{3-8}$-cycloalkyl which are optionally substituted with $C_{1-6}$-alkyl, $C_{1-6}$-alkoxy, $C_{1-6}$-alkylthio, aryl-$C_{1-6}$-alkyl, heteroaryl-$C_{1-6}$-alkyl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, hydroxy, amino, halogen, cyano or trifluoromethyl;

aryl optionally substituted with aryl-$C_{1-6}$-alkyl, heteroaryl-$C_{1-6}$-alkyl, aryl, heteroaryl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, $C_{1-6}$-alkyl, $C_{1-6}$-alkoxy, $C_{1-6}$-alkylthio, hydroxy, amino, halogen, cyano or trifluoromethyl;

$C_{3-15}$-cycloalkyl optionally substituted with aryl-$C_{1-6}$-alkyl, heteroaryl-$C_{1-6}$-alkyl, aryl, heteroaryl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, $C_{1-6}$-alkyl, $C_{1-6}$-alkoxy, $C_{1-6}$-alkylthio, hydroxy, amino, halogen, cyano or trifluoromethyl;

aroyl optionally substituted with aryl-$C_{1-6}$-alkyl, heteroaryl-$C_{1-6}$-alkyl, aryl, heteroaryl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, $C_{1-6}$-alkyl, $C_{1-6}$-alkoxy, $C_{1-6}$-alkylthio, hydroxy, amino, halogen, cyano or trifluoromethyl; or heteroaryl optionally substituted with aryl-$C_{1-6}$-alkyl, heteroaryl-$C_{1-6}$-alkyl, aryl, heteroaryl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, $C_{1-6}$-alkyl, $C_{1-6}$-alkoxy, $C_{1-6}$-alkylthio, hydroxy, amino, halogen, cyano or trifluoromethyl, or R$^9$ and R$^{10}$ are joined by one or more bridging linkers such as a valence bond, $C_{1-4}$-alkylene, $C_{2-4}$-alkenylene, —O—, —S—, —N(R$^7$)—, —C(=O)—, —S(=O)—, —S(=O)$_2$—, —C(R$^7$R$^8$)—, phenylene, biphenylene, —O—$C_{1-4}$-alkylene, —S—$C_{1-4}$-alkylene, —N(R$^7$)—$C_{1-4}$-alkylene, —N=$C_{1-4}$-alkylene, —O—$C_{2-4}$-alkenylene, —S—$C_{2-4}$-alkenylene, or —N(R$^7$)—$C_{2-4}$-alkenylene, to form a mono-, bi- or polycyclic ring system; or when Y is —N(R$^7$)—, R$^9$ or R$^{10}$ may together with R$^7$ form a 3 to 8 membered, saturated or unsaturated, carbocyclic or heterocyclic ring optionally substituted with aryl-$C_{1-6}$-alkyl, heteroaryl-$C_{1-6}$-alkyl, aryl, heteroaryl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, $C_{1-6}$-alkyl, $C_{1-6}$-alkoxy, $C_{1-6}$-alkylthio, hydroxy, amino, halogen, cyano or trifluoromethyl;

provided that when X is —CS—, R$^1$=R$^2$=R$^5$=R$^6$=hydrogen, m=n=p=0 and q=1, the group —Y—A—Z must not start with the radical —NH—;

when the group —X—Y—A—Z starts with the radical —CH$_2$—, R$^1$=R$^2$=R$^6$=hydrogen, m=n=p=0 and q=1, R$^6$ must not be carboxy or aminocarbonyl;

when X is —CO—, the group —Y—A—Z starts with the radical —NH—, R$^1$=R$^2$=R$^6$=hydrogen, m=n=p=0 and q=1, the remainder of the group —Y—A—Z must not be hydrogen, unsubstituted or $C_{1-6}$-alkoxy substituted phenyl, unsubstituted $C_{3-8}$-cycloalkyl or unsubstituted $C_{1-6}$-alkyl;

when X is —CO—, the group —Y—A—Z starts with the radical —O—, $R^1=R^2=R^6$=hydrogen, m=n=p=0 and q=1, $R^5$ must not be carboxy, aminocarbonyl or hydrogen;

when —X is —CO—, the group —Y—A—Z starts with the radical —CH>, $R^1=R^2=R^3=R^4=R^6$=hydrogen, m=n=p=0 and q=1, $R^5$ must not be hydroxymethyl, $C_{1-6}$-alkoxycarbonyl or carboxy; and when X is —CO—, the group —Y—A—Z is 4-methoxyphenyl, $R^1=R^2=R^3=R^4=R^6$=hydrogen, m=n=p=0 and q=1, $R^5$ must not be carboxy;

and a pharmaceutically acceptable salt thereof or any optical isomer thereof or mixture of optical isomers, including a racemic mixture, or any tautomeric form.

Preferred embodiments thereof are as disclosed above for formula I.

The compounds of the present invention may have one or more asymmetric centers and it is intended that any optical isomers, as separated, pure or partially purified optical isomers or racemic mixtures thereof are included in the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods known to the skilled artisan. Such solvates are also contemplated as being within the scope of the present invention.

The invention also encompasses prodrugs of the present compounds, which on administration undergo chemical conversion by metabolic processes before becoming active pharmacological substances. In general, such prodrugs will be functional derivatives of the compounds, which are readily convertible in vivo into the present compounds. Conventional procedures for the selection and preparation of suitable prodrug derivatives are described, for example, in "Design of Prodrugs", ed. H. Bundgaard, Elsevier, 1985.

The invention also encompasses active metabolites of the present compounds. The compounds of the present invention interact with the histamine H3 receptor and may thus be used for the treatment of a wide range of conditions and disorders in which histamine H3 receptor interactions are beneficial.

Accordingly, in another aspect the present invention relates to a compound of formula I as well as any optical or geometric isomer or tautomeric form thereof including mixtures of these or a pharmaceutically acceptable salt thereof for use as a medicament.

The invention also relates to pharmaceutical compositions comprising, as an active ingredient, at least one compound of formula I as well as any optical or geometric isomer or tautomeric form thereof including mixtures of these or a pharmaceutically acceptable salt thereof together with one or more pharmaceutically acceptable carriers or diluents.

Furthermore, the invention relates to the use of a compound of the general formula I'

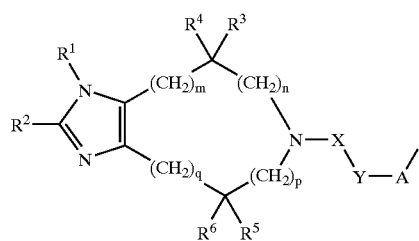

wherein
$R^1$ is hydrogen or a functional group which can be converted to hydrogen in vivo;
$R^2$ is hydrogen, $C_{1-6}$-alkyl, halogen, cyano, trifluoromethyl, trifluoromethoxy, hydroxy or —$NR^7R^8$,
wherein $R^7$ and $R^8$ independently are
hydrogen,
$C_{1-6}$-alkyl optionally substituted with
aryl, heteroaryl, aroyl, heteroaroyl, arylsulfonyl, arylamino, heteroarylamino or $C_{3-8}$-cycloalkyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino,
aryl, heteroaryl, aroyl, heteroaroyl, arylsulfonyl or heteroarylsulfonyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, $C_{1-6}$-alkylsulfonyl optionally substituted with
$C_{3-8}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, or $R^7$ and $R^8$, together with the nitrogen atom to which they are connected, form a 3 to 8-membered, saturated or unsaturated, heterocyclic ring optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;

$R^3$, $R^4$, $R^5$ and $R^6$ independently are hydrogen, carboxy, $C_{1-6}$-alkoxycarbonyl, cyano, trifluoromethyl, halogen, $C_{3-8}$-cycloalkyl optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, $C_{1-6}$-alkyl, $C_{2-6}$-alkenyl or $C_{2-6}$-alkynyl, which are optionally substituted with
$C_{1-6}$-alkoxy, $C_{1-6}$-alkylthio, hydroxy, cyano, halogen, trifluoromethyl, trifluoromethoxy, carboxy, $C_{1-6}$-alkoxycarbonyl,
$C_{3-8}$-cycloalkyl, aryl, heteroaryl, aroyl, heteroaroyl, arylsulfonyl, arylamino or heteroarylamino, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino, heteroarylamino or —CO—NR$^9$R$^{10}$, aryl optionally substituted with
halogen, cyano, nitro, $C_{1-6}$-alkyl, $C_{1-6}$-alkoxy, hydroxy, trifluoromethyl, trifluoromethoxy, aryl, heteroaryl, aryloxy, aroyl, heteroaroyl, arylsulfonyl, arylamino, heteroarylamino or —CO—NR$^9$R$^{10}$,

—CO—N$^9$R$^{10}$, wherein $R^9$ and $R^{10}$ independently are hydrogen, $C_{1-6}$-alkyl optionally substituted with
aryl, heteroaryl, aroyl, heteroaroyl, arylsulfonyl, arylamino, heteroarylamino or $C_{3-8}$-cycloalkyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, $C_{1-6}$-alkylsulfonyl optionally substituted with
$C_{1-6}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, or $R^9$ and $R^{10}$, together with the nitrogen atom to which they are connected, form a 3 to 8-membered, saturated or unsaturated, heterocyclic ring optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, or $R^3$ and $R^4$, together with the carbon atom to which they are connected, and/or $R^5$ and $R^6$ together with the carbon atom to which they are connected, form a 3 to 8-membered, saturated or unsaturated, carbocyclic or heterocyclic ring optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;

m, n, p and q independently are 0, 1 or 2;

X is a valence bond, —CH$_2$—, —C(=O)—, —C(=S)—, —S(=O)—, —S(=O)$_2$—, —C(=N—CN)—, —C(=CH—NO$_2$)—, —C[=C(CN)$_2$]—, —C(=CH—CN)—, —C(=NR$^{11}$)— or —C(=N—S(=O)$_2$R$^{11a}$)—, wherein $R^{11}$ is hydrogen, $C_{1-6}$-alkyl optionally substituted with
aryl, heteroaryl, aroyl, heteroaroyl, arylsulfonyl, arylamino, heteroarylamino or $C_{3-8}$-cycloalkyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, $C_{1-6}$-alkylsulfonyl optionally substituted with
$C_{3-8}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;

$R^{11a}$ is $C_{1-6}$-alkyl optionally substituted with
aryl, heteroaryl, aroyl, heteroaroyl, arylsulfonyl, arylamino, heteroarylamino or $C_{3-8}$-cycloalkyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, Y is a valence bond, —O— or —N($R^{12}$)—, wherein $R^{12}$ is hydrogen, $C_{1-6}$-alkyl optionally substituted with aryl, heteroaryl, aroyl, heteroaroyl, arylsulfonyl, arylamino, heteroarylamino or $C_{3-8}$-cycloalkyl, which are optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, $C_{1-6}$-alkylsulfonyl optionally substituted with $C_{3-8}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;

A is a valence bond, $C_{1-6}$-alkylene, $C_{2-8}$-alkenylene, $C_{2-8}$-alkynylene, $C_{3-8}$-cycloalkylene or phenylene, or when Y is —N($R^{12}$)—, A, together with $R^{12}$ and the nitrogen atom to which they are connected, may form a 3 to 8 membered, saturated or unsaturated, heterocyclic ring system optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aryl-$C_{1-6}$-alkyl, heteroaryl-$C_{1-6}$-alkyl, aroyl, heteroaroyl, arylsulfonyl, arylamino or heteroarylamino; and Z is —$R^{13}$, —$OR^{13}$, —$SR^{13}$, —$NR^{13}R^{14}$, —$CHR^{13}R^{14}$, —$CR^{13}R^{14}R^{15}$ or =$CR^{13}R^{14}$, wherein $R^{13}$, $R^{14}$ and $R^{15}$ independently are hydrogen, $C_{1-6}$-alkyl, $C_{2-6}$-alkenyl or $C_{2-6}$-alkynyl, which are optionally substituted with aryl, arylamino, heteroarylamino, aroyl, heteroaroyl, arylsulfonyl, $C_{1-6}$-alkylsulfonyl, sulfonylamino, arylthio, heteroarylthio, aryloxy, acylamino, heteroaryl or $C_{3-8}$-cycloalkyl, which are optionally substituted with $C_{1-6}$-alkyl, $C_{1-6}$-alkoxy, $C_{1-6}$-alkylthio, aryl-$C_{1-6}$-alkyl, heteroaryl-$C_{1-6}$-alkyl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, hydroxy, amino, $C_{1-6}$-alkylamino, di($C_{1-6}$-alkyl)amino, halogen, cyano, trifluoromethoxy or trifluoromethyl, aryl, $C_{3-15}$-cycloalkyl, $C_{3-15}$-cycloalkenyl, $C_{3-15}$-cycloalkynyl, aroyl or heteroaryl, which are optionally substituted with aryl-$C_{1-6}$-alkyl, heteroaryl-$C_{1-6}$-alkyl, aryl, heteroaryl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, $C_{1-6}$-alkyl, $C_{1-6}$-alkoxy, $C_{1-6}$-alkylthio, $C_{3-8}$-cycloalkanecarbonyl, hydroxy, amino, $C_{1-6}$-alkylamino, di($C_{1-6}$-alkyl) amino, halogen, cyano, trifluoromethoxy or trifluoromethyl, where $R^{13}$ and $R^{14}$ or $R^{13}$, $R^{14}$ and $R^{15}$, when they do not represent hydrogen, may be joined by one or more bridging linkers such as a valence bond, $C_{1-4}$-alkylene, $C_{2-4}$-alkenylene, —O—, —S—, —N($R^{16}$)—, —C(=O), —S(=O)—, —S(=O)$_2$—, —C($R^{16}R^{17}$)—, phenylene, biphenylene, —O—$C_{1-4}$-alkylene, —S—$C_{1-4}$-alkylene, —N($R^{16}$)—$C_{1-4}$-alkylene, —N=$C_{1-4}$-alkylene, —O—$C_{2-4}$-alkenylene, —S—$C_{2-4}$-alkenylene or —N($R^{16}$)—$C_{2-4}$-alkenylene, to form a mono-, bi- or polycyclic ring system, wherein $R^{16}$ and $R^{17}$ independently are hydrogen, $C_{1-6}$-alkyl optionally substituted with aryl, heteroaryl, aroyl, heteroaroyl, arylsulfonyl, arylamino, heteroarylamino or $C_{3-8}$-cycloalkyl, which are optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, $C_{1-6}$-alkylsulfonyl optionally substituted with $C_{3-8}$-cycloalkyl, $C_{1-6}$-alkoxy, $C_{1-6}$-alkylthio, hydroxy, amino, $C_{1-6}$-alkylamino, di($C_{1-6}$-alkyl) amino, halogen, cyano, trifluoromethyl, trifluoromethoxy, aryl, heteroaryl, aroyl, heteroaroyl, arylsulfonyl, arylamino or heteroarylamino, or $R^{16}$ and $R^{17}$, together with the nitrogen atom to which they are connected, form a 3 to 8 membered, saturated or unsaturated, heterocyclic ring optionally containing one or more further heteroatoms selected from nitrogen, oxygen and sulfur, and optionally substituted with $C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino;

as well as any optical or geometric isomer or tautomeric form thereof including mixtures of these or a pharmaceutically acceptable salt thereof for the preparation of a medicament for the treatment and/or prevention of disorders and diseases related to the histamine H3 receptor.

In still another aspect, the invention relates to a method for the treatment of disorders related to the histamine H3 receptor the method comprising administering to a subject in need thereof an effective amount of a compound of formula I' as well as any optical or geometric isomer or tautomeric form thereof including mixtures of these or a pharmaceutically acceptable salt thereof or a pharmaceutical composition comprising the same.

More particularly, the present compounds may possess histamine H3 receptor antagonistic activity and would accordingly be useful in the treatment of a wide range of conditions and disorders in which a histamine H3 receptor blockade is beneficial.

In a preferred embodiment of the invention the present compounds are used for the preparation of a pharmaceutical composition for the reduction of weight.

In a preferred embodiment of the invention the present compounds are used for the preparation of a pharmaceutical composition for the treatment and/or prevention of overweight or obesity.

In another preferred embodiment of the invention the present compounds are used for the preparation of a pharmaceutical composition for the suppression of appetite or satiety induction.

In a further preferred embodiment of the invention the present compounds are used for the preparation of a pharmaceutical composition for the prevention and/or treatment of disorders and diseases related to overweight or obesity such as atherosclerosis, hypertension, IGT (impaired glucose tolerance), diabetes, especially Type 2 diabetes (NIDDM (non-insulin dependent diabetes mellitus)), dyslipidemia, coronary heart disease, gallbladder disease, osteoarthritis and various types of cancer such as endometrial, breast, prostate and colon cancers.

In yet a further preferred embodiment of the invention the present compounds are used for the preparation of a pharmaceutical composition for the prevention and/or treatment of eating disorders such as bulimia and binge eating.

In a further preferred embodiment of the invention the present compounds are used for the preparation of a pharmaceutical composition for the treatment and/or prevention of IGT.

In a further preferred embodiment of the invention the present compounds are used for the preparation of a pharmaceutical composition for the treatment and/or prevention of Type 2 diabetes.

In another preferred embodiment of the invention the present compounds are used for the preparation of a pharmaceutical composition for the delaying or prevention of the progression from IGT to Type 2 diabetes.

In a further preferred embodiment of the invention the present compounds are used for the preparation of a pharmaceutical composition for the delaying or prevention of the progression from non-insulin requiring Type 2 diabetes to insulin requiring Type 2 diabetes.

The compounds of the present invention may also be used for the treatment of airway disorders such as asthma, as anti-diarrheals and for the modulation of gastric acid secretion.

Furthermore, the compounds of the present invention may be used for the treatment of diseases associated with the regulation of sleep and wakefulness and for the treatment of narcolepsy and attention deficit disorders.

Moreover, the compounds of the invention may be used as stimulants or as sedatives.

The present compounds may also be used for the treatment of conditions associated with epilepsy. Additionally, the present compounds may be used for the treatment of motion sickness and vertigo. Furthermore, they may be useful as regulators of hypothalamo-hypophyseal secretion, antidepressants, modulators of cerebral circulation, and in the treatment of irritable bowel syndrome.

Further, the compounds of the present invention may be used for the treatment of dementia and Alzheimer's disease.

The present novel compounds may also interact with the vanilloid receptors, the serotonin receptors, and the adrenergic receptors and may be useful for the treatment of diseases associated with these receptors. Hence, the compounds of the present invention may be vanilloid receptor agonists, and thus be useful for the treatment of obesity by enhancement of the metabolic rate and energy expenditure. Further, by virtue of their interaction with the vanilloid receptor the compounds of the present invention may be useful for the treatment of pain or neurogenic inflammation or inflammatory painful conditions.

In a further preferred embodiment of the invention the present compounds are used for the preparation of a pharmaceutical composition for the treatment and/or prevention of diseases and disorders related to the vanilloid receptor, such as for the treatment and/or prevention of pain, neurogenic inflammation or obesity.

Furthermore, the present compounds may interact with the 5-HT3 receptor (serotonin-3-receptor) and may accordingly be useful as antiemetics, in particular the chemotherapy-induced emesis. Further potential applications of 5-HT3 antagonists include treatment of central nervous system disorders such as anxiety, schizophrenia, drug abuse and withdrawal symptoms, and pathological and age-associated amnesia.

In a further preferred embodiment of the invention the present compounds are used for the preparation of a pharmaceutical composition for the treatment and/or prevention of diseases and disorders related to the serotonin-3 receptor (5-HT3), such as for the treatment of emesis.

Furthermore, the present compounds may interact with the adrenergic alpha-2 receptor and thus be useful for the treatment of hypertension and of conditions associated with overexpression or hypersensitization of the adrenergic alpha-2 receptor, especially obesity, withdrawal symptoms to an adrenergic alpha-2 agonist, neurological disorders (especially orthostatic hypotension), multiple system atrophy, diabetes mellitus, benign prostatic hyperplasia or drug induced sensitization of the adrenergic alpha-2 receptor. Moreover, the compounds of the present invention, by virtue of their interaction with the alpha-2 receptor, may be useful as sedatives and hypnotics (sleep inducing agents) or as stimulants.

In a further preferred embodiment of the invention the present compounds are used for the preparation of a pharmaceutical composition for the treatment and/or prevention of diseases and disorders related to the alpha-2 adrenergic receptor, such as for use as a sleep inducing agent.

The present compounds may be administered in combination with one or more further pharmacologically active substances, e.g., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycemic agents.

The orally active hypoglycemic agents preferably comprise sulphonylureas, biguanides, meglitinides, oxadiazolidinediones, thiazolidinediones, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, insulin sensitizers, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents, compounds lowering food intake, PPAR and RXR agonists and agents acting on the ATP-dependent potassium channel of the α-cells.

In one embodiment of the invention the present compounds are administered in combination with insulin.

In a further embodiment the present compounds are administered in combination with a sulphonylurea, e.g., tolbutamide, glibenclamide, glipizide or glicazide.

In another embodiment the present compounds are administered in combination with a biguanide, e.g., metformin.

In yet another embodiment the present compounds are administered in combination with a meglitinide, e.g., repaglinide.

In still another embodiment the present compounds are administered in combination with a thiazolidinedione, e.g., troglitazone, ciglitazone, pioglitazone, rosiglitazone or the compounds disclosed in WO 97/41097 to Dr. Reddy's Research Foundation.

Furthermore, the present compounds may be administered in combination with the insulin sensitizers disclosed in WO 99/19313 to Dr. Reddy's Research Foundation.

In a further embodiment the present compounds are administered in combination with an α-glucosidase inhibitor, e.g., miglitol or acarbose.

In another embodiment the present compounds are administered in combination with an agent acting on the ATP-dependent potassium channel of the β-cells, e.g., tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent, e.g., cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds, e.g., in combination with a sulphonylurea and metformin, a sulphonylurea and acarbose, repaglinide and metformin, insulin and a sulphonylurea, insulin and metformin, insulin and troglitazone, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound according to the invention contains a free base such salts are prepared in a conventional manner by treating a solution or suspension of a free base of the compound according to the invention with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the compounds according to the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet, which may be prepared by conventional tabletting techniques, may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite | 1.0 mg |
| Magnesil stearas Ph. Eur. | q.s. |
| Coating: | |
| HPMC approx. | 9 mg |
| Mywacett 940 T* approx. | 0.9 mg |

*Acylated monoglyceride used as plasticizer for film coating.

If desired, the pharmaceutical composition of the invention may comprise the compound of formula I' in combination with further pharmacologically active substances.

The preparation of the compounds of this invention can be realized in many different ways. The preparation of imidazoles of formula III has been described in the literature (see e.g. F. B. Stocker et al., *J. Org. Chem.* 1966, 31, 2380; idem, ibid. 1990, 55, 3370; T. Vitali et al., *Il Farmaco* 1967, 22, 821; idem, ibid. 1965, 20, 634; S. Fränkel, K. Zeimer, *Biochemische Zeitschrift* 1920, 110, 238; G. Arcari et al., Fr. Pat. 1976, 2 337 726; DE 2700012, 1977, *Chem. Abstr.*, 87, 201535).

Compounds of formula Ia, wherein $R^1$ and $R^2$ are hydrogen, m=n=p=0 and q=1 can be prepared as outlined below:

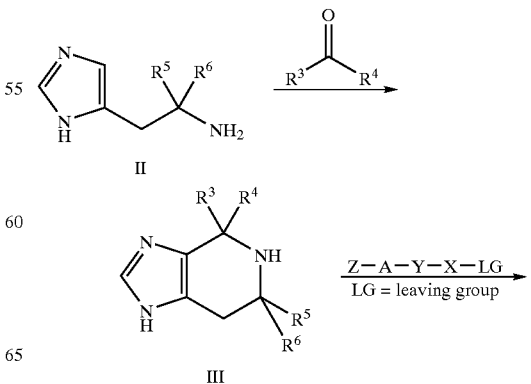

-continued

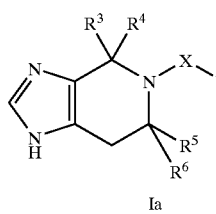

Ia

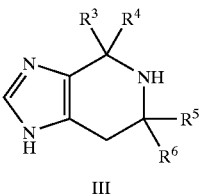

III

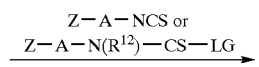

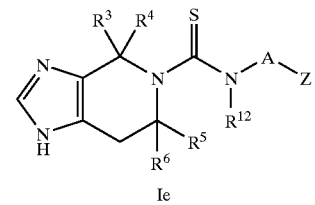

Ie

LG = leaving group

More specifically, different types of compounds of formula Ia of this invention can be prepared by the methods 1) to 4) sketched below:

1) 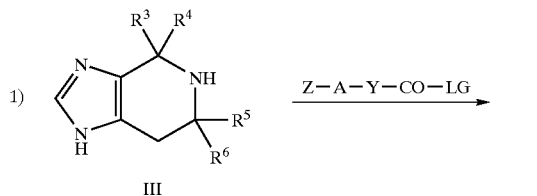

Ib

2) 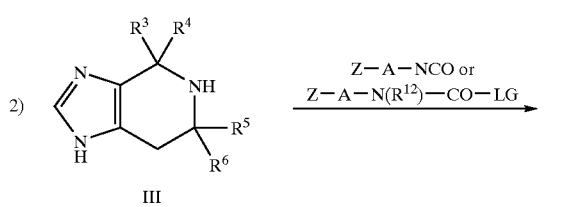

Ic

3) 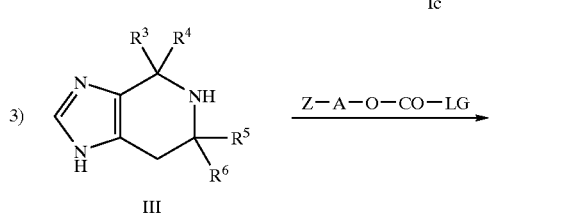

Id

For instance, compounds of the formula Ib can be synthesized from 4,5,6,7-tetrahydroimidazo[4,5-c]pyridines III by treating the latter with suitable activated derivatives of carboxylic acids, such as acyl imidazoles, anhydrides, acid chlorides or active esters, or any of the derivatives commonly used for the preparation of carboxamides, under appropriate conditions.

Compounds of the formula Ic can be prepared by treating 4,5,6,7-tetrahydroimidazo[4,5-c]pyridines III with isocyanates Z—A—NCO or with synthetic equivalents thereof, such as carbamoyl chlorides Z—A—N($R^{12}$)—CO—Cl under suitable conditions.

Compounds of the formula Id can be synthesized by treating 4,5,6,7-tetrahydro-imidazo[4,5-c]pyridines III with haloformates Z—A—O—CO—Cl or with synthetic equivalents thereof such as activated carbonates (e.g., 4-nitrophenyl carbonates) under suitable conditions.

Finally, compounds of the formula Ie can be prepared by treating 4,5,6,7-tetrahydroimidazo[4,5-c]pyridines III with isothiocyanates Z—A—NCS or with synthetic equivalents thereof, such as thiocarbamoyl chlorides Z—A—N($R^{12}$)—CS—Cl under suitable conditions.

The starting materials are either known compounds or compounds, which may be prepared in analogy with the preparation of similar known compounds.

The present invention is further illustrated by the following representative examples, which are, however, not intended to limit the scope of the invention in any way.

EXAMPLES

In the examples the following terms are intended to have the following, general meanings:
DCM: dichloromethane, methylenechloride
DMF: N,N-dimethyl formamide
DMSO: dimethyl sulfoxide
EDC: 1N-ethyl-N'-(3-dimethylaminopropyl)carbodiimide hydrochloride
HOBt: N-hydroxybenzotriazole, 1-hydroxybenzotriazole
NMP: N-methylpyrrolidone
NMR spectra were recorded on Bruker 300 MHz and 400 MHz instruments. HPLC-MS was performed on a Perkin Elmer instrument (API 100).
HPLC-systems from Merck-Hitachi (Hibar™ RT 250-4, Lichrosorb™ RP 18, 5.0 μm, 4.0×250 mm, gradient elution, 20% to 80% acetonitrile in water within 30 min, 1.0 mL/min, detection at 254 nm) and Waters (Symmetry™, $C_{18}$, 3.5 μm, 3.0×150 mm, gradient elution, 5% to 90% acetonitrile in water within 15 min, 1.0 mL/min, detection at 214 nm) were used.

Furthermore, where stated the following HPLC method h8 was used:

The reverse phase analysis was performed using UV detections at 214, 254, 276 and 301 nm on a 218TP54 4.6 mm×150 mm C-18 silica column, which was eluted at 1 mL/min at 42° C. The column was equilibrated with 5% acetonitrile, 85% water and 10% of a solution of 0.5% trifluoroacetic acid in water and eluted by a linear gradient from 5% acetonitrile, 85% water and 10% of a solution of 0.5% trifluoroacetic acid to 90% acetonitrile and 10% of a solution of 0.5% trifluoroacetic acid over 15 min.

Where stated the following general procedures were used:

General Procedure A:

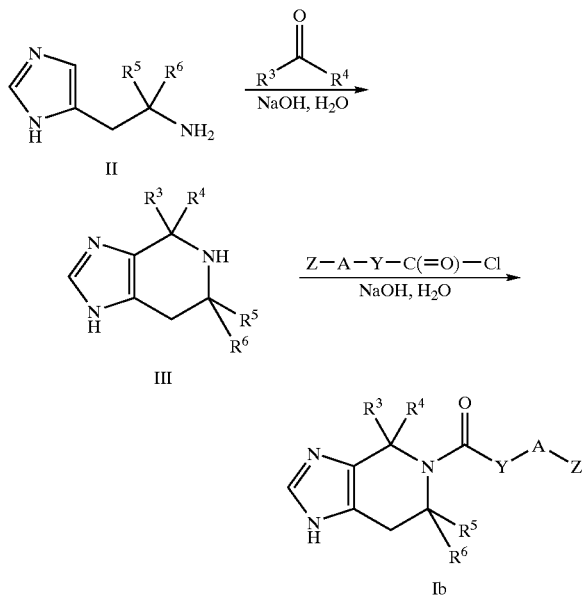

To a solution of the dihydrochloride of the amine II (10.0 mmol) in water (5 mL) an aqueous sodium hydroxide solution (12 N, 4.2 mL, 50.4 mmol), methanol (35 mL) and the carbonyl compound $R^3R^4CO$ (25.0 mmol) were added. The resulting mixture was refluxed overnight, water (15 mL) was added, methanol was evaporated under reduced pressure and the residue was diluted with water to a volume of approximately 25 mL. The resulting mixture was washed with ether (2×50 mL, removal of excess ketone) and then, while stirring vigorously, the acyl halide (Z—A—Y—CO—Cl, 11.5 mmol) was added portionwise. After stirring for 10 min the mixture was extracted with DCM (2×100 mL). The combined organic phases were washed with water (25 mL), dried (MgSO$_4$) and concentrated. The remaining oil was redissolved in ethyl acetate (100 mL) and a solution of oxalic acid (0.45 g, 5.0 mmol) in ethyl acetate (25 mL) was added. After stirring for 30 min the precipitate was filtered off and dried under reduced pressure. Alternatively, the crude product Ib could be purified by column chromatography (silica gel, gradient elution with heptane/ethyl acetate/methanol).

General Procedure B:

A mixture of the dihydrochloride of the amine II (95 mmol), water (200 mL), and the carbonyl compound $R^3R^4CO$ (133 mmol) was refluxed until no more amine II could be detected (HPLC). The mixture was then concentrated to dryness and the crude product III was purified by recrystallization.

The purified amine III was then acylated as in general procedure A or by any other, conventional method.

General Procedure C:

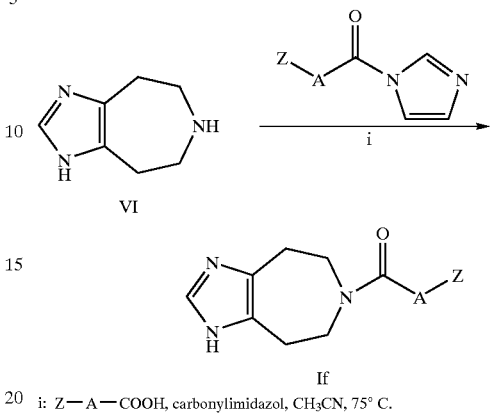

i: Z—A—COOH, carbonylimidazol, CH$_3$CN, 75° C.

To 0.3 mmol of the corresponding acid in CH$_3$CN (1 mL) was added 0.31 mmol N,N-carbonyldiimidazol in portions. The reaction mixture was stirred for 30 min. at room temperature and for 2 h at 75° C. Then, it was cooled to room temperature and 0.25 mmol of VI were added. The reaction mixture was heated for 2–5 h at 75° C., cooled to room temperature and evaporated to dryness. The residue was chromatographed on SiO$_2$ with CH$_2$Cl$_2$/MeOH (10:1 to 4:1) to yield a compound of the general formula If as a white amorphous solid.

General Procedure D:

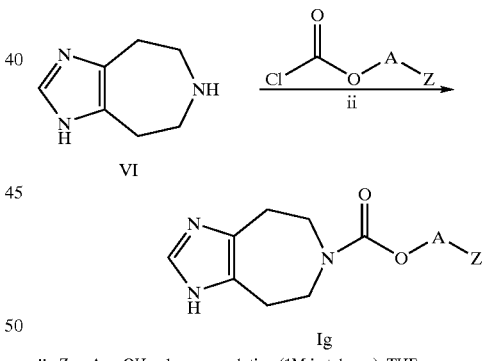

ii: Z—A—OH, phosgene solution (1M in toluene), THF

To a solution of 0.3 mmol of the corresponding alcohol Z—A—OH in THF (1 mL) was added at 4° C. 0.16 mL phosgene solution (1.9 M in toluene). The reaction mixture was stirred for 3 h at room temperature and evaporated to dryness. The residue was dissolved in CH$_3$CN (0.3 mL) and added to a solution of 0.25 mmol VI in CH$_3$CN (1 mL) at room temperature and stirred for 24 h at room temperature to 50° C. The reaction mixture was evaporated to dryness and the residue chromatographed on SiO$_2$ with CH$_2$Cl$_2$/MeOH (10:1 to 4:1) to yield a compound of formula Ig as a white amorphous solid.

General Procedure E:

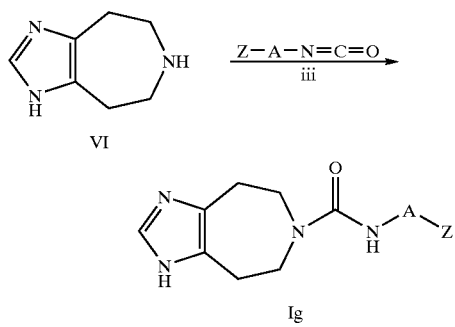

iii: Z—A—NH$_2$, triphosgene, Hünig's base, CH$_3$CN

To a solution of 0.3 mmol amine or aniline Z—A—NH$_2$ in CH$_3$CN (1 mL) was added at 4° C. 0.11 mmol triphosgene and 0.9 mmol Hünig's base to yield a clear solution, which was stirred for 30 min. at room temperature and for 2 h at 75° C. Building block VI (0.25 mmol) was added at room temperature and the reaction mixture stirred for 24 h at 25–50° C., cooled to room temperature and evaporated to dryness. The residue was chromatographed on SiO$_2$ with CH$_2$Cl$_2$/MeOH (10:1 to 4:1) to yield a compound of the general formula Ig as a white amorphous solid.

The key building blocks VI used in the above General Procedures C, D and E were synthesized as shown in Scheme 1. The synthesis of the non-commmercial building blocks used is described in Scheme 2.

Scheme 1

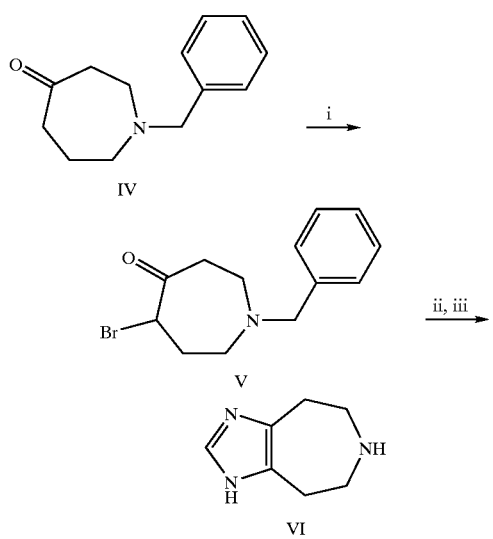

i: Br$_2$, HBr-AcOH, AcOH
ii: formamidine x AcOH, EtOH, 80° C.; then aq. NaNCO$_3$ and extraction with CHCl$_3$ and chromatography with CH$_2$Cl$_2$/MeOH (9:1)
iii: Pd/C, EtOH Synthesis of 4,5,7,8-tetrahydro-1H,6H-imidazo[4,5-d]azepine VI from 1-benzylhexahydroazepin-4-one hydrochloride IV Step (i): 1-Benzyl-5 bromohexahydroazepin-4-one hydrobromide V 175 g of (0.732 mol) 1-benzylhexahydroazepin-4-one hydrochloride IV are dissolved in 500 mL acetic acid. Upon addition of 100 mL of a saturated solution (30%) of hydrobromic acid in acetic acid, 37 mL (0.732 mol) of bromine are added dropwise at room temperature and with efficient stirring, whereby the brown color of bromine disappears.

After completion of the addition the reaction mixture is concentrated on a rotavapor at a bath temperature of 35° C.

The resulting oily residue is triturated with ether and the ether layer decanted. Then 250 mL of ethyl acetate are added. The mixture is stirred and heated on a steam bath until crystallization occurs. After cooling the ethyl acetate is removed by decantation and heated a second time with fresh ethyl acetate. Thereafter the crystalline material is collected by filtration and dried in vacuo.

Yield: 217.8 g (82%), m.p. 148–150° C.

Step (ii): 6-Benzyl-4,5,7,8-tetrahydro-1H,6H-imidazo[4,5-d]azepine

A solution of sodium ethanolate is prepared by dissolving 1.4 g (60 mmol) of sodium in 150 mL of dry ethanol. Then 4.8 g (60 mmol) of formamidine hydrochloride and 7.3 g (20 mmol) of 1-benzyl-5-bromohexahydroazepin-4-one hydrobromide as well as 80 mL chloroform are added successively. After keeping at reflux for about 8 hours the mixture is cooled and treated with a solution of 40 mmol of sodium hydroxide in dry methanol. The reaction mixture is concentrated on a rotavapor and the residue purified by column chromatography on silica gel with chloroform/methanol 9:1 as eluent.

Upon evaporation of the respective fractions the product is triturated with ethyl ether and collected by filtration.

Yield: 1.1 g (24.4%).

Step (ill): 4,5,7,8-Tetrahydro-1H,6H-imidazo[4,5-d]azepine 25.4 mmol of 6-benzyl-4,5,7,8-tetrahydro-1H-imidazo[4,5-d]azepine are dissolved in 180 ml, ethanol and upon addition of 1.5 g palladium on charcoal treated with hydrogen at a pressure of 5 bar.

After removal of the catalyst the filtrate is evaporated on a rotavapor and the residue crystallized from acetonitrile.

Yield of 4,5,7,8-tetrahydro-1H,6H-imidazo[4,5-d]azepine=59.3%.

The synthesis of the non-commercial building blocks 1–7 are described in Scheme 2.

Scheme 2

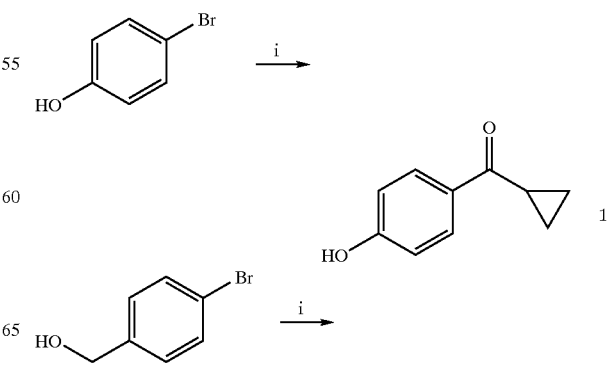

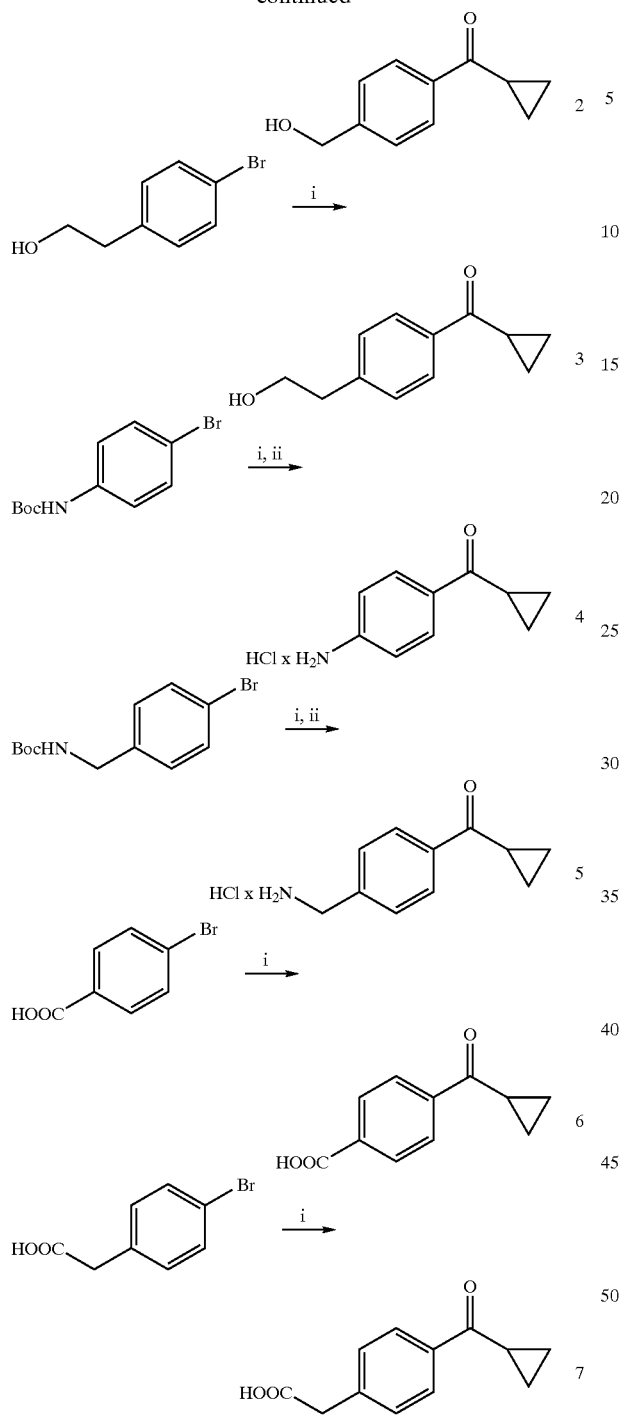

i: MeLi (1.6M in Et₂O, 1.1 equiv.), THF, 0° C.; then tertiary BuLi (1.5 M in pentane, 2.2 equiv.), -78° C., 1h; then Weinreb amide of cyclopropane carboxylic acid, 0° C.
ii: 4 N HCl in dioxane To a stirred solution of a commercially available bromide (10 mmol) in THF (40 mL) was added at 4° C. MeLi solution (6.9 ml, 1.1 equiv., 1.6 M in Et₂O). The reaction mixture was stirred for 30 min. at 4° C., cooled to -78° C. followed by addition of tertiary BuLi solution (14.7 mL, 2.2 equiv., 1.5 M in pentane). The reaction mixture was stirred for 1 h at -78° C. followed by addition of the Weinreb amide of cyclopropane carboxylic acid (15.0 mmol). The reaction mixture was allowed to warm to 0° C. overnight and poured onto ice, 0.5 N HCl solution and EtOAc. The organic layer was washed with saturated brine, dried (MgSO₄) and evaporated and the residue chromatographed on SiO₂.

Building Blocks:

1: $^1$H NMR (300 MHz, DMSO-$d_6$): δ10.32 (br. s, 1H); 7.91 (d, J=8.8, 2H); 6.84 (d, J=8.8, 2H); 2.77 (m, 1H); 0.96–0.93 (m, 4H).

2: $^1$H NMR (300 MHz, DMSO-$d_6$): δ7.99 (d, J=8.2, 2H); 7.46 (d, J=8.4, 2H); 5.35 (t, J=5.7, 1H); 4.57 (d, J=5.7, 2H); 2.87 (m, 1H); 1.03–1.00 (m, 4H).

3: $^1$H NMR (300 MHz, CDCl₃): δ7.94 (d, J=8.3, 2H); 7.32 (d, J=8.4, 2H); 3.87 (t, J=6.6, 2H); 2.92 (t, J=6.6, 2H); 2.65 (m, 2H); 1.27–1.19 (m, 2H); 1.05–0.99 (m, 2H).

4: $^1$H NMR (300 MHz, DMSO-$d_6$): δ8.18 (br. s, 3H); 7.85 (d, J=8.8, 2H); 6.82 (d, J=8.8, 2H); 2.74 (m, 1H); 0.92–0.88 (m, 4H).

5: $^1$H NMR (300 MHz, DMSO-$d_6$): δ8.56 (br. s, 3H); 8.06 (d, J=8.4, 2H); 7.64 (d, J=8.6, 2H); 4.10 (s, 2H); 2.90 (m, 1H); 1.06–1.01 (m, 4H).

6: $^1$H NMR (300 MHz, CDCl₃): δ8.22 (d, J=8.6, 2H); 8.09 (d, J=8.4, 2H); 2.69 (m, 1H); 1.30 (m, 2H); 1.12 (m, 2H).

7: could not be obtained in pure form.

Example 1

5-(3-Cyclohexylpropanoyl)-4,4-dimethyl-4,5,6,7-tetrahydroimidazo[4,5-c]pyridine Oxalic Acid Salt

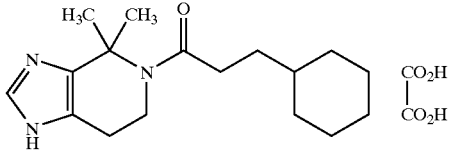

Following the General Procedure A using histamine dihydrochloride (1.84 g, 10.0 mmol), acetone (4.0 mL) and 3-cyclohexylpropanoyl chloride (2.0 g, 11.5 mmol) 0.80 g (21%) of the title amide was obtained as oxalic acid salt.

HPLC (214 nm): elution at 18.59 min. LC-MS: Calcd. for MH⁺: 290; found: 290.

$^1$H NMR (400 MHz, DMSO-$d_6$, two rotamers, 6:4): δ0.80–0.95 (m, 2H), 1.05–1.28 (m, 4H), 1.35–1.76 (m, 13H), 2.38 (m, 1.2H), 2.64 (t, J=5 Hz, 1.2H), 2.89 (t, J=5 Hz, 0.8H), 3.01 (t, J=7 Hz, 0.8H), 3.54 (t, J=5 Hz, 0.8H), 3.58 (t, J=5 Hz, 1.2H), 8.25 (s, 0.6H), 8.34 (s, 0.4H).

Example 2

5-(5-Cyclohexylpentanoyl)-4,5,6,7-tetrahydroimidazo[4,5-c]pyridine

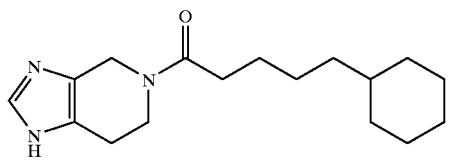

To a solution of 5-cyclohexylpentanoic acid (0.94 g, 5.10 mmol) in DCM (4 mL) carbonyldiimidazole (0.83 g, 5.12 mmol) was added. The resulting mixture was stirred at room temperature for 16 h and then added to a solution of 4,5,6,7-tetrahydroimidazo[4,5-c]pyridine (5.10 mmol) in DCM (4 mL). After 2.5 h DCM (50 mL) was added and the mixture was washed with water (3×15 mL). The organic layer was then dried (MgSO₄) and concentrated. The crude product was purified by column chromatography (silica gel, ethyl acetate/methanol 9:1) whereby 0.35 g (24%) of the title amide was obtained as an oil.

HPLC (214 nm): elution at 20.74 min. LC-MS: Calcd. for MH⁺: 290; found: 290.

¹H NMR (400 MHz, DMSO-d₆, two rotamers, 1:1): δ0.70–0.80 (m, 2H), 1.05–1.34 (m, 8H), 1.43–1.52 (m, 2H), 1.55–1.71 (m, 5H), 2.36 (m, 2H), 2.52 (t, J=5 Hz, 1H), 2.62 (t, J=5 Hz, 1H), 3.68 (t, J=5 Hz, 1H), 3.74 (t, J=5 Hz, 1H), 4.41 (s, 2H), 7.47 (s, 0.5H), 7.49 (s, 0.5H), 11.85 (s, br, 1H).

Example 3

5-(6-Phenylhexanoyl)-4,5,6,7-tetrahydroimidazo[4,5-c]pyridine

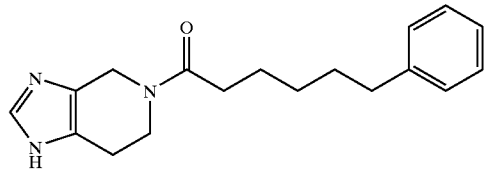

To a solution of carbonyldiimidazole (0.83 g, 5.12 mmol) in DCM (8 mL) 6-phenylhexanoic acid (0.98 g, 5.10 mmol) was added dropwise. The mixture was stirred at room temperature for 20 h, and then a solution of 4,5,6,7-tetrahydroimidazo[4,5-c]-pyridine (5.10 mmol) in DMF (1 mL) and DCM (1 mL) was added. After stirring for four days DCM (100 mL) was added and the mixture was washed with water (15 mL) and dried (MgSO₄). Concentration and column chromatography (silica gel, ethyl acetate/methanol 9:1) gave 0.80 g (53%) of the title amide as an oil.

¹H NMR (400 MHz, DMSO-d₆, two rotamers, 1:1): δ1.22–1.38 (m, 2H), 1.46–1.64 (m, 4H), 2.38 (m, 2H), 2.45–2.68 (m, 6H), 3.68 (t, J=5 Hz, 1H), 3.72 (t, J=5 Hz, 1H), 4.41 (s, 2H), 7.14–7.29 (m, 5H), 7.48 (s, 0.5H), 7.50 (s, 0.5H), 11.90 (s, br, 1H).

Example 4

5-(3-Cyclohexylpropanoyl)-4,5,6,7-tetrahydroimidazo[4,5-c]pyridine

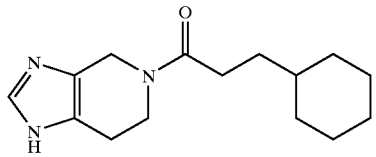

To a solution of carbonyldiimidazole (0.83 g, 5.12 mmol) in DCM (8 mL) 3-cyclohexylpropionic acid (0.80 g, 5.10 mmol) was added dropwise. The mixture was stirred at room temperature for 20 h, and then a solution of 4,5,6,7-tetrahydroimidazo[4,5-c]pyridine (5.10 mmol) in DMF (1 mL) and DCM (1 mL) was added. After stirring for four days DCM (100 mL) was added and the mixture was washed with water (15 mL) and dried (MgSO₄). Concentration and column chromatography (silica gel, ethyl acetate/methanol 9:1) gave 0.66 g (50%) of the title amide as an oil.

¹H NMR (400 MHz, DMSO-d₆, two rotamers, 1:1): δ0.80–0.95 (m, 2H), 1.05–1.30 (m, 4H), 1.90 (m, 2H), 1.56–1.75 (m, 5H), 2.39 (m, 2H), 2.52 (t, J=5 Hz, 1H), 2.61 (t, J=5 Hz, 1H), 3.69 (t, J=5 Hz, 1H), 3.72 (t, J=5 Hz, 1H), 4.42 (s, 2H), 7.51 (s, 0.5H), 7.53 (s, 0.5H), 11.90 (s, br, 1H).

Example 5

5-[3-(4-Fluorophenyl)propanoyl]-4-(4-isopropylphenyl)-4,5,6,7-tetrahydroimidazo[4,5-c]pyridine

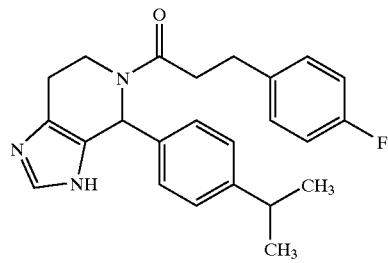

A mixture of histamine dihydrochloride (1.85 g, 10.0 mmol), water (10 mL), potassium hydroxide (1.72 g, 30.0 mmol), ethanol (25 mL) and 4-isopropylbenzaldehyde (1.62 g, 10.91 mmol) was heated to reflux for 1.5 h. Ethanol was evaporated and the residue was diluted with water (40 mL). Extraction (5×25 mL DCM), washing of the combined extracts (2×50 mL brine) and drying (MgSO₄) yielded 2.29 g (87%) of crude 4-(4-isopropylphenyl)-4,5,6,7-tetrahydroimidazo[4,5-c]pyridine, which was used for the next synthetic step without further purification. This amine (0.48 g, 1.99 mmol) was dissolved in DCM (5 mL) and added to a 30 min old mixture of 3-(4-fluorophenyl)propionic acid (0.31 g, 1.84 mmol), HOBt (0.27 g, 1.20 mmol) and EDC (0.42 g, 12.19 mmol) in DCM (10 mL). After 18 h the mixture was washed with water (50 mL), dried (MgSO₄) and concentrated. The crude product was purified by column chromatography (silica gel, gradient elution with DCM/methanol). 0.24 g (33%) of the title amide was obtained.

HPLC (214 nm): elution at 10.21 min. LC-MS: Calcd. for MH⁺: 392; found: 392.

¹H NMR (400 MHz, DMSO-d₆): δ1.18 (d, J=7 Hz, 6H), 2.50–2.94 (m, 7H), 3.05 (m, 1H), 3.95 (m, 1H), 6.48 (s, br, 0.7H), 6.67 (s, br, 0.3H), 6.99–7.35 (m, 8H), 7.55 (s, 1H), 11.90 (s, 1H).

Example 6

5-(3,3-Diphenylpropanoyl)-4,5,6,7-tetrahydroimidazo[4,5-c]pyridine

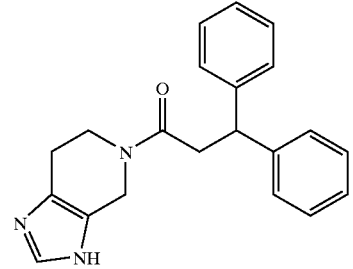

To a suspension of 3,3-diphenylpropionic acid (14 mg, 0.06 mmol) and HOBt (9 mg, 0.07 mmol) in ethyl acetate (1.5 mL) a solution of EDC (12 mg, 0.06 mmol) in ethyl acetate (0.5 mL) was added. The resulting mixture was shaken for 20 min at room temperature and then 4,5,6,7-tetrahydroimidazo[4,5-c]pyridine dihydrochloride (12 mg, 0.06 mmol) and triethylamine (0.02 mL) were added. After shaking for 16 h the mixture was washed with brine (2×2 mL), and the organic phase was concentrated. 12 mg (60%) of the title amide was obtained.

HPLC (214 nm): elution at 8.71 min. LC-MS: Calcd. for MH$^+$: 332; found: 332.

$^1$H NMR (300 MHz, CDCl$_3$, two rotamers, 1:1): δ2.55 (m, 2H), 3.15 (t, J=7 Hz, 2H), 3.61 (t, J=5 Hz, 1H), 3.80 (t, J=5 Hz, 1H), 4.41 (s, 1H), 4.57 (s, 1H), 4.67 (m, 1H), 7.06–7.30 (m, 10H), 7.39 (s, 0.5H), 7.43 (s, 0.5H).

Example 7

5-(3-Cyclohexylpropanoyl)-4-ethyl-4-methyl-4,5,6,7-tetrahydroimidazo-[4,5-c]pyridine Oxalic Acid Salt

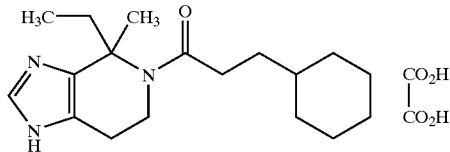

From histamine dihydrochloride (1.85 g, 10.0 mmol), 2-butanone (1.80 g, 25.0 mmol) and 3-cyclohexylpropanoyl chloride (2.0 g, 11.5 mmol) 0.60 g (15%) of the title oxalate was obtained using the General Procedure A.

HPLC (214 nm): elution at 19.54 min. LC-MS: Calcd. for MH$^+$: 304; found: 304.

$^1$H NMR (400 MHz, DMSO-d$_6$, two rotamers, 2:1): δ0.39 (t, J=7 Hz, 2H), 0.79–0.93 (m, 2H), 0.95 (t, J=7 Hz, 1H), 1.05–1.29 (m, 4H), 1.39 (m, 2H), 1.49 (s, 1H), 1.59 (s, 2H), 1.60–2.10 (m, 7H), 2.15–2.50 (m, 1H), 2.60–2.99 (m, 3H), 3.28–3.49 (m, 1.3H), 3.88 (m, 0.7H), 7.69 (s, 0.3H), 8.39 (s, 0.7H).

Example 8

5-[3-(10,11-Dihydro-5H-dibenzo[b,f]azepin-5-yl)propanoyl]4,5,6,7-tetrahydroimidazo[4,5-c]pyridine

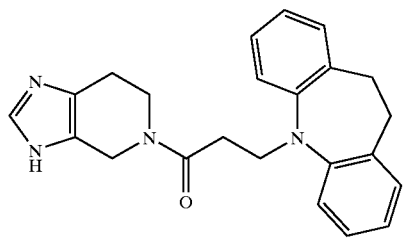

Iminodibenzyl (50.0 g, 0.256 mol) was dissolved in DMF (700 mL), sodium hydride (12.3 g, 0.306 mol, 60% dispersion in oil) was slowly added in portions and the mixture was stirred at 50° C. for 2 h. Ethyl 3-bromopropionate (100 mL, 0.77 mol) was slowly added dropwise and the mixture was heated at reflux temperature overnight. The mixture was cooled and evaporated. The residue was suspended in DCM (150 mL), filtered and the solvent was evaporated. The resulting residue was purified in portions by column chromatography (silica gel, DCM) to give 5.1 g (7%) of 3-(10,11-dihydro-5H-dibenzo[b,f]azepin-5-yl)propionic acid ethyl ester.

TLC: R$_f$=0.69 (silica gel, DCM).

3-(10,11-Dihydro-5H-dibenzo[b,f]azepin-5-yl)propionic acid ethyl ester (1.41 g, 4.77 mmol) was dissolved in ethanol (30 mL) and a solution of sodium hydroxide (0.75 g, 18.8 mmol) in water (5 mL) was added. The mixture was stirred for 3.5 h. 1 N Hydrochloric acid (17 mL) was added and the mixture was extracted with DCM (2×25 mL). The combined organic extracts were washed with brine (50 mL), dried (MgSO$_4$) and the solvent was evaporated to give 1.18 g (92%) of 3-(10,11-dihydro-5H-dibenzo[b,f]azepin-5-yl)propionic acid.

Carbonyldiimidazole (0.33 g, 2.1 mmol) was dissolved in DCM (5 mL) and 3-(10,11-dihydro-5H-dibenzo[b,f]azepin-5-yl)-1-propionic acid (0.56 g, 2.1 mmol) was added. The mixture was stirred at room temperature for 1.5 h under a nitrogen atmosphere. Simultaneously, sodium methoxide (0.8 mL of a 30% solution in water, 4.4 mmol) was added to a solution of 4,5,6,7-tetrahydroimidazo[4,5-c]pyridine dihydrochloride (0.43 g, 2.2 mmol) in methanol (5 mL). The mixture was stirred at room temperature for 1.5 h under a nitrogen atmosphere. The solvent was evaporated and the residue was stripped with DCM (6 mL). The above solution of the activated carboxylic acid was added to the residue and the reaction mixture was stirred at room temperature overnight. Water (10 mL) was added followed by DCM (50 mL) and the phases were separated. The aqueous phase was extracted with DCM (20 mL) and the combined organic phases were dried (MgSO$_4$). After evaporation of the solvent, the residue was purified by column chromatography (silica gel, 150 mL, methanol/ethyl acetate 1:5). Evaporation of the solvent afforded 0.41 g (52%) of the title compound as a solid.

TLC: R$_f$=0.28 (silica gel, methanol/ethyl acetate 1:5). LC-MS: Calcd. for MH$^+$: 373; found: 373.

$^1$H NMR (400 MHz, DMSO-d$_6$, two rotamers, 1:1): δ2.49 (m, 1H), 2.60–2.72 (m, 3H), 3.07 (d, 4H), 3.47 (t, 1H), 3.86 (t, 1H), 4.08–4.20 (m, 2H), 4.22 (s, 1H), 4.62 (s, 1H), 6.90 (m, 2H), 7.01–7.16 (m, 6H), 7.40 (s, 0.5H), 7.45 (s, 0.5H).

Example 9

5-(3-Cyclohexylpropanoyl)-4,5,6,7-tetrahydroimidazo[4,5-c]pyridine-4-spirocyclobutane Oxalic Acid Salt

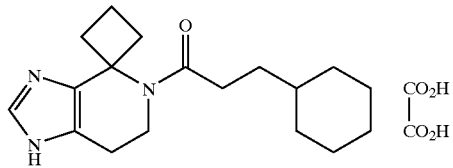

From histamine dihydrochloride (1.85 g, 10.0 mmol), cyclobutanone (1.75 g, 25.0 mmol) and 3-cyclohexylpropanoyl chloride (2.0 g, 11.5 mmol), 0.70 g (18%) of the title oxalate was obtained (General Procedure A).

HPLC (214 nm): elution at 19.40 min. LC-MS: Calcd. for MH$^+$: 302; found: 302.

$^1$H NMR (400 MHz, DMSO-d$_6$): δ0.75–0.95 (m, 2H), 1.04–1.28 (m, 4H), 1.35 (q, J=7 Hz, 2H), 1.50–2.70 (m, 11H), 3.63 (t, J=5 Hz, 2H), 8.22 (s, br, 1H).

Example 10

Parallel Synthesis of Ureas

To each reactor of an array of 12 reactors, each containing a solution of 4,5,6,7-tetrahydroimidazo[4,5-c]pyridine dihydrochloride (0.07 mmol) in DMF (0.5 mL, containing 5% triethylamine) a solution of one isocyanate (0.9 equivalents) selected from 12 different isocyanates in 1,2-dichloroethane (0.2 mL) was added. The resulting mixtures were shaken overnight at room temperature. Concentration under reduced pressure gave the corresponding ureas. Using this methodology the following ureas were prepared:

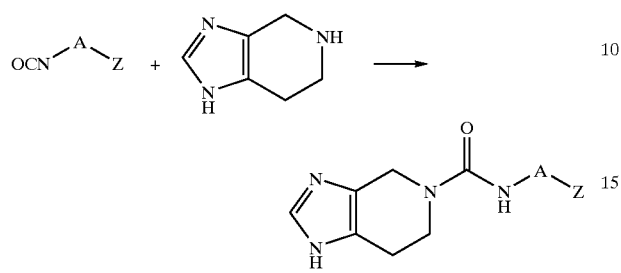

| Example | Z-A- | MH⁺ (calcd) | MH⁺ (found) |
|---|---|---|---|
| 10-001 | 2-(2-thienyl)ethyl | 277 | 277 |
| 10-002 | 3,5-dimethyl-1,2-oxazol-4-yl | 262 | 262 |
| 10-003 | 1-(1-naphthyl)ethyl | 321 | |
| 10-004 | (2-phenylcyclopropyl) | 283 | 283 |
| 10-005 | 1-(4-brompphenyl)ethyl | 350 | |
| 10-006 | 2-(trifluoromethyl)phenyl | 311 | 311 |
| 10-007 | 2-phenylethyl | 271 | 271 |
| 10-008 | 4-(trifluoromethyl)phenyl | 311 | 311 |
| 10-009 | 3-cyanophenyl | 268 | 268 |
| 10-010 | 4-cyanophenyl | 268 | 268 |
| 10-011 | n-octyl | 279 | 279 |

Example 11

5-(2,4-Dichlorobenzylaminocarbonyl)-4,5,6,7-tetrahydroimidazo[4,5-c]pyridine

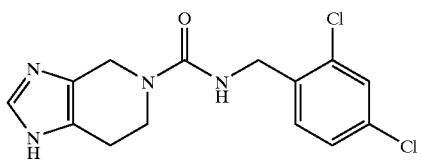

To a mixture of 4,5,6,7-tetrahydroimidazo[4,5-c]pyridine dihydrochloride (0.50 g, 2.55 mmol), ethanol (10 mL) and triethylamine (1.10 mL, 7.89 mmol), 2,4-dichlorobenzyl isocyanate (0.52 g, 2.57 mmol) was added. The resulting mixture was stirred at room temperature for 16 h and then concentrated under reduced pressure. The residue was distributed between water (20 mL) and ethyl acetate (75 mL). The organic phase was washed with water (10 mL) and brine (10 mL), dried (MgSO₄) and concentrated under reduced pressure. The residue was triturated in diethylether (50 mL) and the crude product was filtered off. Recrystallization from acetone (25 mL) gave 0.30 g (37%) of the title urea as a colourless solid.

HPLC (214 nm): elution at 7.97 min. LC-MS: Calcd. for MH⁺: 325; found: 325.

¹H NMR (400 MHz, DMSO-d₆): δ2.56 (s, br, 2H), 3.65 (t, J=6 Hz, 2H), 4.29 (d, J=6 Hz, 2H), 4.34 (s, 2H), 7.20 (s, br, 1H), 7.29 (d, J=8 Hz, 1H), 7.39 (dd, J=8, 1 Hz, 1H), 7.47 (s, 1H), 7.56 (d, J=1 Hz, 1H), 11.79 (s, br, 1H).

Example 12

4-(2-Cyclohexylethyl)-5-(ethylaminocarbonyl)-4,5,6,7-tetrahydroimidazo[4,5-c]pyridine

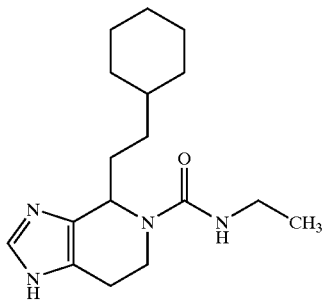

To a solution of histamine dihydrochloride (1.84 g, 10.0 mmol) in water (5 mL) methanol (40 mL) was added. To this stirred mixture an aqueous 12 N sodium hydroxide solution (4.2 mL, 50.4 mmol) and 3-(cyclohexyl)propionaldehyde (3.5 g, 25 mmol) were added. The resulting mixture was heated at reflux temperature for 20 h. Concentrated hydrochloric acid was added until pH 1 and the mixture was diluted with water (100 mL). The mixture was washed with diethyl ether (3×25 mL) and the aqueous solution was concentrated under reduced pressure. The residue was suspended in methanol (150 mL) and the suspension was filtered. The filtrate was concentrated under reduced pressure to give a residue which was treated with warm ethanol (75 mL). The resulting mixture was filtered and the filtrate was concentrated under reduced pressure to a volume of approximately 10 mL. Acetone (50 mL) was added and the mixture was left for crystallization. The solid was isolated by filtration and dried under reduced pressure to give 2.4 g of a solid which was dissolved in water (10 mL). While stirring, an aqueous 1 N sodium hydroxide solution was added until pH 11–12. The resulting mixture was extracted with ethyl acetate (200 mL), the extracts were dried (MgSO₄) and the solvent was evaporated under reduced pressure. This afforded 1.25 g of 4-(2-cyclohexylethyl)-4,5,6,7-tetrahydroimidazo[4,5-c]-pyridine.

To a solution of the above amine (0.45 g, 1.9 mmol) in ethanol (10 mL), triethylamine (0.2 g, 1.9 mmol) and ethyl isocyanate (0.14 g, 1.9 mmol) were added. The mixture was stirred overnight at room temperature and then concentrated under reduced pressure. The crude product was purified by column chromatography (silica gel, elution with ethyl acetate/methanol 9:1). This afforded 0.14 g (24% calculated from the amine) of the title compound as a solid.

M.p. 210–212° C. ¹H NMR (400 MHz, DMSO-d₆): δ0.85 (m, 2H), 1.00 (t, 3H), 1.05–1.45 (m, 6H), 1.50–1.75 (m, 7H), 2.35 (m, 1H), 2.55 (m, 1H), 3.03 (m, 3H), 4.10 (m, br, 1H), 4.85 (m, br, 1H), 6.38 (s, br, 1H), 7.40 (s, 1H), 11.68 (s, br, 1H).

Example 13

4-(2-Cyclohexylethyl)-5-(2,4-dichlorobenzylaminocarbonyl)-4,5,6,7-tetrahydroimidazo[4,5-c]pyridine

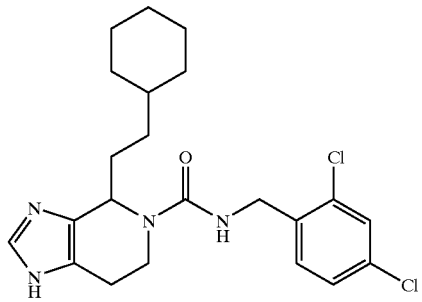

To a solution of 4-(2-cyclohexylethyl)-4,5,6,7-tetrahydroimidazo[4,5-c]pyridine (0.47 g, 2.0 mmol, prepared as described in Example 13) in ethanol (10 mL), triethylamine (0.28 ml, 2.0 mmol) and 2,4-dichlorobenzyl isocyanate (0.41 g, 2.0 mmol) were added dropwise. The mixture was stirred overnight at room temperature and then concentrated under reduced pressure. The residue was re-evaporated with acetone and then dissolved in acetone (15 mL) and left for crystallization. The solid was isolated by filtration, washed with acetone and dried. This afforded 0.60 g (69%) of the title compound as a solid.

M.p. 185–187° C. $^1$H NMR (400 MHz, DMSO-$d_6$): δ0.85 (m, 2H), 1.05–1.45 (m, 6H), 1.52–1.70 (m, 7H), 2.42 (m, 1H), 2.60 (m, 1H), 3.09 (m, 1H), 4.18 (m, br, 1H), 4.28 (m, 2H), 4.96 (m, br, 1H), 7.10 (t, br, 1H), 7.28 (d, 1H), 7.38 (dd, 1H), 7.43 (s, 1H), 7.55 (d 1H), 11.75 (s, br, 1H).

Example 14

Parallel Synthesis of Carboxamides

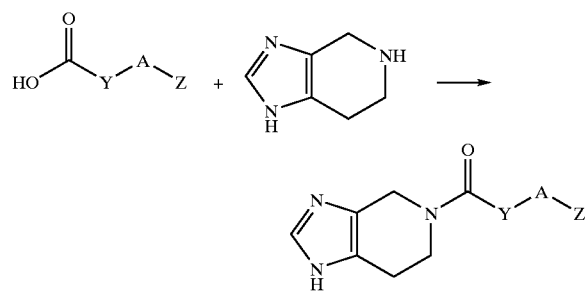

To each reactor in an array of six, a suspension of HOBt (7.4 mg, 55 μmol) in a mixture of acetonitrile, 1,2-dichloroethane, NMP and DMSO (250 μL) was added. Then a suspension of EDC (11.5 mg, 60 μmol) in a mixture of acetonitrile, 1,2-dichloroethane, NMP and DMSO (250 μL) was added to each reactor. To each reactor a carboxylic acid (50 μmol, Z—A—Y— as listed below) dissolved in 1,2-dichloroethane (3 mL) was added and the array was shaken for 15 min. To each reactor 4,5,6,7-tetrahydroimidazo[4,5-c]pyridine (60 μmol, prepared according to General Procedure B) dissolved in a mixture of acetonitrile (250 μL) and triethylamine (210 μL, 300 μmol) was added and the array was shaken overnight. 1,2-Dichloroethane (1 mL) was added to each reactor and the array was shaken for 2 h. A 0.3 N hydrochloric acid solution (500 μL) was added to each reactor and the array was shaken for 2 h. The lower phase of each reactor was isolated with a pipette and concentrated under reduced pressure. This afforded the following six amides, identified by their MH$^+$ (LC-MS):

| Example | Z-A-Y- | MH* (calcd) | MH* (found) |
|---|---|---|---|
| 14-001 | cyclohexyl-(CH$_2$)$_2$- | 262 | 262 |
| 14-002 | cyclohexyl-CH$_2$- | 248 | 248 |
| 14-003 | cyclohexyl- | 234 | |
| 14-004 | 4-F-C$_6$H$_4$-C(O)-(CH$_2$)$_2$- | 302 | |
| 14-005 | 4-F-C$_6$H$_4$-C(O)-(CH$_2$)$_3$- | 326 | |
| 14-006 | C$_6$H$_5$-(CH$_2$)$_3$- | 298 | 298 |

Example 15

4,5,6,7-Tetrahydroimidazo[4,5-c]pyridine-5-carboxylic Acid 4-tert-butylbenzyl Ester Oxalate

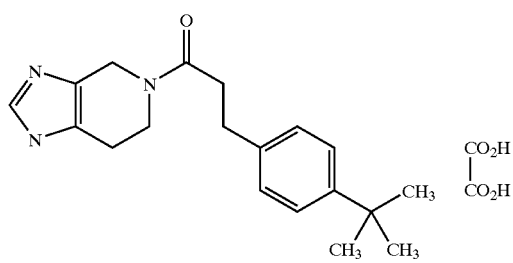

To a solution of 4-tert-butylbenzyl alcohol (1.97 g, 12 mmol) in DCM (30 mL) was added pyridine (1.3 mL) and then a solution of 4-nitrophenyl chloroformate (1.57 g, 7.8 mmol) in DCM (20 mL). The mixture was stirred at room temperature for 1 h, concentrated under reduced pressure, and to the residue was added a mixture of of 4,5,6,7-tetrahydromidazo[4,5-c]pyridine (1.5 g, 7 mmol), methanol (3.3 mL), DMF (30 mL), and diisopropylethylamine (4.1 mL). The resulting mixture was stirred at room temperature overnight and concentrated under reduced pressure. The residue was distributed between water and ethyl acetate, phases were separated, and the organic layer was washed with water, dried (MgSO$_4$), and filtered. A solution of oxalic acid (0.63 g) in ethyl acetate was added to the filtrate and the mixture was allowed to stand for 24 h. Filtration yielded the title compound as colorless solid.

$^1$H NMR (400 MHz, DMSO-d$_6$) δ 1.28 (s, 9H), 2.65 (m, 2H), 3.69 (t, J=5 Hz, 2H), 4.46 (s, 2H), 5.08 (s, 2H), 7.31 (d, J=8 Hz, 2H), 7.39 (d, J=8 Hz, 2H), 8.13 (m, 1H).

(C$_{18}$H$_{23}$N$_3$O$_2$, C$_2$H$_2$O$_4$); calcd. 59.54C 6.25H 10.42N; found 59.66C 6.28H 10.35N.

The compound was prepared from 4,5,6,7-tetrahydro-1H-imidazo[4,5-c]pyridine and 4-(tert-butyl)benzyl alcohol.

$^1$H NMR (400 MHz, DMSO-d$_6$) δ 1.28 (s, 9H), 2.65 (m, 2H), 3.69 (t, J=5 Hz, 2H), 4.46 (s, 2H), 5.08 (s, 2H), 7.31 (d, J=8 Hz, 2H), 7.39 (d, J=8 Hz, 2H), 8.13 (m, 1H).

(C$_{18}$H$_{23}$N$_3$O$_2$, C$_2$H$_2$O$_4$); calcd. 59.54C 6.25H 10.42N; found 59.66C 6.28H 10.35N.

Using the same procedure as described for the above example the following compounds were prepared:

Example 16

1,4,6,7-Tetrahydro-Imidazo[4,5-c]pyridine-5-carboxylic Acid Benzyl Ester

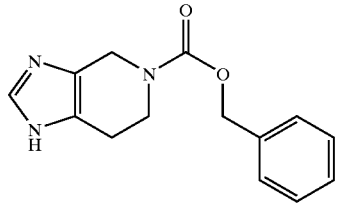

Example 17

4,5,6,7-Tetrahydroimidazo[4,5-c]pyridine-5-carboxylic Acid 2,3-dimethylbenzyl Ester Oxalate

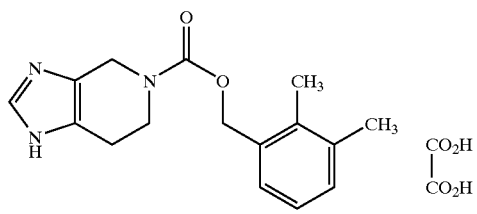

The compound was prepared from 4,5,6,7-tetrahydro-1H-imidazo[4,5-c]pyridine and 2,3-dimethylbenzyl alcohol.

$^1$H NMR (400 MHz, DMSO-d$_6$) δ2.19 (s, 3H), 2.27 (s, 3H), 2.63 (m, 2H), 3.70 (t, J=6 Hz, 2H), 4.46 (s, 2H), 5.12 (s, 2H), 7.04–7.18 (m, 3H), 8.15 (s, br, 1H).

Example 18

4,5,6,7-Tetrahydroimidazo[4,5-c]pyridine-5-carboxylic Acid 2-phenylbutyl Ester Oxalate

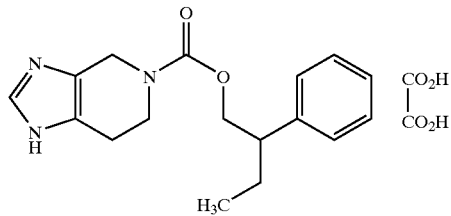

The compound was prepared from 4,5,6,7-tetrahydro-1H-imidazo[4,5-c]pyridine and 2-phenyl-1-butanol oxalate.

M.p. 154–156° C. $^1$H NMR (400 MHz, DMSO-d$_6$) δ0.76 (t, J=7 Hz, 3H), 1.53–1.66 (m, 1H), 1.70–1.80 (m, 1H), 2.40–2.63 (m, 2H), 2.82 (m, 1H), 3.48–3.65 (m, 2H), 4.11–4.22 (m, 2H), 4.25–4.40 (m, 2H), 7.18–7.34 (m, 5H), 8.09 (s, 1H).

Calcd. 58.60C 5.95H 10.79N; found 58.89C 5.93H 10.63N.

Example 19

4,5,6,7-Tetrahydroimidazo[4,5-c]pyridine-5-carboxylic Acid 3-methoxybenzyl Ester Oxalate

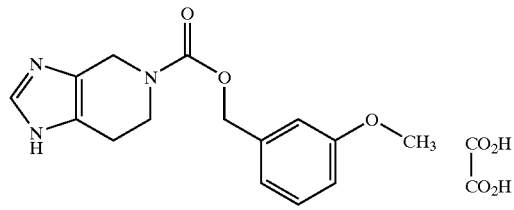

The compound was prepared from 4,5,6,7-tetrahydro-1H-imidazo[4,5-c]pyridine and 2-phenyl-1-butanol oxalate.

M.p. 163–165° C. $^1$H NMR (400 MHz, DMSO-d$_6$) δ2.65 (t, J=5 Hz, 2H), 3.69–3.75 (m, 5H), 4.48 (m, 2H), 5.09 (s, 2H), 6.87–6.95 (m, 3H), 7.29 (t, J=8 Hz, 1H), 8.12 (s, 1H).

(C$_{15}$H$_{17}$N$_3$O$_3$, C$_2$H$_2$O$_4$); calcd. 54.11C 5.08H 11.14N; found 53.90C 5.04H 11.09N.

Example 20

4,5,6,7-Tetrahydroimidazo[4,5-c]pyridine-5-carboxylic Acid Cyclopentylmethyl Ester Oxalate

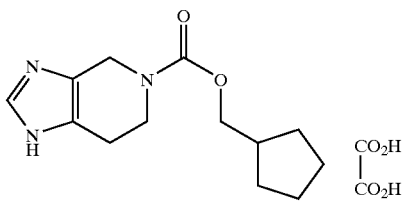

The compound was prepared from 4,5,6,7-tetrahydro-1H-imidazo[4,5-c]pyridine and cyclopentylmethanol.

$^1$H NMR (400 MHz, DMSO-d$_6$) δ1.22 (m, 2H), 1.45–1.61 (m, 4H), 1.62–1.75 (m, 2H), 2.16 (sept, J=7 Hz, 1H), 2.63

(m, 2H), 3.68 (t, J=5 Hz, 2H), 3.92 (d, J=7 Hz, 2H), 4.44 (s, 2H), 8.16 (s, 1H).

Example 21

4,5,6,7-Tetrahydroimidazo[4,5-c]pyridine-5-carboxylic Acid 3-methylbenzyl Ester Oxalate

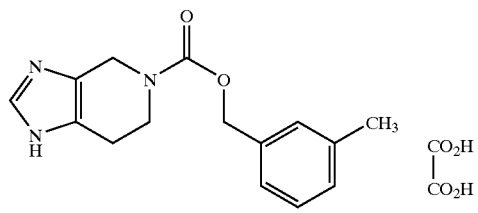

The compound was prepared from 4,5,6,7-tetrahydro-1H-imidazo[4,5-c]pyridine and 3-methylbenzyl alcohol.

M.p. 169–171° C. $^1$H NMR (400 MHz, DMSO-$d_6$) δ2.31 (s, 3H), 2.65 (m, 2H), 3.70 (m, 2H), 4.47 (s, 2H), 5.08 (s, 2H), 7.11–7.19 (m, 3H), 7.26 (t, J=8 Hz, 1H), 8.15 (s, 1H).

($C_{15}H_{17}N_3O_2$, $C_2H_2O_4$); calcd. 56.51C 5.30H 11.63N; found 56.74C 5.29H 11.63N.

Example 22

4,5,6,7-Tetrahydroimidazo[4,5-c]pyridine-5-carboxylic Acid 2-methylbenzyl Ester Oxalate

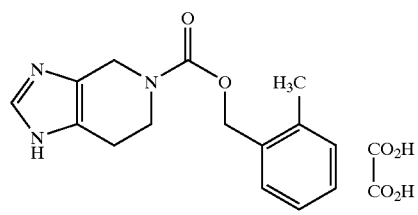

The compound was prepared from 4,5,6,7-tetrahydro-1H-imidazo[4,5-c]pyridine and 2-methylbenzyl alcohol.

M.p. 158–160° C. $^1$H NMR (400 MHz, DMSO-$d_6$) δ2.31 (s, 3H), 2.64 (s, 2H), 3.69 (t, J=5 Hz, 2H), 4.46 (s, 2H), 5.12 (s, 2H), 7.15–7.26 (m, 3H), 7.31 (d, J=8 Hz, 1H), 8.14 (s, 1H).

Calcd. 56.51C 5.30H 11.63N; found 56.38C 5.27H 11.43N.

Example 23

4,5,6,7-Tetrahydroimidazo[4,5-c]pyridine-5-carboxylic Acid 2-(2-methoxyphenyl)ethyl Ester Oxalate

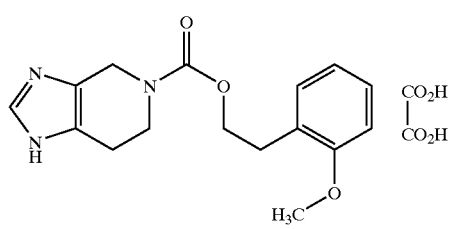

The compound was prepared from 4,5,6,7-tetrahydro-1H-imidazo[4,5-c]pyridine and 2-(2-methoxyphenyl)-1-ethanol.

M.p. 165–167° C. $^1$H NMR (400 MHz, DMSO-$d_6$) δ2.53–2.63 (m, 2H), 2.88 (t, J=5 Hz, 2H), 3.61 (s, br, 2H), 3.77 (s, 3H), 4.19 (t, J=7 Hz, 2H), 4.39 (s, br, 2H), 6.85 (s, br, 1H), 6.95 (d, J=8 Hz, 1H), 7.10–7.24 (m, 2H), 8.15 (s, 1H).

Calcd. 55.24C 5.41H 10.74N; found 55.39C 5.39H 10.62N.

Example 24

4,5,6,7-Tetrahydroimidazo[4,5-c]pyridine-5-carboxylic Acid 2-(3-methylphenyl)ethyl Ester Oxalate

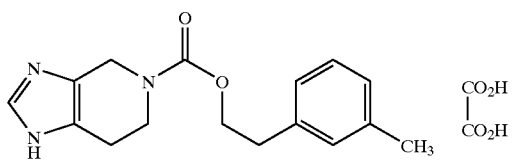

The compound was prepared from 4,5,6,7-tetrahydro-1H-imidazo[4,5-c]pyridine and 2-(3-methylphenyl)-1-ethanol.

M.p. 155–157° C. $^1$H NMR (400 MHz, DMSO-$d_6$) δ2.27 (s, 3H), 2.52–2.65 (m, 2H), 2.85 (t, J=5 Hz, 2H), 3.63 (s, br, 2H), 4.21 (t, J=5 Hz, 2H), 4.40 (s, 2H), 7.02 (m, 3H), 7.18 (s, br, 1H), 8.16 (s, 1H).

($C_{16}H_{19}N_3O_2$, $C_2H_2O_4$); calcd. 57.59C 5.64H 11.19N; found 57.33C 5.64H 11.13N.

Example 25

4,5,6,7-Tetrahydro-imidazo[4,5-c]pyridine-5-carboxylic Acid adamantan-1-ylmethyl Ester Oxalate

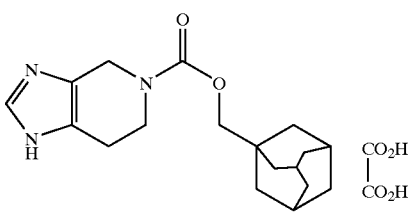

The compound was prepared from 4,5,6,7-tetrahydro-1H-imidazo[4,5-c]pyridine and 1-adamantylmethanol.

M.p. 212–214° C. $^1$H NMR (400 MHz, DMSO-$d_6$) δ1.51 (s, 6H), 1.58–1.72 (m, 6H), 1.94 (s, br, 3H), 2.64 (s, br, 2H), 3.63–3.73 (m, 4H), 4.44 (m, 2H), 8.13 (s, br, 1H).

Example 26

4,5,6,7-Tetrahydroimidazo[4,5-c]pyridine-5-carboxylic Acid 3,4-dimethylbenzyl Ester Oxalate

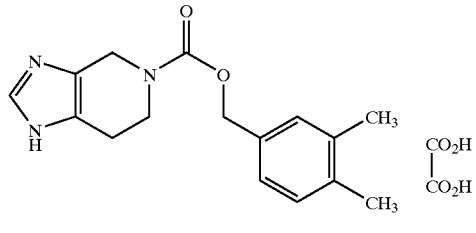

The compound was prepared from 4,5,6,7-tetrahydro-1H-imidazo[4,5-c]pyridine and 3,4-dimethylbenzyl alcohol.

M.p. 193–195° C. $^1$H NMR (400 MHz, DMSO-d$_6$) δ2.20 (s, 6H), 2.62 (m, 2H), 3.69 (m, 2H), 4.45 (s, 2H), 5.03 (s, 2H), 7.05–7.14 (m, 3H), 8.12 (s, br, 1H).

Calcd. 57.59C 5.64H 11.19N; found 57.76C 5.60H 10.90N.

Example 27

4,5,6,7-Tetrahydroimidazo[4,5-c]pyridine-5-carboxylic Acid cyclohex-3-enylmethyl Ester Oxalate

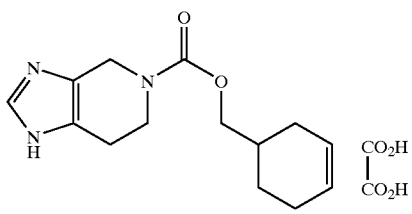

The compound was prepared from 4,5,6,7-tetrahydro-1H-imidazo[4,5-c]pyridine and cyclohexen-4-ylmethanol.

$^1$H NMR (400 MHz, DMSO-d$_6$) δ 1.26 (m, 1H), 1.70–1.80 (m, 2H), 1.82–1.92 (m, 1H), 1.98–2.10 (m, 3H), 2.63 (t, J=5 Hz, 2H), 3.68 (t, J=5 Hz, 2H), 3.94 (d, J=7 Hz, 2H), 4.143 (s, br, 2H), 5.65 (m, 2H), 8.10 (s, br, 1H).

Example 28

4,5,6,7-Tetrahydroimidazo[4,5-c]pyridine-5-carboxylic Acid 2,4-dimethylbenzyl Ester Oxalate

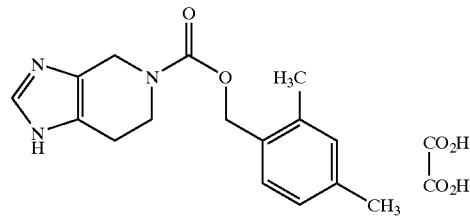

The compound was prepared from 4,5,6,7-tetrahydro-1H-imidazo[4,5-c]pyridine and 2,4-dimethylbenzylalcohol.

M.p. 176–178° C. $^1$H NMR (400 MHz, DMSO-d$_6$) δ2.26 (s, 6H), 2.62 (m, 2H), 3.68 (m, 2H), 4.43 (s, 2H), 5.08 (s, 2H), 6.98 (d, J=8 Hz, 1H), 7.02 (s, 1H), 7.19 (d, J=8 Hz, 1H), 8.09 (s, br, 1H).

($C_{16}H_{19}N_3O_2$, $C_2H_2O_4$); calcd. 57.59C 5.64H 11.19N; found 57.51C 5.63H 11.19N.

Example 29

4,5,6,7-Tetrahydroimidazo[4,5-c]pyridine-5-carboxylic Acid 2-(2-methylphenyl)ethyl Ester Oxalate

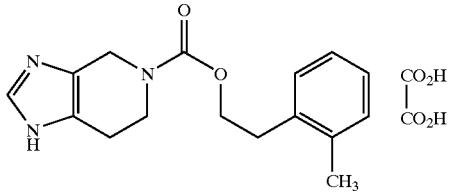

The compound was prepared from 4,5,6,7-tetrahydro-1H-imidazo[4,5-c]pyridine and 2-(2-methylphenyl)ethanol.

$^1$H NMR (400 MHz, DMSO-d$_6$) δ2.29 (s, 3H), 2.59 (s, br, 2H), 2.91 (m, 2H), 3.63 (s, br, 2H), 4.21 (t, J=5 Hz, 2H), 4.41 (s, 2H), 7.06–7.20 (m, 4H), 8.15 (s, 1H).

($C_{16}H_{19}N_3O_2$, $C_2H_2O_4$); calcd. 57.59C 5.64H 11.19N; found 57.44C 5.63H 11.16N.

Example 30

4,5,6,7-Tetrahydroimidazo[4,5-c]pyridine-5-carboxylic Acid naphthalen-1-ylmethyl Ester Oxalate

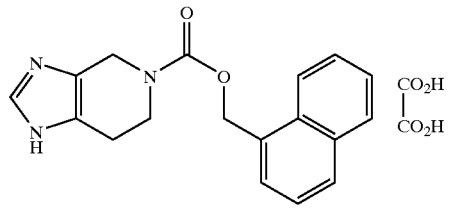

The compound was prepared from 4,5,6,7-tetrahydro-1H-imidazo[4,5-c]pyridine and 1-naphthylmethanol.

$^1$H NMR (400 MHz, DMSO-d$_6$) δ2.52–2.68 (m, 2H), 3.69 (m, 2H), 4.43 (m, 2H), 5.58 (s, 2H), 7.46–7.62 (m, 4H), 7.92–8.00 (m, 2H), 8.05–8.15 (m, 2H).

Example 31

4,5,6,7-Tetrahydroimidazo[4,5-c]pyridine-5-carboxylic Acid 4-isopropylbenzyl Ester Oxalate

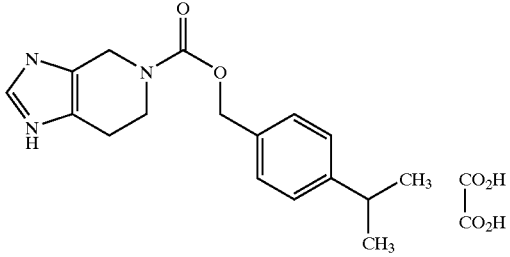

The compound was prepared from 4,5,6,7-tetrahydro-1H-imidazo[4,5-c]pyridine and 4-isopropylbenzyl alcohol.

M.p. 166–168° C. $^1$H NMR (400 MHz, DMSO-d$_6$) δ1.19 (d, J=7 Hz, 6H), 2.64 (m, 2H), 2.89 (sept, J=7 Hz, 1H), 3.70 (t, J=5 Hz, 2H), 4.46 (s, br, 2H), 5.07 (s, 2H), 7.23 (d J=8 Hz, 2H), 7.29 (d, J=8 Hz, 2H), 8.18 (s, br, 1H).

(C$_{17}$H$_{23}$N$_3$O$_2$, C$_2$H$_2$O$_4$); calcd. 58.60C 5.95H 10.79N; found 58.71C 5.97H 10.76N.

Example 32

4,5,6,7-Tetrahydroimidazo[4,5-c]pyridine-5-carboxylic Acid naphthalen-2-ylmethyl Ester Oxalate

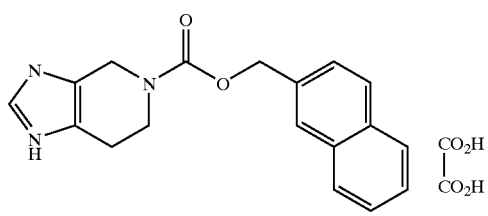

The compound was prepared from 4,5,6,7-tetrahydro-1H-imidazo[4,5-c]pyridine and 2-naphthylmethanol.

M.p. 189–191° C. $^1$H NMR (400 MHz, DMSO-d$_6$) δ2.67 (m, 2H), 3.64 (m, 2H), 4.43–4.60 (m, 2H), 5.79 (s, 2H), 7.52–7.56 (m, 3H), 7.89–8.95 (m, 4H), 8.18 (s, br, 1H).

Calcd. 60.45C 4.82H 10.57N; found 60.33C 4.82H 10.53N.

Example 33

4,5,6,7-Tetrahydroimidazo[4,5-c]pyridine-5-carboxylic Acid 2-methylbiphenyl-3-ylmethyl Ester Oxalate

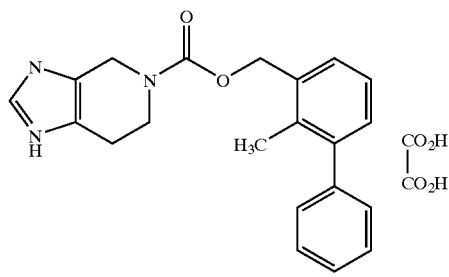

The compound was prepared from 4,5,6,7-tetrahydro-1H-imidazo[4,5-c]pyridine and 2-methylbiphenyl-3-ylmethanol.

M.p. 151–153° C. $^1$H NMR (400 MHz, DMSO-d$_6$) δ2.18 (s, 3H), 2.68 (m, 2H), 3.71 (m, 2H), 4.48 (s, br, 2H), 5.19 (s, 2H), 7.18–7.48 (m, 8H), 8.16 (s, br, 1H).

(C$_{23}$H$_{23}$N$_3$O$_6$,2/3H$_2$O); calcd. 61.46C 5.46H 9.35N; found 61.62C 5.42H 8.94N.

Example 34

4,5,6,7-Tetrahydroimidazo[4,5-c]pyridine-5-carboxylic Acid 4-ethylbenzyl Ester Oxalate

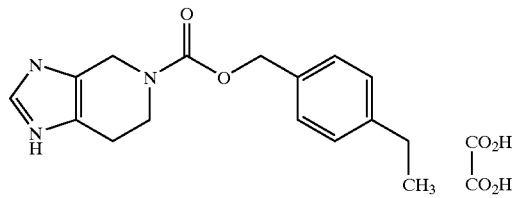

The compound was prepared from 4,5,6,7-tetrahydro-1H-imidazo[4,5-c]pyridine and 4-ethylbenzyl alcohol.

M.p. 171–173° C. $^1$H NMR (400 MHz, DMSO-d$_6$) δ1.17 (t, J=7 Hz, 3H), 2.55–2.68 (m, 4H), 3.69 (t, J=5 Hz, 2H), 4.45 (s, br, 2H), 5.08 (s, 2H), 7.20 (d, J=8 Hz, 2H), 7.29 (d, J=8 Hz, 2H), 8.11 (s, br, 1H).

(C$_{16}$H$_{19}$N$_3$O$_2$, C$_2$H$_2$O$_4$); calcd. 57.59C 5.64H 11.19N; found 57.48C 5.61H 11.20N.

Example 35

4,5,6,7-Tetrahydroimidazo[4,5-c]pyridine-5-carboxylic Acid thiophen-2-ylmethyl Ester Oxalate

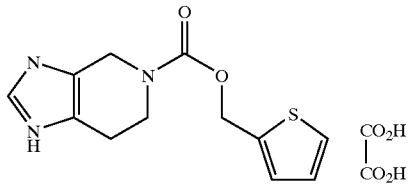

The compound was prepared from 4,5,6,7-tetrahydro-1H-imidazo[4,5-c]pyridine and 2-thienylmethanol.

$^1$H NMR (400 MHz, DMSO-d$_6$) δ2.63 (s, br, 2H), 3.68 (s, br, 2H), 4.43 (s, 2H), 5.28 (s, 2H), 7.01 (m, 1H), 7.17 (d, J=3 Hz, 1H), 7.54 (d, J=5 Hz, 1H), 8.10 (m, 1H).

Example 36

4,5,6,7-Tetrahydroimidazo[4,5-c]pyridine-5-carboxylic Acid 2-thiophen-2-ylethyl Ester Oxalate

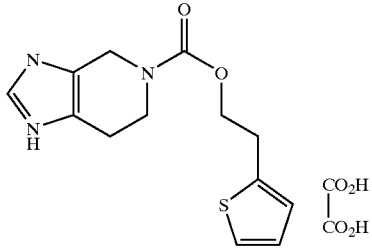

The compound was prepared from 4,5,6,7-tetrahydro-1H-imidazo[4,5-c]pyridine and 2-(2-thienyl)-1-ethanol.

M.p. 173–175° C. $^1$H NMR (400 MHz, DMSO-d$_6$) δ2.62 (s, br, 2H), 3.13 (t, J=7 Hz, 2H), 3.68 (t, J=5 Hz, 2H), 4.21 (t, J=7 Hz, 2H), 4.43 (s, br, 2H), 6.89–6.99 (m, 2H), 7.34 (s, br, 1H), 8.11 (s, br, 1H).

(C$_{13}$H$_{15}$N$_3$O$_2$S): calcd. 49.04C 4.66H 11.44N; found 49.12C 4.62H 11.43N.

Example 37

4,5,6,7-Tetrahydroimidazo[4,5-c]pyridine-5-carboxylic Acid 2-thiophen-3-ylethyl Ester Oxalate

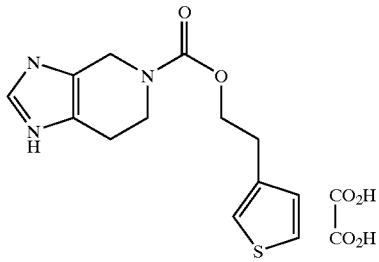

The compound was prepared from 4,5,6,7-tetrahydro-1H-imidazo[4,5-c]pyridine and 2-(3-thienyl)-1-ethanol.

M.p. 193–194° C. $^1$H NMR (400 MHz, DMSO-d$_6$) δ2.59 (s, br, 2H), 2.93 (t, J=7 Hz, 2H), 3.63 (s, br, 2H), 4.21 (t, J=7 Hz, 2H), 4.40 (s, 2H), 7.03 (s, br, 1H), 7.24 (s, br, 1H), 7.46 (s, br, 1H), 8.08 (s, br, 1H).

($C_{13}H_{15}N_3O_2S$); calcd. 49.04C 4.66H 11.44N; found 49.12C 4.61H 11.40N.

Example 38

4,5,6,7-Tetrahydro-imidazo[4,5-c]pyridine-5-carboxylic Acid 4-methoxy-2,3-dimethylbenzyl Ester Oxalate

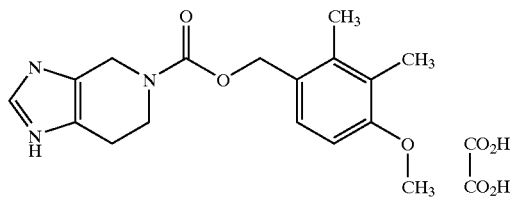

The compound was prepared from 4,5,6,7-tetrahydro-1H-imidazo[4,5-c]pyridine and 2,3-dimethyl-4-methoxybenzyl alcohol.

M.p. 161–162° C. $^1$H NMR (400 MHz, DMSO-d$_6$) δ2.09 (s, 3H), 2.20 (s, 3H), 2.62 (s, br, 2H), 3.65 (s, br, 2H), 3.77 (s, 3H), 4.42 (s, br, 2H), 5.08 (s, 2H), 6.78 (d, J=8 Hz, 1H), 7.15 (d, J=8 Hz, 1H), 8.18 (s, br, 1H).

Example 39

4-Trifluoromethyl-4,5,6,7-tetrahydroimidazo[4,5-c]pyridine-5-carboxylic Acid Benzyl Ester Oxalate

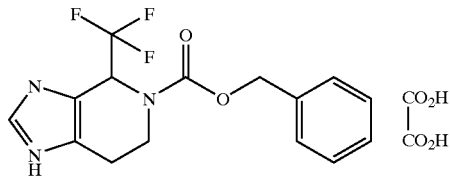

The compound was prepared from 4-trifluoromethyl-4,5,6,7-tetrahydro-1H-imidazo[4,5-c]pyridine and benzyl alcohol.

M.p. 169–171° C. $^1$H NMR (400 MHz, DMSO-d$_6$) δ2.65–2.81 (m, 2H), 2.99 (s, br, 2H), 4.42 (q, J=8 Hz, 1H), 5.42 (s, 2H), 7.36–7.45 (m, 3H), 7.51 (d, J=8 Hz, 2H), 8.21 (s, 1H), 1H).

Example 40

4,5,6,7-Tetrahydroimidazo[4,5-c]pyridine-5-carboxylic Acid 2-cyclohexylethyl Ester Oxalate

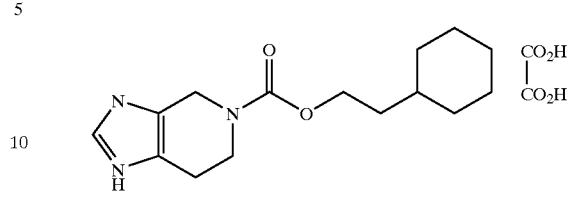

The compound was prepared from 4,5,6,7-tetrahydro-1H-imidazo[4,5-c]pyridine and 2-cyclohexyl-1-ethanol.

M.p. 174–176° C. $^1$H NMR (400 MHz, DMSO-d$_6$) δ0.83–0.95 (m, 2H), 1.05–1.26 (m, 3H), 1.32 (m, 1H), 1.48 (q, J=7 Hz, 2H), 1.55–1.71 (m, 5H), 2.64 (m, 2H), 3.67 (t, J=5 Hz, 2H), 4.06 (t, J=7 Hz, 2H), 4.44 (s, 2H), 8.22 (s, br, 1H).

($C_{15}H_{23}N_3O_2$); calcd. 55.58C 6.86H 11.40N; found 55.70C 6.90H 11.32N.

Example 41

4,5,6,7-Tetrahydroimidazo[4,5-c]pyridine-5-carboxylic Acid Cyclohexylmethyl Ester Oxalate

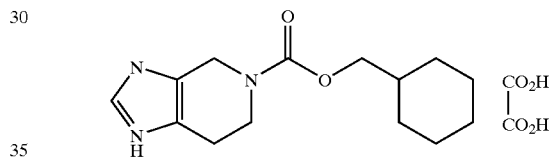

The compound was prepared from 4,5,6,7-tetrahydro-1H-imidazo[4,5-c]pyridine and cyclohexylmethanol.

M.p. 176–178° C. $^1$H NMR (400 MHz, DMSO-d$_6$) δ0.89–1.03 (m, 2H), 1.06–1.29 (m, 3H), 1.55–1.72 (m, 6H), 2.65 (m, 2H), 3.68 (m, 2H), 3.86 (d, J=7 Hz, 2H), 4.44 (s, br, 2H), 8.20 (s, br, 1H).

($C_{14}H_{21}N_3O_2$, $C_2H_2O_4$) calcd. 54.38C 6.56H 11.89N; found 54.56C 6.64H 11.77N.

Example 42

4,5,6,7-Tetrahydroimidazo[4,5-c]pyridine-5-carboxylic Acid 2-chlorobenzyl Ester Oxalate

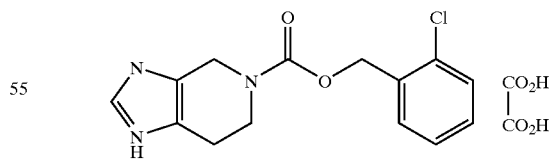

The compound was prepared from 4,5,6,7-tetrahydro-1H-imidazo[4,5-c]pyridine and 2-chlorobenzyl alcohol.

M.p. 173–175° C. $^1$H NMR (400 MHz, DMSO-d$_6$) δ2.65 (m, 2H), 3.71 (s, br, 2H), 4.48 (m, 2H), 5.19 (s, 2H), 7.38 (m, 2H), 7.50 (m, 2H), 8.09 (s, br, 1H).

($C_{14}H_{14}ClN_3O_2$, $C_2H_2O_4$); calcd. 50.34C 4.22H 11.01N; found 50.21; C, 4.19H 10.81N.

Example 43

4,5,6,7-Tetrahydroimidazo[4,5-c]pyridine-5-carboxylic Acid 2-trifluoromethylbenzyl Ester Oxalate

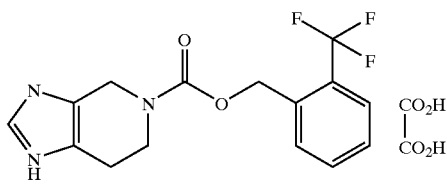

The compound was prepared from 4,5,6,7-tetrahydro-1H-imidazo[4,5-c]pyridine and 2-(trifluoromethyl)benzyl alcohol.

M.p. 152–156° C. (EtOAc). $^1$H NMR (400 MHz, DMSO-d$_6$) δ2.67 (m, 2H), 3.71 (m, 2H), 4.48 (s, br, 2H), 5.28 (s, 2H), 7.58 (t, J=8 Hz, 1H), 7.65–7.81 (m, 3H), 8.14 (m, 1H).

($C_{15}H_{14}F_3O_2$, $C_2H_2O_4$); calcd. 49.16C 3.88H 10.12N; found 49.21C 3.86H 10.11N.

Example 44

4,5,6,7-Tetrahydroimidazo[4,5-c]pyridine-5-carboxylic Acid 1-phenylethyl Ester Oxalate

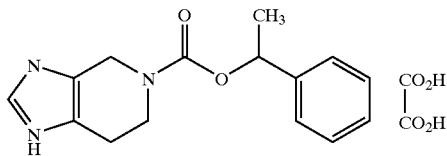

The compound was prepared from 4,5,6,7-tetrahydro-1H-imidazo[4,5-c]pyridine and 1-phenylethanol.

M.p. 162° C. (decomposes; EtOAc/MeOH). $^1$H NMR (300 MHz, DMSO-d$_6$) δ1.49 (d, J=7 Hz, 3H), 2.62 (s, br, 2H), 3.62–3.80 (m, 2H), 4.38–4.60 (m, 2H), 5.74 (q, J=7 Hz, 1H), 7.25–7.40 (m, 5H). 8.06 (s, br, 1H).

Calcd. 56.51C 5.30H 11.63N; found 56.46C 5.28H 11.48N.

Example 45

(4-Benzylpiperidin-1-yl)-(4,5,6,7-tetrahydroimidazo[4,5-c]pyridin-5-yl)methanone Oxalate

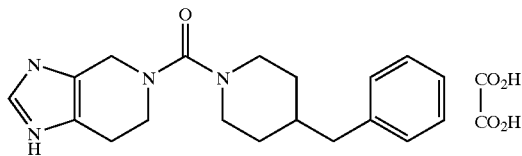

The compound was prepared from 4,5,6,7-tetrahydro-1H-imidazo[4,5-c]pyridine and 4-benzylpiperidine according to the following general procedure for the preparation of ureas:

A solution of 4-nitrophenyl chloroformate (1.04 g, 5.2 mmol) in DCM (10 mL) was dropwise added to a solution of 4,5,6,7-tetrahydro-1H-imidazo[4,5-c]pyridine (1.0 g, 4.7 mmol) in methanol (14 mL) and triethylamine (1.9 mL). The resulting mixture was stirred at 20° C. for 1 h, concentrated under reduced pressure, and the residue was distributed between DCM (40 mL) and water (40 mL). After separation of phases the aqueous phase was extracted with DCM (1×40 mL), and the combined organic phases were dried (MgSO$_4$) and concentrated. The residue was dissolved in DMF (20 mL), 4-benzylpiperidine (1.65 mL, 9.39 mmol) was added, and the resulting mixture was stirred at 80° C. for 17 h. The mixture was concentrated under reduced pressure, and the residue was redissolved in ethyl acetate. After washing with water the organic phase was dried (MgSO$_4$) and filtered. To the filtrate was added a solution of oxalic acid (0.44 g, 4.9 mmol) in ethyl acetate, and the resulting precipitate is filtered off. The resulting solid was distributed between an aqueous solution of NaHCO$_3$ and ethyl acetate, and the organic layer was purified by column chromatography. The purified compound was again precipitated as oxalate from ethyl acetate to yield 0.58 g (30%) of the title oxalate as colorless solid, which does not melt but decomposes upon heating.

$^1$H NMR (400 MHz, DMSO-d$_6$) δ1.06–1.20 (m, 2H), 1.52–1.60 (m, 2H), 1.61–1.75 (m, 1H), 2.52 (m, 2H), 2.65–2.78 (m, 4H), 3.42 (t, J=5 Hz, 2H), 3.55–3.63 (m, 2H), 4.23 (s, 2H), 7.16–7.31 (m, 5H), 8.40 (s, 1H).

Anal. calcd. for $C_{19}H_{24}N_4O$, 1.5 $C_2H_2O_4$ (459.49): 57.51C 5.92H 12.19N; found: 57.67C 6.20H 12.25N.

Example 46

4,5,6,7-Tetrahydroimidazo[4,5-c]pyridine-5-carboxylic Acid N-methyl-N-benzylamide Oxalate

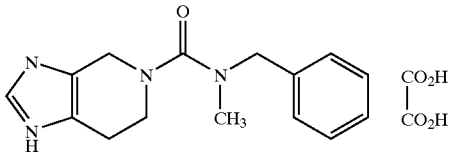

The compound was prepared in the same way as disclosed for example 45 from 4,5,6,7-tetrahydro-1H-imidazo[4,5-c]pyridine and benzylmethylamine.

M.p. 164–166° C. (EtOAc/MeOH). $^1$H NMR (400 MHz, DMSO-d$_6$) δ2.71 (m, 5H), 3.49 (t, J=5 Hz, 2H), 4.23 (s, 2H), 4.36 (s, 2H), 7.23–7.39 (m, 5H), 8.19 (s, 1H).

Calcd. 56.66C 5.59H 15.55N; found 56.75C 5.61H 15.35N.

Example 47

(3,4-Dihydro-1H-isoquinolin-2-yl)(4,5,6,7-tetrahydroimidazo[4,5-c]-pyridin-5-yl)methanone

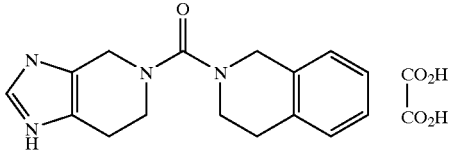

The compound was prepared in the same way as disclosed for example 45 from 4,5,6,7-tetrahydro-1H-imidazo[4,5-c]pyridine and benzylmethylamine.

M.p. 102–104° C. (EtOAc). $^1$H NMR (400 MHz, DMSO-d$_6$) δ2.66 (s, br, 2H), 2.84 (t, J=5 Hz, 2H), 3.46 (m, 4H), 4.21 (s, br, 2H), 4.39 (s, 2H), 7.16 (s, 4H), 7.47 (s, 1H), 11.80 (s, 1H).

Example 48

3,3-Dimethyl-1-(1,4,6,7-tetrahydroimidazo[4,5-c]pyridin-5-yl)-butan-1-one

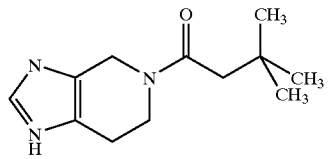

At 0° C., EDC (0.45 g, 2.4 mmol) was added to a solution of tert-butylacetic acid (0.30 mL, 2.3 mmol), and 1-hydroxy-7-azabenzotriazole (0.32 g, 2.4 mmol) in dichloromethane (30 mL). The reaction mixture was stirred for 20 min at 0° C. 4,5,6,7-tetrahydroimidazo[4,5-c]pyridine dihydrochloride (0.50 g, 2.4 mmol) was added. Ethyldiisopropylamine (0.40 mL, 2.4 mmol) was added. The reaction mixture was stirred for 16 h at room temperature. The reaction mixture was diluted with ethyl acetate (100 mL) and washed with 10% aqueous sodium hydrogen sulfate solution (100 mL). A 1 N solution of sodium hydroxide was added to the aqueous solution until pH 12 was obtained. It was extracted with ethyl acetate (2×100 mL). These organic extracts were dried over magnesium sulfate. The solvent was removed in vacuo. The crude product was purified by flash chromatography on silica (40 g), using dichloromethane/methanol/25% aqueous ammonia (100:10:1) as eluent to give 125 mg of the title compound.

$^1$H NMR (CDCl$_3$, 2 rotamers): δ 1.03 and 1.10 (both s, together 9H); 2.35 and 2.40 (both s, together 2H); 2.68 and 2.78 (both t, together 2H); 3.80 and 3.95 (both t, together 2H); 4.55 and 4.70 (both s, together 2H); 7.53 (s, 1H).

For biological testing it was transferred into its acetate salt by lyophilization with 0.5 M acetic acid (40 mL).

Example 49

3-Phenyl-1-(1,4,6,7-tetrahydroimidazo[4,5-c]pyridin-5-yl)propynone

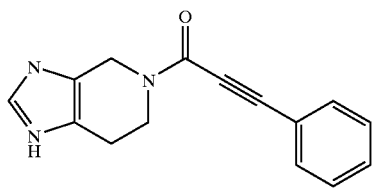

1-Hydroxy-7-azabenzotriazole (0.32 g, 2.4 mmol) was added to a solution of phenylpropiolic acid (0.34 g, 2.4 mmol) in dichloromethane (30 mL). The solution was cooled to 0° C. EDC (0.45 g, 2.4 mmol) was added. The reaction mixture was stirred at 0° C. for 20 min. 4,5,6,7-Tetrahydroimidazo[4,5-c]pyridine dihycrochloride (0.50 g, 2.3 mmol) was added. Ethyldiisopropylamine (0.40 mL, 2.3 mmol) was added. The reaction mixture was stirred for 16 h at room temperature. It was diluted with ethyl acetate (100 mL) and washed with 10% aqueous sodium hydrogensulfate solution (100 mL). The aqueous phase was extracted with ethyl acetate (3×60 mL): It was added a 1 N sodium hydroxide solution until pH 12 was obtained. It was extracted with ethyl acetate (3×90 mL). These extracts were combined and dried over magnesium sulfate. The solvent was removed in vacuo. The crude product was purified by flash chromatography on silica (40 g), using dichloromethane/methanol/25% aqueous ammonia (100:10:1) as eluent, to give 50 mg of the title compound.

$^1$H NMR (CDCl$_3$, 2 rotamers): δ2.75 and 2.85 (both t, together 2H); 4.03 and 4.15 (both t, together 2H); 4.75 and 4.92 (both s, together 1H); 7.10–7.70 (m, 6H).

The title compound was transferred into its oxalate salt by dissolving in ethyl acetate (20 mL) and addition of a solution of oxalic acid in ethyl acetate (20 mL). The precipitation was collected and washed with ethyl acetate (10 mL). It was dried in vacuo.

HPLC: R$_t$=6.922 min (Method h8).

LC-MS calcd. for MH$^+$: 252 found: 252.

Example 50

2E-3-(4-tert-Butylphenyl)-1-(1,4,6,7-tetrahydroimidazo[4,5-c]pyridin-5-yl)propenone

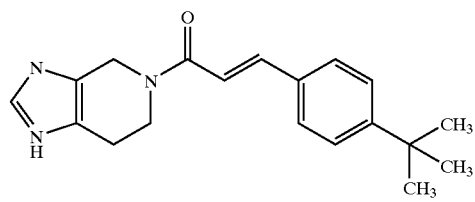

At 0° C., EDC (0.45 g, 2.4 mmol) was added to a solution of 3-(4-tert-butylphenyl)acrylic acid (0.48 g, 2.4 mmol) and 1-hydroxy-7-azabenzotriazole (0.32 g, 2.4 mmol) in dichloromethane (30 mL). The reaction mixture was stirred for 20 min at 0° C. 4,5,6,7-Tetrahydroimidazo[4,5-c]pyridine dihydrochloride (0.50 g, 2.3 mmol) was added. Ethyldiisopropylamine (0.40 mL, 2.3 mmol) was added. The reaction mixture was stirred for 16 h at room temperature. It was diluted with ethyl acetate (100 mL) and washed with a saturated aqueous solution of sodium hydrogencarbonate (100 mL). The aqueous phase was extracted with ethyl acetate (2×60 mL). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 119 mg of the title compound.

$^1$H NMR (CDCl$_3$): δ 1.32 (s, 9H); 2.75 (br, 2H); 3.95 (br, 2H); 4.75 (br, 2H); 6.95 (d, 1H); 7.35–7.55 (m, 5H); 7.65 (d, 1H).

For biological testing, the title compound was transferred into its oxalate salt: The title compound was dissolved in ethyl acetate (15 mL). A solution of oxalic acid (58 mg, 0.64 mmol) in ethyl acetate (15 mL) was added. The precipitation was collected, washed with ethyl acetate (10 mL) and dried in vacuo.

HPLC: R$_t$ 9.55 min (Method h8).

LC-MS: calcd. for MH$^+$: 310; found 310.

Example 51

2-Bicyclo[2.2.1]hept-2-yl-1-(1,4,6,7-tetrahydroimidazo[4,5-c]pyridin-5-yl)ethanone

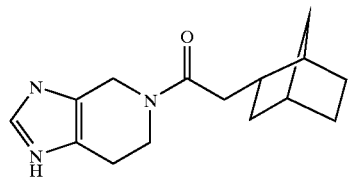

At 0° C., EDC (0.45 g, 2.4 mmol) was added to a solution of 1-hydroxy-7-azabenzotriazole (0.32 g, 2.4 mmol) and 2-norbornaneacetic acid (0.338 mL, 2.4 mmol) in dichloromethane (30 mL). The reaction mixture was stirred for 20 min at 0° C. 4,5,6,7-Tetrahydroimidazo[4,5-c]pyridine dihydrochloride (0.50 g, 2.3 mmol) was added. Ethyldiisopropylamine (0.40 mL, 2.3 mmol) was added. The reaction mixture was stirred for 16 h at room temperature. It was diluted with ethyl acetate (100 mL) and washed with a saturated aqueous solution of sodium hydrogencarbonate (100 mL). The aqueous solution was extracted with ethyl acetate (2×60 mL). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 120 mg of the title compound.

$^1$H NMR (CDCl$_3$, 2 rotamers): δ 1.00–2.50 (m, 13H); 2.65 and 2.75 (both t, together 2H); 3.75 and 3.90 (both t, together 2H); 4.55 and 4.65 (both s, together 2H); 7.53 (s, 1H).

For biological testing, the title compound was transferred into its oxalate salt: The title compound was dissolved in ethyl acetate (15 mL). A solution of oxalic acid (42 mg, 0.47 mmol) in ethyl acetate (15 mL) was added. The precipitation was collected, washed with ethyl acetate (10 mL) and dried in vacuo.

HPLC: R$_t$=7.59 min (Method h8).

LC-MS: calcd. for MH$^+$: 260; found 260. C$_{15}$H$_{21}$N$_3$O.C$_2$H$_2$O$_4$ (349.39) calcd: 58.44C 6.64H 12.03N; found: 58.72C 6.70H 11.99 N.

Example 52

4-Pentylphenyl-(1,4,6,7-tetrahydroimidazo[4,5-c]pyridin-5-yl)methanone Hydrochloride

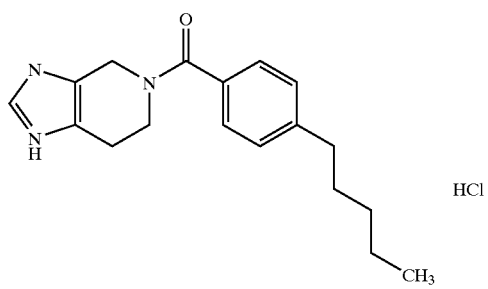

To a solution of 4-pentylbenzoic acid (0.77 g, 4 mmol) in DMF (10 mL) was added carbonyl diimidazole (0.65 g, 4 mmol) and the mixture was stirred at room temperature for 2 h. 4,5,6,7-Tetrahydro-1H-imidazo[4,5-c]pyridine (0.81 g, 3.8 mmol) and triethylamine (1.6 mL) were added and the mixture was stirred at room temperature overnight.

The mixture was concentrated under reduced pressure, and water (50 mL) and ethyl acetate (50 mL) were added to the residue. The organic phase was washed with water twice, with brine, dried (MgSO4), and mixed with a solution of oxalic acid (0.35 g) in ethyl acetate (20 mL). The mixture was kept at room temperature overnight, filtered, and the resulting solid was dried under reduced pressure. 1.08 g (73%) of the colourless oxalate were obtained.

The oxalate was dissolved in water (50 mL) and sodium hydroxide (2 mL, 4N in water) was added. The free base was extracted with ethyl acetate (2×100 mL), and after drying (MgSO4) and concentration it was redissolved in hydrochloric acid (1N in water). Concentration and precipitation from acetone yielded 0.45 g (36%) of the title compound as colourless solid.

M.p. 180–183° C. $^1$H NMR (300 MHz, DMSO-d$_6$): δ0.88 (t, J=7 Hz, 3H), 1.22–1.40 (m, 4H), 1.59 (quintt, J=7 Hz, 2H), 2.62 (t, J=7 Hz, 2H), 2.78 (m, 2H), 3.1–4.1 (m, 4H), 7.30 (d, J=8 Hz, 2H), 7.39 (d, J=8 Hz, 2H), 8.95 (s, 1H), 14.65 (s, br, 1H).

Example 53

4-Trifluoromethoxyphenyl-(1,4,6,7-tetrahydroimidazo[4,5-c]pyridin-5-yl)methanone Hydrochloride

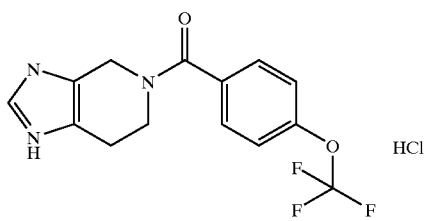

The compound was prepared in the same way as example 52 from 4-trifluoro-methoxybenzoic acid and 4,5,6,7-tetrahydro-1H-imidazo[4,5-c]pyridine.

M.p. 239–242° C. $^1$H NMR (300 MHz, DMSO-d$_6$): δ 2.80 (m, 2H), 3.04.8 (m, 4H), 7.48 (d, J=8 Hz, 2H), 7.65 (d, J=8 Hz, 2H), 8.98 (s, 1H), 14.75 (s, br, 1H).

Example 54

4-Trifluoromethylphenyl-(1,4,6,7-tetrahydroimidazo[4,5-c]pyridin-5-yl)methanone Oxalate

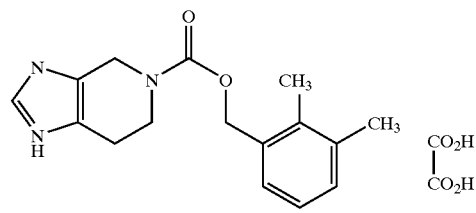

The compound was prepared in the same way as example 52 from 4-trifluoromethylbenzoic acid and 4,5,6,7-tetrahydro-1H-imidazo[4,5-c]pyridine.

M.p. 201–203° C. $^1$H NMR (mixture of rotamers, 400 MHz, DMSO-d$_6$): δ2.66–2.80 (m, 2H), 3.54 (s, br, 1.5H), 3.96 (s, br, 0.5H), 4.38 (s, br, 0.5H), 4.69 (s, 1.5H), 7.68 (m, 2H), 7.85 (d, J=8 Hz, 2H), 8.02 (s, br, 0.25H), 8.20 (s, 0.75H).

Example 55

4-Isobutylphenyl-(1,4,6,7-tetrahydroimidazo[4,5-c]pyridin-5-yl)methanone Oxalate

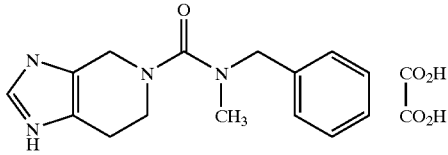

The compound was prepared in the same way as example 52 from 4-isobutylbenzoic acid and 4,5,6,7-tetrahydro-1H-imidazo[4,5-c]pyridine.

M.p. 185–186° C. $^1$H NMR (400 MHz, DMSO-$d_6$) δ 0.88 (d, J=7 Hz, 6H), 1.88 (sept, J=7 Hz, 1H), 2.50 (d, J=7 Hz, 2H), 2.71 (s, br, 2H), 3.55–3.99 (m, 2H), 4.38–4.65 (m, 2H), 7.25 (d, J=8 Hz, 2H), 7.38 (d, J=8 Hz, 2H), 7.98–8.21 (m, 1H).

Example 56

4-Chlorophenyl-(1,4,6,7-tetrahydroimidazo[4,5-c]pyridin-5-yl)methanone Oxalate

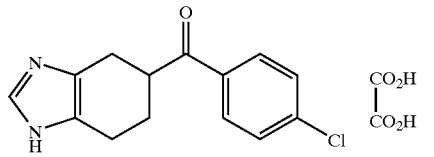

The compound was prepared in the same way as example 52 from 4-chlorobenzoic acid and 4,5,6,7-tetrahydro-1H-imidazo[4,5-c]pyridine.

M.p. 228–230° C. $^1$H NMR (mixture of rotamers, 400 MHz, DMSO-$d_6$): δ 2.72 (s, br, 2H), 3.56 (s, br, 1.5H), 3.93 (s, br, 0.5H), 4.42 (s, br, 0.5H), 4.64 (s, 1.5H), 7.48 (d, J=8 Hz, 2H), 7.53 (d, J=8 Hz, 2H), 8.02 (s, br, 0.25H), 8.18 (s, 0.75H).

Furthermore, the following preferred compounds according to the invention may be prepared according to the general procedures set forth in the foregoing description:

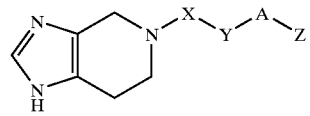

| Example No | -X-Y-A-Z |
|---|---|
| 57 | 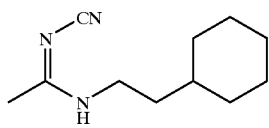 |
| 58 | 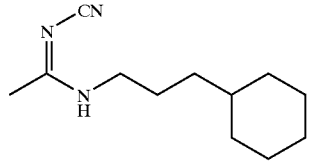 |
| 59 | 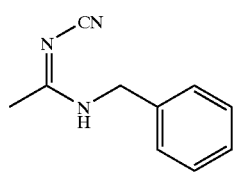 |
| 60 | 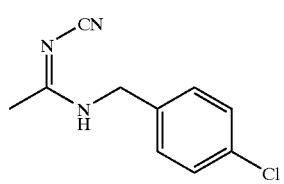 |
| 61 | 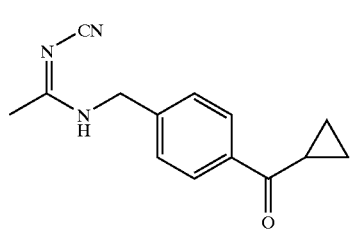 |
| 62 | 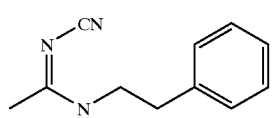 |
| 63 | 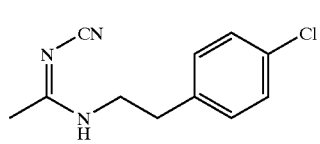 |
| 64 | 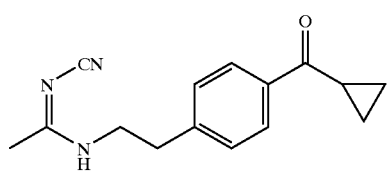 |
| 65 | 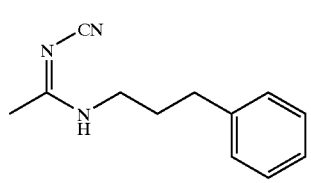 |

-continued
| Example No | -X-Y-A-Z |
|---|---|
| 66 | 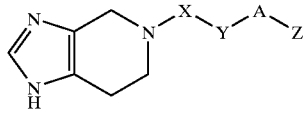 |
| 67 | 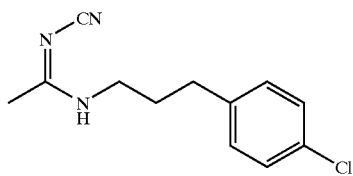 |
| 68 | 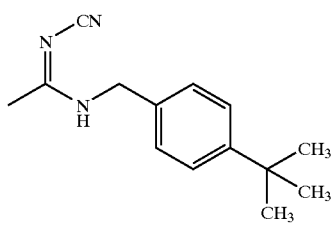 |
| 69 | 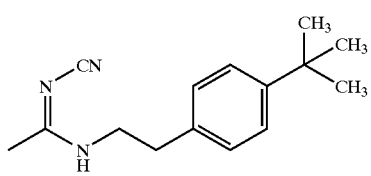 |
| 70 | 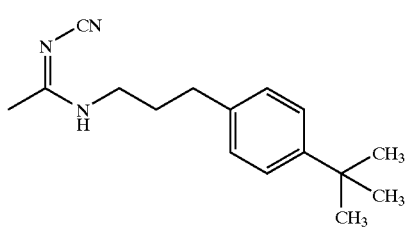 |
| 71 | 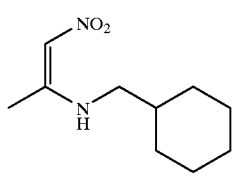 |
| 72 | 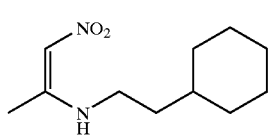 |
-continued
| Example No | -X-Y-A-Z |
|---|---|
| 73 | 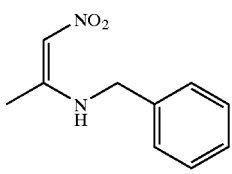 |
| 74 | 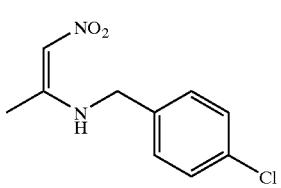 |
| 75 | 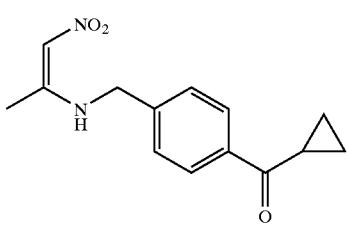 |
| 76 | 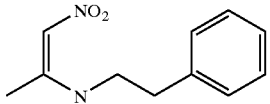 |
| 77 | 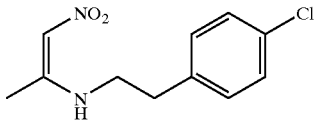 |
| 78 | 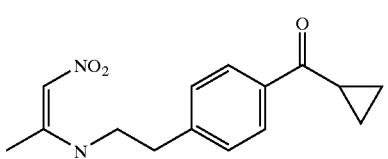 |
| 79 | 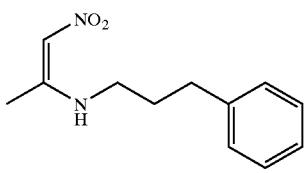 |
| 80 | 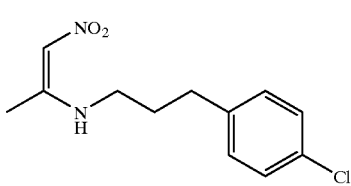 |

-continued
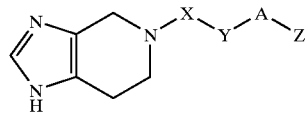
| Example No | -X-Y-A-Z |
|---|---|
| 81 | 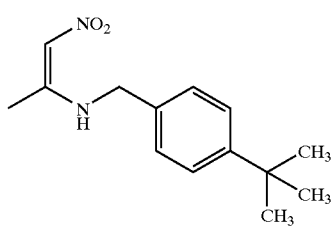 |
| 82 | 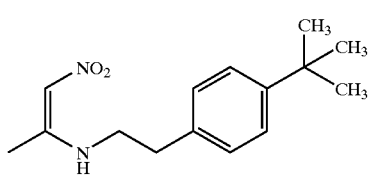 |
| 83 | 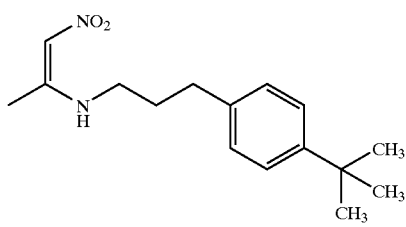 |
| 84 | 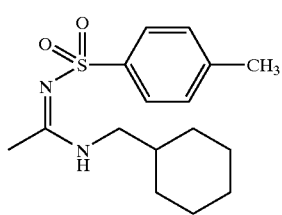 |
| 85 | 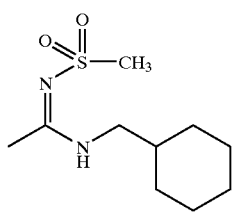 |
| 86 | 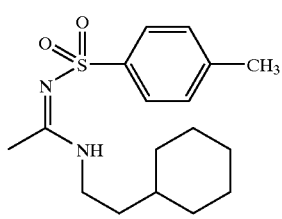 |
-continued
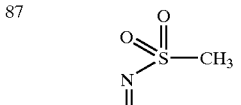
| Example No | -X-Y-A-Z |
|---|---|
| 87 | 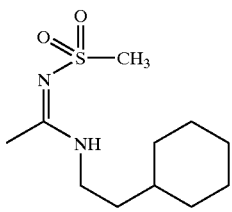 |
| 88 | 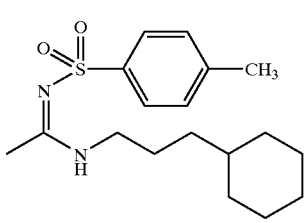 |
| 89 | 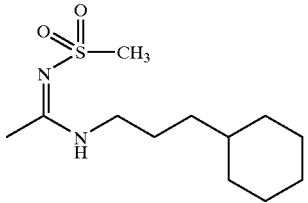 |
| 90 | 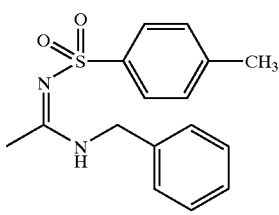 |
| 91 | 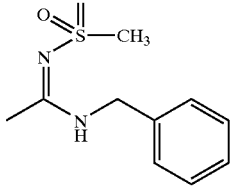 |
| 92 | 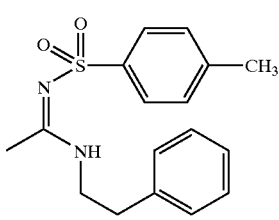 |

-continued

![structure](imidazole-tetrahydropyridine with N-X-Y-A-Z)

| Example No | -X-Y-A-Z |
|---|---|
| 93 | CH₃SO₂-N=C(CH₃)-NH-CH₂CH₂-C₆H₅ |
| 94 | 4-CH₃-C₆H₄-SO₂-N=C(CH₃)-NH-CH₂CH₂CH₂-C₆H₅ |
| 95 | CH₃SO₂-N=C(CH₃)-NH-CH₂CH₂CH₂-C₆H₅ |
| 96 | 4-CH₃-C₆H₄-SO₂-N=C(CH₃)-NH-CH₂-C₆H₄-4-C(CH₃)₃ |
| 97 | CH₃SO₂-N=C(CH₃)-NH-CH₂-C₆H₄-4-C(CH₃)₃ |
| 98 | 4-CH₃-C₆H₄-SO₂-N=C(CH₃)-NH-CH₂-C₆H₄-4-C(O)-cyclopropyl |
| 99 | CH₃SO₂-N=C(CH₃)-NH-CH₂-C₆H₄-4-C(O)-cyclopropyl |
| 100 | 4-CH₃-C₆H₄-SO₂-N=C(CH₃)-NH-CH₂CH₂-C₆H₄-4-C(CH₃)₃ |
| 101 | |
| 102 | 4-CH₃-C₆H₄-SO₂-N=C(CH₃)-NH-CH₂CH₂CH₂-C₆H₄-4-C(CH₃)₃ |
| 103 | CH₃SO₂-N=C(CH₃)-NH-CH₂CH₂CH₂-C₆H₄-4-C(CH₃)₃ |

-continued
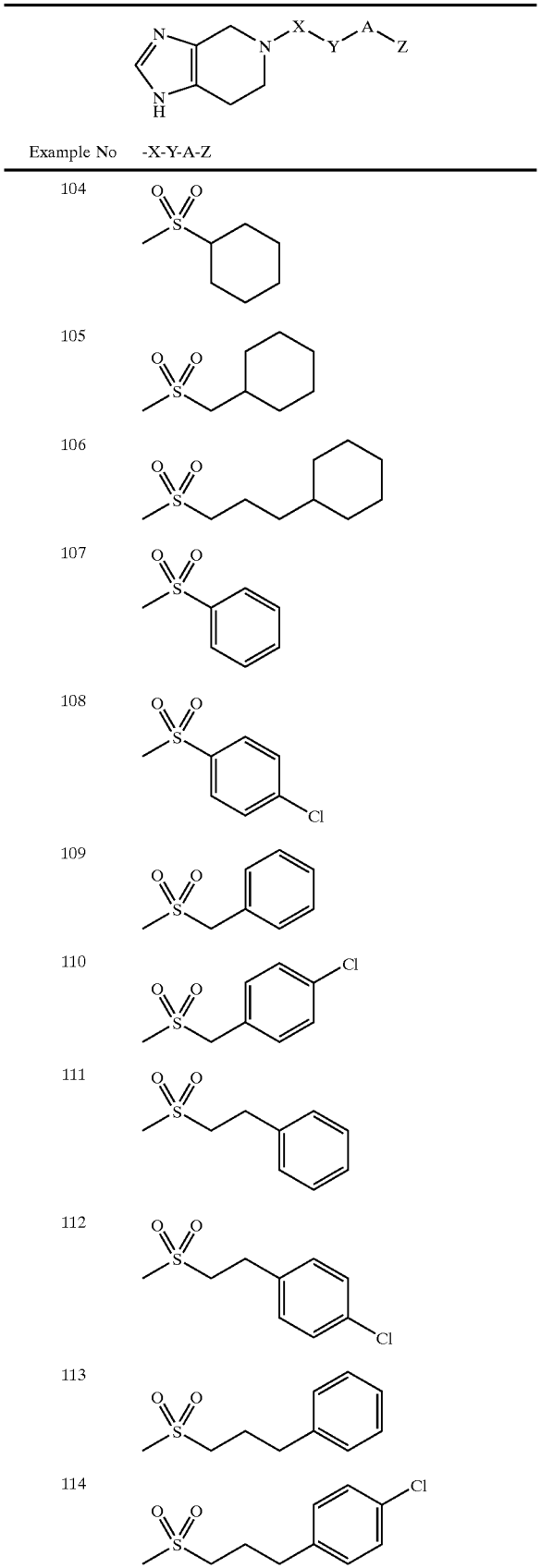
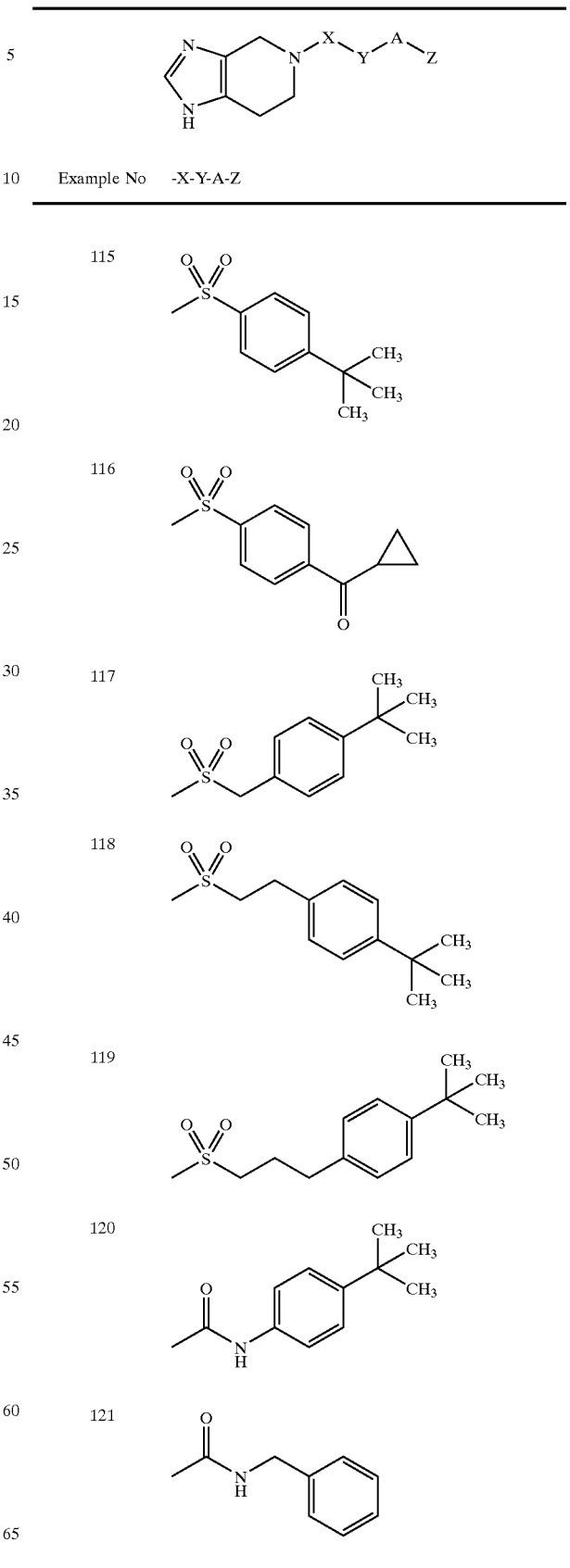

-continued

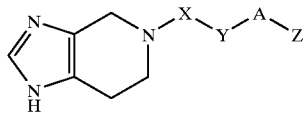

| Example No | -X-Y-A-Z |
|---|---|
| 122 | 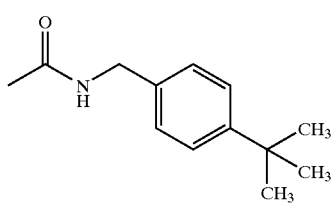 |
| 123 | 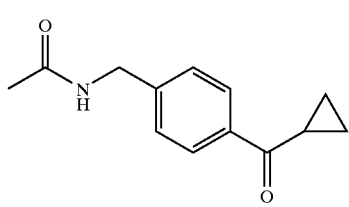 |

-continued

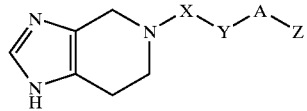

| Example No | -X-Y-A-Z |
|---|---|
| 124 | 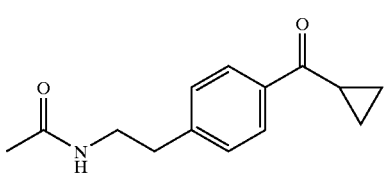 |

The following examples were prepared according to General Procedure C, D or E. The molecular weights of the examples were all confirmed by MS:

| Example No | Name/Structure | Purity (%) (HPLC/UV) | MW |
|---|---|---|---|
| 125 | Cyclohexyl-(4,5,7,8-tetrahydroimidazo[4,5-d]azepin-6-yl)methanone 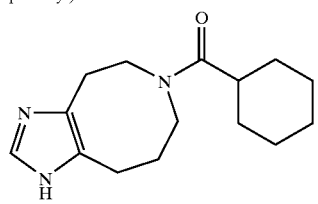 | 90 | 247.3 |
| 126 | Cyclohexylmethyl-(4,5,7,8-tetrahydroimidazo-[4,5-d]azepin-6-yl)methanone 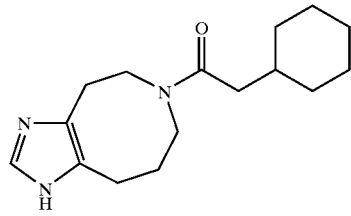 | 90 | 261.4 |
| 127 | (2-Cyclohexylethyl)-(4,5,7,8-tetrahydroimidazo-[4,5-d]azepin-6-yl)methanone 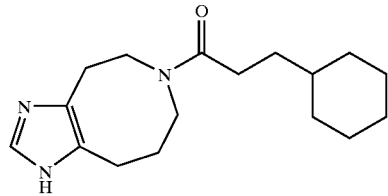 | 90 | 275.4 |

-continued

| Example No | Name/Structure | Purity (%) (HPLC/UV) | MW |
|---|---|---|---|
| 128 | (3-Cyclohexylpropyl)-(4,5,7,8-tetrahydroimidazo-[4,5-d]azepin-6-yl)methanone | 90 | 289.4 |
| 129 | Phenyl-(4,5,7,8-tetrahydroimidazo[4,5-d]azepin-6-yl)methanone | 92 | 241.3 |
| 130 | Benzyl-(4,5,7,8-tetrahydroimidazo[4,5-d]azepin-6-yl)methanone | 90 | 255.3 |
| 131 | (2-Phenylethyl)-(4,5,7,8-tetrahydroimidazo[4,5-d]azepin-6-yl)methanone | 90 | 269.3 |
| 132 | (3-Phenylpropyl)-(4,5,7,8-tetrahydroimidazo[4,5-d]azepin-6-yl)methanone | 92 | 283.4 |
| 133 | (4-tert-Butylphenyl)-(4,5,7,8-tetrahydroimidazo[4,5-d]azepin-6-yl)methanone | 92 | 297.4 |

-continued

| Example No | Name/Structure | Purity (%) (HPLC/UV) | MW |
|---|---|---|---|
| 134 | (4-Cyclopropanoylphenyl)-(4,5,7,8-tetrahydro-imidazo[4,5-d]azepin-6-yl)methanone | 90 | 309.4 |
| 135 | (trans-2-Phenylcyclopropyl)-(4,5,7,8-tetrahydro-imidazo[4,5-d]azepin-6-yl)methanone | 90 | 281.4 |
| 136 | 4-Chlorophenyl-(4,5,7,8-tetrahydroimidazo[4,5-d]azepin-6-yl)methanone | 83 | 275.7 |
| 137 | (4-Chlorophenylmethyl)-(4,5,7,8-tetrahydro-imidazo[4,5-d]azepin-6-yl)methanone | 90 | 289.8 |
| 138 | (2-(4-Chlorophenyl)ethyl)-(4,5,7,8-tetrahydro-imidazo[4,5-d]azepin-6-yl)methanone | 90 | 303.8 |

| Example No | Name/Structure | Purity (%) (HPLC/UV) | MW |
|---|---|---|---|
| 139 | (2-Benzoylethyl)-(4,5,7,8-tetrahydroimidazo[4,5-d]azepin-6-yl)methanone 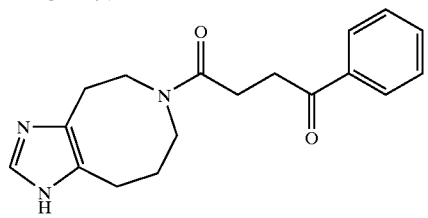 | 92 | 297.4 |
| 140 | 4,5,7,8-Tetrahydroimdazo[4,5-d]azepine-6-carboxylic acid cyclohexyl ester 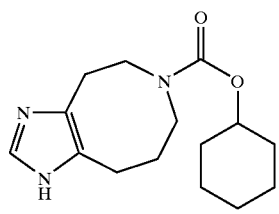 | 97 | 263.3 |
| 141 | 4,5,7,8-Tetrahydroimidazo[4,5-d]azepine-6-carboxylic acid cyclohexylmethyl ester 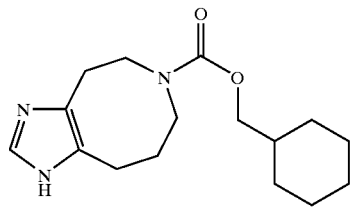 | 92 | 277.4 |
| 142 | 4,5,7,8-Tetrahydroimidazo[4,5-d]azepine-6-carboxylic acid (2-cyclohexylethyl) ester 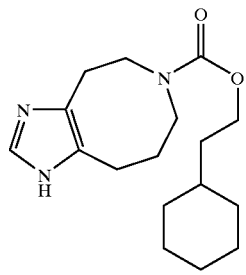 | 82 | 291.4 |
| 143 | 4,5,7,8-Tetrahydroimidazo[4,5-d]azepine-6-carboxylic acid (3-cyclohexylpropyl) ester 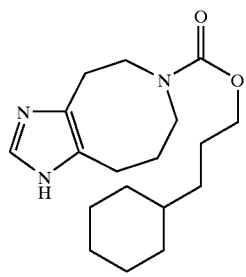 | 75 | 305.4 |

-continued

| Example No | Name/Structure | Purity (%) (HPLC/UV) | MW |
|---|---|---|---|
| 144 | 4,5,7,8-Tetrahydroimidazo[4,5-d]azepine-6 carboxylic acid phenyl ester | 75 | 257.3 |
| 145 | 4,5,7,8-Tetrahydroimidazo[4,5-d]azepine-6-carboxylic acid benzyl ester | 95 | 271.3 |
| 146 | 4,5,7,8-Tetrahydroimidazo[4,5-d]azepine-6-carboxylic acid (2-phenylethyl) ester | 97 | 285.3 |
| 147 | 4,5,7,8-Tetrahydroimidazo[4,5-d]azepine-6-carboxylic acid 3-phenylpropyl ester | 94 | 299.4 |
| 148 | 4,5,7,8-Tetrahydroimidazo[4,5-d]azepine-6-carboxylic acid 4-tert-butylphenyl ester | 92 | 313.4 |

-continued

| Example No | Name/Structure | Purity (%) (HPLC/UV) | MW |
|---|---|---|---|
| 149 | 4,5,7,8-Tetrahydroimidazo[4,5-d]azepine-6-carboxylic acid 4-tert-butylphenylmethyl ester | 91 | 327.4 |
| 150 | 4,5,7,8-Tetrahydroimidazo[4,5-d]azepine-6 carboxylic acid 4-tert-butylphenylethyl ester | 95 | 341.5 |
| 151 | 4,5,7,8-Tetrahydroimidazo[4,5-d]azepine-6 carboxylic acid 4-cyclopropanoylphenyl ester | 90 | 325.4 |
| 152 | 4,5,7,8-Tetrahydroimidazo[4,5-d]azepine-6-carboxylic acid 4-cyclopropanoylphenylmethyl ester | 95 | 339.4 |

-continued
| Example No | Name/Structure | Purity (%) (HPLC/UV) | MW |
|---|---|---|---|
| 153 | 4,5,7,8-Tetrahydroimidazo[4,5-d]azepine-6-carboxylic acid 2-(4-cyclopropanoylphenyl)ethyl ester 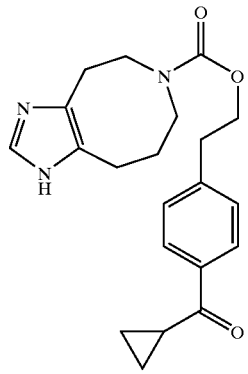 | 95 | 353.4 |
| 154 | 4,5,7,8-Tetrahydroimidazo[4,5-d]azepine-6-carboxylic acid indan-5-yl ester 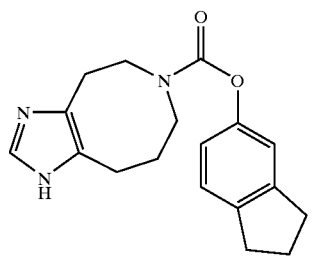 | 86 | 297.4 |
| 155 | 4,5,7,8-Tetrahydroimidazo[4,5-d]azepine-6-carboxylic acid cyclohexyl amide 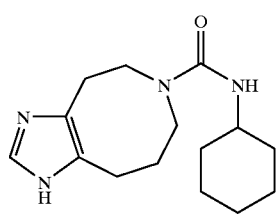 | 90 | 262.4 |
| 156 | 4,5,7,8-Tetrahydroimidazo[4,5-d]azepine-6-carboxylic acid cyclohexylmethyl amide 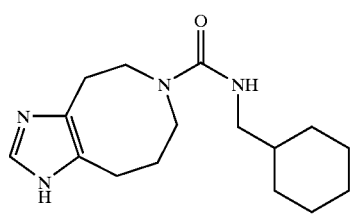 | 90 | 276.4 |

| Example No | Name/Structure | Purity (%) (HPLC/UV) | MW |
|---|---|---|---|
| 157 | 4,5,7,8-Tetrahydroimidazo[4,5-d]azepine-6-carboxylic acid 2-cyclohexylethyl amide | 92 | 290.4 |
| 158 | 4,5,7,8-Tetrahydroimidazo[4,5-d]azepine-6-carboxylic acid anilide | 99 | 256.3 |
| 159 | 4,5,7,8-Tetrahydroimidazo[4,5-d]azepine-6-carboxylic acid benzylamide | 90 | 270.3 |
| 160 | 4,5,7,8-Tetrahydroimidazo[4,5-d]azepine-6-carboxylic acid 2-phenylethylamide | 90 | 284.4 |
| 161 | 4,5,7,8-Tetrahydroimidazo[4,5-d]azepine-6-carboxylic acid 3-phenylpropylamide | 90 | 298.4 |

| Example No | Name/Structure | Purity (%) (HPLC/UV) | MW |
|---|---|---|---|
| 162 | 4,5,7,8-Tetrahydroimidazo[4,5-d]azepine-6-carboxylic acid 4-tert-butylphenyl amide 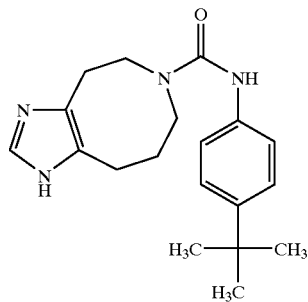 | 98 | 312.4 |
| 163 | 4,5,7,8-Tetrahydroimidazo[4,5-d]azepine-6-carboxylic acid 4-cyclopropanoylphenyl amide 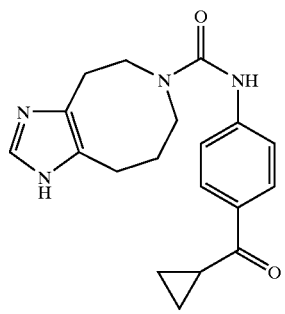 | 90 | 324.4 |
| 164 | 4,5,7,8-Tetrahydroimidazo[4,5-d]azepine-6-carboxylic acid (4-cyclopropanoylphenyl)methyl amide 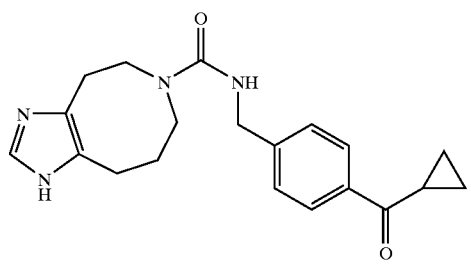 | 90 | 338.4 |
| 165 | 4,5,7,8-Tetrahydroimidazo[4,5-d]azepine-6-carboxylic acid indan-5-yl amide 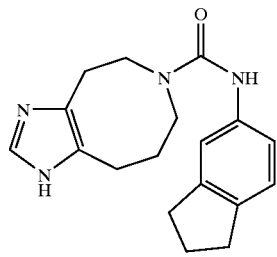 | 98 | 296.4 |

-continued

| Example No | Name/Structure | Purity (%) (HPLC/UV) | MW |
|---|---|---|---|
| 166 | 2-Thienyl(4,5,7,8-tetrahydroimidazo[4,5-d]azepin-6-yl)methanone | 90 | 247.3 |
| 167 | (2-Thienylmethyl)(4,5,7,8-tetrahydroimidazo[4,5-d]azepin-6-yl)methanone | 90 | 261.3 |
| 168 | 2-Naphthyl(4,5,7,8-tetrahydroimidazo[4,5-d]azepin-6-yl)methanone | 90 | 291.4 |
| 169 | (1,2,3,4-Tetrahydronaphthalen-2-yl)(4,5,7,8-tetrahydroimidazo[4,5-d]azepin-6-yl)methanone | 90 | 295.4 |
| 170 | 4,5,7,8-Tetrahydroimidazo[4,5-d]azepine-6-carboxylic acid 4-chlorophenyl amide | 91 | 290.8 |
| 171 | 4,5,7,8-Tetrahydroimidazo[4,5-d]azepine-6-carboxylic acid 4-chlorobenzyl amide | 97 | 304.8 |

-continued

| Example No | Name/Structure | Purity (%) (HPLC/UV) | MW |
|---|---|---|---|
| 172 | 4,5,7,8-Tetrahydroimidazo[4,5-d]azepine-6-carboxylic acid 4-dimethylaminophenyl amide | 76 | 299.4 |
| 173 | 4,5,7,8-Tetrahydroimidazo[4,5-d]azepine-6-carboxylic acid trans-2-phenylcyclopropyl amide | 98 | 296.4 |

Pharmacological Methods

The ability of the compounds to interact with the histamine H3 receptor was determined by the following in vitro binding assays.

Binding Assay I

Rat cerebral cortex was homogenized in ice cold K-Hepes, 5 mM $MgCl_2$ pH 7.1 buffer. After two differential centrifugations the last pellet was resuspended in fresh Hepes buffer containing 1 mg/mL bacitracin. Aliquots of the membrane suspension (400 mg/mL) were incubated for 60 min at 25° C. with 30 pM $[^{125}I]$-iodoproxifan, a known histamine H3 receptor antagonist, and the test compound at various concentrations. The incubation was stopped by dilution with ice-cold medium, followed by rapid filtration through Whatman GF/B filters pretreated for 1 h with 0.5% polyethyleneimine. The radioactivity retained on the filters was counted using a Cobra II auto gamma counter. The radioactivity of the filters was indirectly proportional to the binding affinity of the tested compound. The results were analyzed by nonlinear regression analysis.

Binding Assay II

The H3-receptor agonist ligand R-α-methyl[$^3$H]histamine was incubated with isolated rat cortex cell-membranes at 25° C. for 1 h, followed by a filtration of the incubate through Whatman GF/B filters. Radioactivity retained on the filters was measured using a beta counter.

Male Wistar rats (150–200 g) were decapitated and cerebral cortex was quickly dissected out and frozen immediately on dry ice. Tissue was kept at −80° C. until membrane preparation. During the membrane preparation the tissue was kept on ice all the time. Rat cerebral cortex was homogenized in 10 volumes (w/w) ice-cold Hepes buffer (20 mM Hepes, 5 mM $MgCl_2$ pH 7.1 (KOH)+1 mg/mL bacitracin) using a Ultra-Turrax homogenizer for 30 seconds. The homogenate was centrifuged at 140 g in 10 min. The supernatant was transferred to a new test tube and centrifuged for 30 min at 23 000 g. Pellet was resuspended in 5–10 mL Hepes buffer, homogenized and centrifuged for 10 min at 23 000 g. This short centrifugation step is repeated twice. After the last centrifugation the pellet was resuspended in 24 mL Hepes buffer and the protein concentration was determined. The membranes were diluted to a protein concentration of 5 mg/mL using Hepes buffer, aliquoted and stored at −80° C. until use.

50 µL test-compound, 100 µL membrane (200 µg/mL), 300 µL. Hepes buffer and 50 µL R-α-methyl[$^3$H]histamine (1 nM) were mixed in a test tube. The compounds to be tested were dissolved in DMSO and further diluted in $H_2O$ to the desired concentrations. Radioligand and membranes were diluted in Hepes buffer+1 mg/mL bacitracin. The mixture was incubated for 60 min at 25° C. Incubation was terminated by adding 5 mL ice-cold 0.9% NaCl, followed by rapid filtration through Whatman GF/B filters pre-treated for 1 h with 0.5% polyethyleneimine. The filters were washed with 2×5 mL ice-cold NaCl. To each filter a 3 mL scintillation cocktail was added and the radioactivity retained was measured with a Packard Tri-Carb beta counter.

$IC_{50}$ values were calculated by non-linear regression analysis of binding curves (6 points minimum) using the windows program GraphPad Prism, GraphPad software, USA.

When tested, the present compounds of the formula (I) generally showed a high binding affinity to the histamine H3 receptor.

Preferably, the compounds according to the invention have an $IC_{50}$ value as determined by one or both of the assays of less than 1 µM, more preferred of less than 500 nM and even more preferred of less than 100 nM.

The ability of the present compounds to reduce weight was determined using the in vivo open cage Schedule-fed rat model.

The Open Cage Schedule-Fed Rat Model

Sprague-Dawley (SD) male rats of an age of about 1½ to 2 months and a weight of about 250 g were habituated to the presence of food (Altromin pelleted rat chow) in their home cage only during three hours in the morning from 9 to 12 a.m. all days a week. Water was present ad libitum. As the consumption of food stabilized after 7 to 9 days, the animals were ready for use.

The animals were tested twice a week. During the test sessions, the test compound was administered intraperitoneally 30 minutes before the start of the sessions. One group of 9 animals was administered the test compound at a dose of 15 mg/kg and another group of 11 animals was administered the test compound at a dose of 30 mg/kg. A control group of 11 animals was administered the vehicle consisting of NaCl 0.9% and Chremophor 5%. Food and water intake were monitored at 1, 2 and 3 h post administration.

During the test period the animals were weighed weekly and if necessary extra food was given in order to ensure that the weight gain was 3 to 5 g per week corresponding to the normal weight gain for SD male rats at this age.

Any side effects could rapidly be discovered (barrel-rolling, bushy fur etc.) since the animals were kept in transparent plastic cages to enable continuous monitoring.

What is claimed is:
1. A compound of formula I

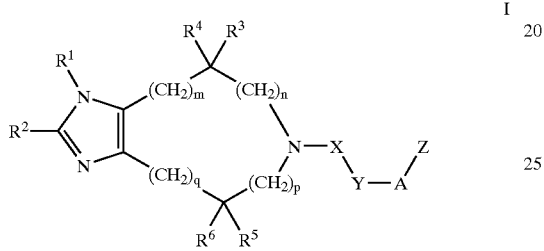

wherein
$R^1$ is hydrogen or a functional group which can be converted to hydrogen in vivo, wherein said functional group is selected from the group consisting of acyl, carbamoyl, monoalkylated carbamoyl, dialkylated carbamoyl, alkoxycarbonyl, $C_{1-6}$alkanoyl, aroyl, $C_{1-6}$alkylcarbamoyl, di-$C_{1-6}$alkylcarbamoyl, dialkylaminosulfonyl, $C_{1-6}$alkoxycarbonyl and 1-($C_{1-6}$alkoxy)-$C_{1-6}$alkyl, $R^2$ is hydrogen, $R^3$ and $R^4$ independently are hydrogen, trifluoromethyl, $C_{1-6}$-alkyl optionally substituted with $C_{3-8}$cycloalkyl, or $R^3$ and $R^4$, together with the carbon atom to which they are connected, form a 3 to 8-membered, saturated or unsaturated, carbocyclic or heterocyclic ring optionally substituted with $C_{1-6}$alkyl, $C_{1-6}$-alkoxy, $C_{1-6}$alkylthio, hydroxy, amino, $C_{1-6}$-alkylamino, di($C_{1-6}$alkyl)amino, halogen, cyano, trifluoromethyl, trifluoromethoxy, heteroaryl, aroyl, heteroaroyl, arylsulfonyl, arylamino or heteroarylamino, $R^5$ and $R^6$ are H, m, n, p are 0, and q is 1, X is —$CH_2$—, —C(=O)—, —C(=S)—, —S(=O)—, —$S(O)_2$—, —C(=N—CN)—,
—C(=CH—$NO_2$)—, —C(=C($CN)_2$)—, —C(=CH—CN)—, or —C(=N—S(=O)$_2R^{11a}$)—, $R^{11a}$ is $C_{1-6}$-alkyl optionally substituted with
aryl, heteroaryl, aroyl, heteroaroyl, arylsulfonyl, arylamino, heteroarylamino or $C_{3-8}$-cycloalkyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, Y is a valence bond, —O— or —N($R^{12}$)—,
wherein $R^{12}$ is
hydrogen,
$C_{1-6}$-alkyl optionally substituted with
aryl, heteroaryl, aroyl, heteroaroyl, arylsulfonyl, arylamino, heteroarylamino or $C_{3-8}$-cycloalkyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, aryl, heteroaryl, aroyl, heteroaroyl, arylsulfonyl or heteroarylsulfonyl, which are optionally substituted with
$C_{1-6}$-alkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, $C_{1-6}$-alkylsulfonyl optionally substituted with
$C_{3-8}$-cycloalkyl, $C_{1-6}$-alkoxy, $C_{1-6}$-alkylthio, hydroxy, amino, $C_{1-6}$-alkylamino, di($C_{1-6}$-alkyl)amino, halogen, cyano, trifluoromethyl, trifluoromethoxy, aryl, heteroaryl, aroyl, heteroaroyl, arylsulfonyl, arylamino or heteroarylamino, A is a valence bond or $C_{1-8}$-alkylene, $C_{2-8}$-alkenylene or $C_{2-8}$-alkynylene, and Z is
Z is $C_{1-6}$-alkyl, phenyl, naphthyl, thienyl, cyclopentyl, cyclohexyl, cyclohexenyl, oxazolyl, indanyl, isoquinolyl, benzoyl or tetrahydronaphthyl which are optionally substituted with one to three substituents selected from the group consisting of $C_{1-6}$-alkyl, $C_{1-6}$-alkoxy, halogen, phenyl, di($C_{1-6}$-alkyl)amino, $C_{3-8}$-cyclopropanecarbonyl, trifluoromethoxy and trifluoromethyl, $C_{2-6}$-alkenyl or $C_{2-6}$-alkynyl), which are optionally substituted with
aryl, arylamino, heteroarylamino, aroyl, heteroaroyl, arylsulfonyl, $C_{1-6}$-alkylsulfonyl, sulfonylamino, arylthio, heteroarylthio, aryloxy, acylamino, heteroaryl or $C_{3-8}$-cycloalkyl, which are optionally substituted with
$C_{1-6}$-alkyl, $C_{1-6}$-alkoxy, $C_{1-6}$-alkylthio, aryl-$C_{1-6}$-alkyl), heteroaryl-$C_{1-6}$-alkyl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, hydroxy, amino, $C_{1-6}$-alkylamino, di($C_{1-6}$-alkyl)amino, halogen, cyano, trifluoromethoxy or trifluoromethyl, —$NR^{13}R^{14}$, in which $R^{13}$ and $R^{14}$ are both phenyl, which phenyl groups are joined with a $C_{1-4}$-alkylene group to form a tricyclic ring system, —$CHR^{13}R^{14}R^{15}$, in which $R^{13}$ is $C_{1-6}$-alkyl or phenyl, and $R^{14}$ is phenyl, or $R^{13}$ and $R^{14}$ are both $C_{1-6}$-alkyl which are joined with $C_{1-4}$-alkylene linkers to form a polycarbocyclic ring system, or
—$CR^{13}R^{14}R^{15}$, in which $R^{13}$, $R^{14}$ and $R^{15}$ are $C_{1-6}$-alkyl which are joined with $C_{1-4}$-alkylene linkers to form a polycarbocyclic ring system, wherein
heteroaryl is a 3 to 7 membered monocyclic or a 9 to 14 membered bi- or tricyclic aromatic system containing one or more heteroatoms selected from N, O or S, which is optionally partially or fully hydrogenated,
heteroarylamino is a radical wherein a —(NH)— group is linked to a heteroaryl group,
heteroaroyl is a radical wherein a —(C=O)— group is linked to a heteroaryl group, provided that
when X is —CS—, $R^1$=hydrogen, the group —Y—A—Z must not start with the radical —NH—,
when X is —CO—, the group —Y—A—Z starts with the radical —NH—, $R^1$=hydrogen, the remainder of the group —Y—A—Z must not be unsubstituted or $C_{1-6}$-alkoxy substituted phenyl, unsubstituted $C_{3-8}$-cycloalkyl or unsubstituted $C_{1-6}$-alkyl,
when X is —CO—, Y is —O—, A is —$CH_2$—, Z is phenyl, $R^1=R^2=R^4=R^5=R^6$=hydrogen, m=n=p=0 and q=1, $R^3$ must not be hydrogen, ethyl, or isopropyl,
or any optical or geometric isomer or tautomeric form thereof or a pharmaceutically acceptable salt thereof.

2. A compound of claim 1, wherein $R^1$=hydrogen.
3. A compound of claim 1, wherein X is C(=O)—.
4. A compound of claim 1, wherein A is a valence bond, methylene, ethylene or propylene.
5. A compound of claim 1, wherein Z is —$NR^{13}R^{14}$, —$CHR^{13}R^{14}$ or —$CR^{13}R^{14}R^{15}$.
6. A compound of claim 1, wherein Z is $C_{1-6}$-alkyl, optionally substituted with $C_{1-6}$-alkyl, $C_{1-6}$-alkoxy, $C_{1-6}$-alkylthio, aryl-$C_{1-6}$-alkyl, heteroaryl-$C_{1-6}$-alkyl, nitro, arylamino, heteroarylamino, aroyl, heteroaroyl, arylsulfonyl, heteroarylsulfonyl, $C_{1-6}$-alkylsulfonyl, sulfonylamino, arylthio, heteroarylthio, aryloxy, acylamino, hydroxy, amino, $C_{1-6}$-alkylamino, di($C_{1-6}$-alkyl)amino, halogen, cyano, trifluoromethoxy or trifluoromethyl.
7. A compound of claim 1, wherein Z is —$NR^{13}R^{14}$ in which $R^{13}$ and $R^{14}$ are both phenyl, which phenyl groups are joined with a $C_{1-4}$-alkylene group to form a tricyclic ring system.
8. A compound of claim 1, wherein Z is —$CHR^{13}R^{14}$, in which $R^{13}$ is $C_{1-6}$-alkyl or phenyl and $R^{14}$ is phenyl, or $R^{13}$ and $R^{14}$ are both $C_{1-6}$-alkyl which are joined with $C_{1-4}$-alkylene linkers to form a polycarbocyclic ring system.
9. A compound of claim 1, wherein Z is —$CR^{13}R^{14}R^{15}$, in which $R^{13}$, $R^{14}$ and $R^{15}$ are $C_{1-6}$-alkyl which are joined with $C_{1-4}$-alkylene linkers to form a polycarbocyclic ring system.
10. A compound of claim 1, wherein $R^3$ and $R^4$ are both hydrogen or are both $C_{1-6}$-alkyl, or $R^3$ and $R^4$, together with the carbon atom to which they are connected, form a $C_{3-8}$-cycloalkyl ring, or one of $R^3$ and $R^4$ is hydrogen while the other is $C_{3-8}$-cycloalkyl substituted $C_{1-6}$-alkyl.
11. A compound of claim 1, wherein $R^3$ and $R^4$, are hydrogen.
12. A compound of claim 1, wherein Z is $C_{1-6}$-alkyl, cyclopentyl, cyclohexyl, cyclohexenyl, oxazolyl, which are optionally substituted with one to three substituents selected from the group consisting of $C_{1-6}$-alkyl, $C_{1-6}$-alkoxy, halogen, phenyl, di($C_{1-6}$-alkyl)amino, $C_{3-8}$-cyclopropanecarbonyl, trifluoromethoxy and trifluoromethyl.

13. A compound of claim 1, wherein Z is cyclohexyl which is optionally substituted with $C_{1-6}$-alkyl, $C_{1-6}$-alkoxy, halogen, phenyl, di($C_{1-6}$-alkyl)amino, $C_{3-8}$-cyclopropanecarbonyl, trifluoromethoxy and trifluoromethyl.

14. The compound of claim 1, wherein heteroaryl is selected from furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, benzothiophenyl, indazolyl, benzimidazolyl, benzthiazolyl, benzisothiazolyl, benzisoxazolyl, purinyl, quinazolinyl, quinolizinyl, quinolinyl, isoquinolinyl, quinoxalinyl, naphthyridinyl, pteridinyl carbazolyl, azepinyl, diazepinyl, acridinyl, pyrrolinyl, pyrazolinyl, indolinyl, pyrrolidinyl, piperidinyl, piperazinyl, azepinyl, diazepinyl, morpholinyl, thiomorpholinyl, oxazolidinyl, oxazolinyl, oxazepinyl, aziridinyl and tetrahydrofuranyl.

15. The compound of claim 1, wherein heteroaroyl is selected from furoyl, thienylcarbonyl, pyridoyl, oxazolylcarbonyl, benzofurylcarbonyl, benzimidazolylcarbonyl, pyrrolinylcarbonyl, azepinylcarbonyl, pyrrolylcarbonyl, thiazolylcarbonyl, imidazolylcarbonyl, isoxazolylcarbonyl, isothiazolylcarbonyl, 1,2,3-triazolylcarbonyl, 1,2,4-triazolylcarbonyl, pyranylcarbonyl, pyridazinylcarbonyl, pyrimidinylcarbonyl, pyrazinylcarbonyl, 1,2,3-triazinylcarbonyl, 1,2,4-triazinylcarbonyl, 1,3,5-triazinylcarbonyl, 1,2,3-oxadiazolylcarbonyl, 1,2,4-oxadiazolylcarbonyl, 1,2,5-oxadiazolylcarbonyl, 1,2,3-thiadiazolylcarbonyl, 1,2,4-thiadiazolylcarbonyl, 1,2,5-thiadiazolylcarbonyl, 1,3,4-thiadiazolylcarbonyl, tetrazolylcarbonyl, thiadiazinylcarbonyl, indolylcarbonyl, isoindolylcarbonyl, benzothienylcarbonyl, benzothiophenylcarbonyl, indazolylcarbonyl, benzthiazolylcarbonyl, benzisothiazolylcarbonyl, benzisoxazolylcarbonyl, purinylcarbonyl, quinazolinylcarbonyl, quinolizinylcarbonyl, quinolinylcarbonyl, isoquinolinylcarbonyl, quinoxalinylcarbonyl, naphthyridinylcarbonyl, pteridinylcarbonyl, carbazolylcarbonyl, azepinylcarbonyl, diazepinylcarbonyl acridinylcarbonyl, pyrrolinylcarbonyl, pyrazolinylcarbonyl, indolinylcarbonyl, piperidinylcarbonyl, piperazinylcarbonyl, diazepinylcarbonyl, morpholinylcarbonyl, thiomorpholinylcarbonyl, oxazolidinylcarbonyl, oxazolinylcarbonyl, oxazepinylcarbonyl, aziridinylcarbonyl and tetrahydrofuranylcarbonyl.

16. The compound of claim 1, wherein heteroarylamino is selected from furanylamino, thienylamino, pyridylamino, oxazolylamino, benzofurylamino, benzimidazolylamino, pyrrolinylamino, azepinylamino, pyrrolylamino, thiazolylamino, imidazolylamino, isoxazolylamino, isothiazolylamino, 1,2,3-triazolylamino, 1,2,4-triazolylamino, pyranylamino, pyridazinylamino, pyrimidinylamino, pyrazinylamino, 1,2,3-triazinylamino, 1,2,4-triazinylamino, 1,3,5-triazinylamino, 1,2,3-oxadiazolylamino, 1,2,4-oxadiazolylamino, 1,2,5-oxadiazolylamino, 1,2,3-thiadiazolylamino, 1,2,4-thiadiazolylamino, 1,2,5-thiadiazolylamino, 1,3,4-thiadiazolylamino, tetrazolylamino, thiadiazinylamino, indolylamino, isoindolylamino, benzothienylamino, benzothiophenylamino, indazolylamino, benzthiazolylamino, benzisothiazolylamino, benzisoxazolylamino, purinylamino, quinazolinylamino, quinolizinylamino, quinolinylamino, isoquinolinylamino, quinoxalinylamino, naphthyridinylamino, pteridinylamino, carbazolylamino, azepinylamino, diazepinylamino, acridinylamino, pyrazolinylamino, indolinylamino, pyrrolidinylamino, piperidinylamino, piperazinylamino, diazepinylamino, morpholinylamino, thiomorpholinylamino, oxazolidinylamino, oxazolinylamino, oxazepinylamino, aziridinylamino and tetrahydrofuranylamino.

17. A composition comprising, as an active ingredient, an effective amount of at least one compound of claim 1, together with one or more pharmaceutically acceptable carriers or diluents.

18. The composition of claim 17 in unit dosage form, comprising from about 0.05 mg to about 1000 mg of the compound.

19. The composition of claim 17 in unit dosage form, comprising from about 0.1 mg to about 500 mg of the compound.

20. The composition of claim 17 in unit dosage form, comprising from about 0.5 mg to about 200 mg of the compound.

21. A method of treating overweight or obesity comprising administering to a subject in need thereof a composition of claim 17.

22. A method of treating overweight or obesity comprising administering to a subject in need thereof the compound of claim 1.

* * * * *